US011421022B2

(12) United States Patent
Fenn et al.

(10) Patent No.: US 11,421,022 B2
(45) Date of Patent: *Aug. 23, 2022

(54) METHOD FOR MAKING ANTIBODY FC-REGION CONJUGATES COMPRISING AT LEAST ONE BINDING ENTITY THAT SPECIFICALLY BINDS TO A TARGET AND USES THEREOF

(71) Applicant: Hoffmann-La Roche Inc., Little Falls, NJ (US)

(72) Inventors: Sebastian Fenn, Munich (DE); Erhard Kopetzki, Penzberg (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 440 days.

This patent is subject to a terminal disclaimer.

(21) Appl. No.: 14/579,192

(22) Filed: Dec. 22, 2014

(65) Prior Publication Data

US 2015/0232541 A1    Aug. 20, 2015

Related U.S. Application Data

(63) Continuation of application No. PCT/EP2013/063259, filed on Jun. 25, 2013.

(30) Foreign Application Priority Data

Jun. 27, 2012  (EP) .................................... 12173876

(51) Int. Cl.
| | |
|---|---|
| C07H 21/04 | (2006.01) |
| C12P 21/06 | (2006.01) |
| C12N 15/00 | (2006.01) |
| C12N 5/00 | (2006.01) |
| C07K 16/00 | (2006.01) |
| C07K 16/18 | (2006.01) |
| C07K 16/32 | (2006.01) |
| C12N 15/62 | (2006.01) |
| C12N 9/52 | (2006.01) |
| A61K 47/68 | (2017.01) |

(52) U.S. Cl.
CPC .......... *C07K 16/18* (2013.01); *A61K 47/6889* (2017.08); *C07K 16/00* (2013.01); *C07K 16/32* (2013.01); *C12N 9/52* (2013.01); *C12N 15/62* (2013.01); *C12Y 304/2207* (2013.01); *C07K 2317/52* (2013.01); *C07K 2317/55* (2013.01); *C07K 2319/00* (2013.01); *C07K 2319/50* (2013.01); *C07K 2319/90* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 3,896,111 A | 7/1975 | Kupchan et al. |
| 4,120,649 A | 10/1978 | Schechter |
| 4,137,230 A | 1/1979 | Hashimoto et al. |
| 4,150,149 A | 4/1979 | Wolfsen et al. |
| 4,151,042 A | 4/1979 | Higahide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| RE30,985 E | 6/1982 | Cartaya |
| 4,361,544 A | 11/1982 | Goldberg |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,419,446 A | 12/1983 | Howely et al. |
| 4,424,219 A | 1/1984 | Hashimoto et al. |
| 4,444,744 A | 4/1984 | Goldenberg |
| 4,450,254 A | 5/1984 | Isley et al. |
| 4,560,655 A | 12/1985 | Baker |
| 4,601,978 A | 7/1986 | Karin |
| 4,657,866 A | 4/1987 | Kumar |

(Continued)

FOREIGN PATENT DOCUMENTS

| | | |
|---|---|---|
| CN | 1173878 A | 2/1998 |
| CN | 1176659 A | 3/1998 |

(Continued)

OTHER PUBLICATIONS

Antos. JBC 2009, 284;23:16028-16036.*

(Continued)

*Primary Examiner* — Chun W Dahle

(74) *Attorney, Agent, or Firm* — Morrison & Foerster LLP

(57) ABSTRACT

Herein is reported a method for producing an antibody Fc-region conjugate comprising as first component an antibody Fc-region and as second component at least one binding entity that specifically binds to a target using a transpeptidase for enzymatic conjugation of the antibody Fc-region to at least one binding entity.

3 Claims, 4 Drawing Sheets

Specification includes a Sequence Listing.

(56) References Cited

U.S. PATENT DOCUMENTS

| | | | |
|---|---|---|---|
| 4,665,077 A | 5/1987 | Stringfellow et al. |
| 4,737,456 A | 4/1988 | Weng et al. |
| 4,767,704 A | 8/1988 | Cleveland et al. |
| 4,816,567 A | 3/1989 | Cabilly et al. |
| 4,927,762 A | 5/1990 | Darfler |
| 4,948,882 A | 8/1990 | Ruth |
| 4,965,199 A | 10/1990 | Capon |
| 4,975,278 A | 12/1990 | Senter et al. |
| 5,053,394 A | 10/1991 | Ellestad et al. |
| 5,114,721 A | 5/1992 | Cohen et al. |
| 5,122,469 A | 6/1992 | Mather et al. |
| 5,143,844 A | 9/1992 | Abrahmsen et al. |
| 5,202,238 A | 4/1993 | Fell, Jr. et al. |
| 5,204,244 A | 4/1993 | Fell et al. |
| 5,208,020 A | 5/1993 | Chari et al. |
| 5,264,365 A | 11/1993 | Georgiou et al. |
| 5,362,852 A | 11/1994 | Geoghegan |
| 5,416,064 A | 5/1995 | Chari et al. |
| 5,451,463 A | 9/1995 | Nelson et al. |
| 5,500,362 A | 3/1996 | Robinson et al. |
| 5,508,192 A | 4/1996 | Georgiou et al. |
| 5,519,142 A | 5/1996 | Hoess et al. |
| 5,532,142 A | 7/1996 | Johnston et al. |
| 5,541,313 A | 6/1996 | Ruth |
| 5,571,894 A | 11/1996 | Wels et al. |
| 5,574,141 A | 11/1996 | Seliger et al. |
| 5,585,481 A | 12/1996 | Arnold, Jr. et al. |
| 5,587,458 A | 12/1996 | King et al. |
| 5,591,828 A | 1/1997 | Bosslet et al. |
| 5,624,821 A | 4/1997 | Winter et al. |
| 5,635,483 A | 6/1997 | Pettit et al. |
| 5,639,635 A | 6/1997 | Joly et al. |
| 5,641,870 A | 6/1997 | Rinderknecht et al. |
| 5,648,020 A | 7/1997 | Winter et al. |
| 5,648,237 A | 7/1997 | Carter |
| 5,648,260 A | 7/1997 | Winter et al. |
| 5,663,149 A | 9/1997 | Pettit et al. |
| 5,712,374 A | 1/1998 | Kuntsmann et al. |
| 5,714,586 A | 2/1998 | Kuntsmann et al. |
| 5,731,168 A | 3/1998 | Carter et al. |
| 5,739,113 A | 4/1998 | Lee |
| 5,739,116 A | 4/1998 | Hamann et al. |
| 5,747,654 A | 5/1998 | Pastan et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,789,199 A | 8/1998 | Joly et al. |
| 5,798,229 A | 8/1998 | Strittmatter et al. |
| 5,817,786 A | 10/1998 | Ruth |
| 5,821,333 A | 10/1998 | Carter et al. |
| 5,821,337 A | 10/1998 | Carter et al. |
| 5,824,483 A | 10/1998 | Houston |
| 5,840,523 A | 11/1998 | Simmons et al. |
| 5,849,879 A | 12/1998 | Nguyen et al. |
| 5,869,046 A | 2/1999 | Presta et al. |
| 5,877,296 A | 3/1999 | Hamann et al. |
| 5,885,793 A | 3/1999 | Griffiths et al. |
| 5,932,448 A | 8/1999 | Tso et al. |
| 5,959,083 A | 9/1999 | Bosslet et al. |
| 5,959,177 A | 9/1999 | Hein et al. |
| 6,027,888 A | 2/2000 | Georgiou et al. |
| 6,040,498 A | 3/2000 | Stomp et al. |
| 6,083,715 A | 7/2000 | Georgiou et al. |
| 6,136,564 A | 10/2000 | Kopetzki |
| 6,153,190 A | 11/2000 | Young et al. |
| 6,166,185 A | 12/2000 | Davis et al. |
| 6,171,586 B1 | 1/2001 | Lam et al. |
| 6,194,551 B1 | 2/2001 | Idusogie et al. |
| 6,239,259 B1 | 5/2001 | Davis et al. |
| 6,248,516 B1 | 6/2001 | Winter et al. |
| 6,267,958 B1 | 7/2001 | Andya et al. |
| 6,350,860 B1 | 2/2002 | Buyse et al. |
| 6,417,429 B1 | 7/2002 | Hein et al. |
| 6,420,548 B1 | 7/2002 | Vezina et al. |
| 6,511,663 B1 | 1/2003 | King et al. |
| 6,531,581 B1 | 3/2003 | Nardone et al. |
| 6,534,628 B1 | 3/2003 | Nilsson et al. |
| 6,558,672 B1 | 5/2003 | Pastan et al. |
| 6,586,207 B2 | 7/2003 | Tirrell et al. |
| 6,602,684 B1 | 8/2003 | Umana et al. |
| 6,630,579 B2 | 10/2003 | Chari et al. |
| 6,660,843 B1 | 12/2003 | Feige et al. |
| 6,833,441 B2 | 12/2004 | Wang et al. |
| 6,835,809 B1 | 12/2004 | Liu et al. |
| 6,878,515 B1 | 4/2005 | Landegren |
| 6,878,575 B2 | 4/2005 | Yoo et al. |
| 6,897,044 B1 | 5/2005 | Braslawsky et al. |
| 6,919,426 B2 | 7/2005 | Boone et al. |
| 6,946,292 B2 | 9/2005 | Kanda et al. |
| 6,982,321 B2 | 1/2006 | Winter |
| 7,041,440 B2 | 5/2006 | Mikoshiba et al. |
| 7,125,978 B1 | 10/2006 | Vezina et al. |
| 7,129,330 B1 | 10/2006 | Little et al. |
| 7,355,008 B2 | 4/2008 | Stavenhagen et al. |
| 7,381,408 B2 | 6/2008 | Mezo et al. |
| 7,498,298 B2 | 3/2009 | Doronina et al. |
| 7,507,796 B2 | 3/2009 | Little et al. |
| 7,642,228 B2 | 1/2010 | Carter et al. |
| 7,651,688 B2 | 1/2010 | Hanai et al. |
| 7,666,622 B2 | 2/2010 | Sharma et al. |
| 7,695,936 B2 | 4/2010 | Carter et al. |
| 7,919,257 B2 | 4/2011 | Hoogenboom et al. |
| 7,928,072 B2 * | 4/2011 | Scaria ................ C07K 14/475 435/212 |
| 7,942,042 B2 | 5/2011 | Kawakita et al. |
| 8,007,813 B2 * | 8/2011 | Walczak .......... C07K 14/70575 424/192.1 |
| 8,216,805 B2 | 7/2012 | Carter et al. |
| 8,227,577 B2 | 7/2012 | Klein et al. |
| 8,242,247 B2 | 8/2012 | Klein et al. |
| 8,268,314 B2 | 9/2012 | Baehner et al. |
| 8,304,713 B2 | 11/2012 | Pradel |
| 8,309,300 B2 | 11/2012 | Jununtual et al. |
| 8,796,424 B2 | 8/2014 | Croasdale et al. |
| 8,871,912 B2 | 10/2014 | Davis et al. |
| 2002/0027751 A1 | 3/2002 | Shimazawa et al. |
| 2002/0051986 A1 | 5/2002 | Baez et al. |
| 2002/0155537 A1 | 10/2002 | Carter et al. |
| 2003/0124129 A1 | 7/2003 | Oliner |
| 2003/0152987 A1 | 8/2003 | Cohen et al. |
| 2003/0170230 A1 | 9/2003 | Caterer et al. |
| 2003/0176352 A1 | 9/2003 | Min et al. |
| 2003/0195156 A1 | 10/2003 | Min et al. |
| 2003/0219817 A1 | 11/2003 | Zhu |
| 2003/0229023 A1 | 12/2003 | Oliner et al. |
| 2003/0236193 A1 | 12/2003 | Oliner et al. |
| 2004/0018557 A1 | 1/2004 | Qu et al. |
| 2004/0033561 A1 | 2/2004 | O'Keefe et al. |
| 2004/0038339 A1 | 2/2004 | Kufer et al. |
| 2004/0214988 A1 | 10/2004 | Tirrell et al. |
| 2004/0220388 A1 | 11/2004 | Metens et al. |
| 2004/0224372 A1 | 11/2004 | Li et al. |
| 2005/0054048 A1 | 3/2005 | Grasso et al. |
| 2005/0064509 A1 | 4/2005 | Bradbury et al. |
| 2005/0079170 A1 | 4/2005 | Le Gall et al. |
| 2005/0100543 A1 | 5/2005 | Hansen et al. |
| 2005/0152894 A1 | 7/2005 | Krummen et al. |
| 2005/0163782 A1 | 7/2005 | Glaser et al. |
| 2005/0169933 A1 | 8/2005 | Steeves et al. |
| 2005/0186208 A1 | 8/2005 | Fyfe et al. |
| 2005/0214833 A1 | 9/2005 | Carter et al. |
| 2005/0238649 A1 | 10/2005 | Doronina et al. |
| 2005/0249722 A1 | 11/2005 | Beliard et al. |
| 2005/0260186 A1 | 11/2005 | Bookbinder et al. |
| 2006/0008845 A1 | 1/2006 | Kondejewski et al. |
| 2006/0063921 A1 | 3/2006 | Moulder et al. |
| 2006/0104968 A1 | 5/2006 | Bookbinder et al. |
| 2006/0122370 A1 | 6/2006 | Oliner et al. |
| 2006/0134709 A1 | 6/2006 | Stavenhagen et al. |
| 2006/0160184 A1 | 7/2006 | Mattheus Hoogenboom et al. |
| 2006/0280747 A1 | 12/2006 | Fuh et al. |
| 2007/0014794 A1 | 1/2007 | Carter et al. |

(56) References Cited

U.S. PATENT DOCUMENTS

| | | |
|---|---|---|
| 2007/0071675 A1 | 3/2007 | Wu et al. |
| 2007/0071742 A1 | 3/2007 | Fang et al. |
| 2007/0141065 A1 | 6/2007 | Fuh et al. |
| 2007/0178552 A1 | 8/2007 | Arathoon et al. |
| 2007/0196274 A1 | 8/2007 | Sun |
| 2007/0269369 A1 | 11/2007 | Gegg et al. |
| 2007/0274985 A1 | 11/2007 | Dubel et al. |
| 2007/0274998 A1 | 11/2007 | Uktu |
| 2007/0287170 A1 | 12/2007 | Davis et al. |
| 2008/0044834 A1 | 2/2008 | Heyduk |
| 2008/0063641 A1 | 3/2008 | Huang et al. |
| 2008/0187954 A1 | 8/2008 | Kallmeier et al. |
| 2008/0280778 A1 | 11/2008 | Urdea |
| 2009/0023811 A1 | 1/2009 | Biadatti et al. |
| 2009/0060910 A1 | 3/2009 | Johnson |
| 2009/0117105 A1 | 5/2009 | Hu et al. |
| 2009/0155275 A1 | 6/2009 | Wu et al. |
| 2009/0162359 A1 | 6/2009 | Klein et al. |
| 2009/0162360 A1 | 6/2009 | Klein et al. |
| 2009/0175851 A1 | 7/2009 | Klein et al. |
| 2009/0194692 A1 | 9/2009 | Kobaru |
| 2009/0232811 A1 | 9/2009 | Klein et al. |
| 2010/0021943 A1 | 1/2010 | An et al. |
| 2010/0062436 A1 | 3/2010 | Jarosch et al. |
| 2010/0081796 A1 | 4/2010 | Brinkman et al. |
| 2010/0111967 A1 | 5/2010 | Baehner et al. |
| 2010/0254989 A1 | 10/2010 | Bossenmaier et al. |
| 2010/0256338 A1 | 10/2010 | Brinkmann et al. |
| 2010/0256339 A1 | 10/2010 | Bossenmaier et al. |
| 2010/0256340 A1 | 10/2010 | Brinkmann et al. |
| 2010/0266617 A1 | 10/2010 | Carven et al. |
| 2010/0316645 A1 | 12/2010 | Imhof-Jung et al. |
| 2010/0322934 A1 | 12/2010 | Imhof-Jung et al. |
| 2010/0322935 A1 | 12/2010 | Croasdale et al. |
| 2011/0054151 A1 | 3/2011 | Lazar et al. |
| 2011/0243966 A1 | 10/2011 | Farrington et al. |
| 2012/0149879 A1 | 6/2012 | Brinkmann et al. |
| 2012/0164726 A1 | 6/2012 | Klein et al. |
| 2012/0184718 A1 | 7/2012 | Bruenker et al. |
| 2012/0225071 A1 | 9/2012 | Klein et al. |
| 2012/0237506 A1 | 9/2012 | Bossenmaier et al. |
| 2012/0237507 A1 | 9/2012 | Bossenmaier et al. |
| 2012/0302737 A1 | 11/2012 | Christensen et al. |
| 2012/0321627 A1 | 12/2012 | Baehner et al. |
| 2013/0022601 A1 | 1/2013 | Brinkmann et al. |
| 2013/0058937 A1 | 3/2013 | Auer et al. |
| 2013/0060011 A1 | 3/2013 | Bruenker et al. |
| 2013/0078249 A1 | 3/2013 | Ast et al. |
| 2013/0156772 A1 | 6/2013 | Bossenmaier et al. |
| 2013/0266568 A1 | 10/2013 | Brinkmann et al. |
| 2013/0267686 A1 | 10/2013 | Brinkmann et al. |
| 2013/0273054 A1 | 10/2013 | Bossenmaier et al. |
| 2013/0288267 A1 | 10/2013 | Gerg et al. |
| 2013/0344094 A1 | 12/2013 | Gerg et al. |
| 2014/0249296 A1 | 9/2014 | Ploegh et al. |
| 2014/0294810 A1 | 10/2014 | Lowman et al. |
| 2014/0370019 A1 | 12/2014 | Bruenker et al. |
| 2015/0004166 A1 | 1/2015 | Baehner et al. |
| 2015/0030598 A1 | 1/2015 | Croasdale et al. |
| 2015/0016670 A1 | 6/2015 | Zhou et al. |
| 2015/0232560 A1 | 8/2015 | Heindl et al. |
| 2015/0232561 A1 | 8/2015 | Fenn et al. |
| 2015/0291704 A1 | 10/2015 | Beck et al. |
| 2016/0194410 A1 | 7/2016 | Gallusser |
| 2017/0275380 A1 | 9/2017 | Gerg |
| 2017/0275381 A1 | 9/2017 | Gerg |
| 2019/0002570 A1 | 1/2019 | Fenn et al. |
| 2020/0207874 A1 | 7/2020 | Gerg |

FOREIGN PATENT DOCUMENTS

| | | |
|---|---|---|
| CN | 1232039 A | 10/1999 |
| CN | 1603345 A | 4/2005 |
| CN | 101037671 A | 9/2007 |
| CN | 101052653 A | 10/2007 |
| CN | 101065151 A | 10/2007 |
| CN | 101205255 A | 6/2008 |
| CN | 101218251 A | 7/2008 |
| CN | 101355966 A | 1/2009 |
| EP | 0 292 128 A1 | 11/1988 |
| EP | 0 307 434 B1 | 3/1989 |
| EP | 0 307 434 B2 | 3/1989 |
| EP | 0 313 219 A2 | 4/1989 |
| EP | 0 339 217 B1 | 11/1989 |
| EP | 0 340 109 A2 | 11/1989 |
| EP | 0 404 097 A2 | 12/1990 |
| EP | 0 423 839 A2 | 4/1991 |
| EP | 0 425 235 A2 | 5/1991 |
| EP | 0 523 978 A1 | 1/1993 |
| EP | 0 618 192 A1 | 10/1994 |
| EP | 0 637 593 A1 | 2/1995 |
| EP | 0 786 468 A2 | 7/1997 |
| EP | 1 074 563 A1 | 2/2001 |
| EP | 1 186 613 A1 | 3/2002 |
| EP | 1 391 213 A1 | 2/2004 |
| EP | 1 431 298 A1 | 6/2004 |
| EP | 1 538 221 A1 | 6/2005 |
| EP | 1 870 459 A1 | 12/2007 |
| EP | 2 050 764 A1 | 4/2009 |
| EP | 2 443 154 B1 | 4/2012 |
| JP | H04-501417 A | 3/1992 |
| JP | H08-245698 A | 9/1996 |
| JP | H09-087296 A | 3/1997 |
| JP | 2000-135095 A | 5/2000 |
| JP | 2007-531513 A | 11/2007 |
| JP | 2008-518605 A | 6/2008 |
| JP | 7-501698 A | 8/2008 |
| JP | 2014-525904 A | 10/2014 |
| JP | 5766296 B2 | 8/2015 |
| RU | 2005/124281 A | 1/2006 |
| RU | 2352583 C2 | 4/2006 |
| RU | 2337108 C2 | 10/2008 |
| RU | 2433831 C2 | 11/2011 |
| WO | WO-1987/00195 A1 | 1/1987 |
| WO | WO-1989/02439 A1 | 3/1989 |
| WO | WO-1989/02931 A1 | 4/1989 |
| WO | WO-1989/12642 A1 | 12/1989 |
| WO | WO-1990/03430 A1 | 4/1990 |
| WO | WO-1990/04413 A1 | 5/1990 |
| WO | WO-1990/08156 A1 | 7/1990 |
| WO | WO-1990/08187 A1 | 7/1990 |
| WO | WO-1990/11294 A1 | 10/1990 |
| WO | WO-1991/01133 A1 | 2/1991 |
| WO | WO-1991/06305 A1 | 5/1991 |
| WO | WO-1992/01047 A1 | 1/1992 |
| WO | WO-1992/04053 A1 | 3/1992 |
| WO | WO-1992/11388 A1 | 7/1992 |
| WO | WO-1993/01161 A1 | 1/1993 |
| WO | WO-1993/05060 A1 | 3/1993 |
| WO | WO-1993/06217 A1 | 4/1993 |
| WO | WO-1993/11161 A1 | 6/1993 |
| WO | WO-1993/11162 A1 | 6/1993 |
| WO | WO-1993/16185 A2 | 8/1993 |
| WO | WO-1993/16185 A3 | 8/1993 |
| WO | WO-1993/21232 A1 | 10/1993 |
| WO | WO-1994/04550 A1 | 3/1994 |
| WO | WO-1994/09131 A1 | 4/1994 |
| WO | WO-1994/10202 A1 | 5/1994 |
| WO | WO-1994/10308 A1 | 5/1994 |
| WO | WO-1994/11026 A1 | 5/1994 |
| WO | WO-1994/29350 A2 | 12/1994 |
| WO | WO-1994/29350 A3 | 12/1994 |
| WO | WO-1995/05399 A1 | 2/1995 |
| WO | WO-1995/09917 A1 | 4/1995 |
| WO | WO-1995/17886 A1 | 7/1995 |
| WO | WO-1996/27011 A1 | 9/1996 |
| WO | WO-1996/27612 A1 | 9/1996 |
| WO | WO-1997/01580 A1 | 1/1997 |
| WO | WO-1997/05156 A1 | 2/1997 |
| WO | WO-1997/014719 A1 | 4/1997 |
| WO | WO-1997/028267 A1 | 8/1997 |
| WO | WO-1997/028267 C1 | 8/1997 |
| WO | WO-1997/43451 A1 | 11/1997 |
| WO | WO-98/48032 A2 | 10/1998 |

(56) References Cited

FOREIGN PATENT DOCUMENTS

| | | |
|---|---|---|
| WO | WO-98/48032 A3 | 10/1998 |
| WO | WO-1998/45331 A2 | 10/1998 |
| WO | WO-1998/45331 A3 | 10/1998 |
| WO | WO-1998/45332 A2 | 10/1998 |
| WO | WO-1998/45332 A3 | 10/1998 |
| WO | WO-1998/050431 A2 | 11/1998 |
| WO | WO-1999/06587 A2 | 2/1999 |
| WO | WO-1999/06587 A3 | 2/1999 |
| WO | WO-1999/37791 A1 | 7/1999 |
| WO | WO-1999/54342 A1 | 10/1999 |
| WO | WO-1999/66951 A2 | 12/1999 |
| WO | WO-1999/66951 A3 | 12/1999 |
| WO | WO-1999/66951 C1 | 12/1999 |
| WO | WO-2000/24770 A2 | 5/2000 |
| WO | WO-2000/24770 A3 | 5/2000 |
| WO | WO-2000/29004 A1 | 5/2000 |
| WO | WO-2000/35956 A1 | 6/2000 |
| WO | WO-2000/61739 A1 | 10/2000 |
| WO | WO-2001/042505 A2 | 6/2001 |
| WO | WO-2001/042505 A3 | 6/2001 |
| WO | WO-2001/77342 A1 | 10/2001 |
| WO | WO-2001/90192 A2 | 11/2001 |
| WO | WO-2002/02781 A1 | 1/2002 |
| WO | WO-2002/051870 A2 | 7/2002 |
| WO | WO-2002/072141 A2 | 9/2002 |
| WO | WO-2002/072141 A3 | 9/2002 |
| WO | WO-2002/088172 A2 | 11/2002 |
| WO | WO-2002/088172 A3 | 11/2002 |
| WO | WO-2002/092620 A2 | 11/2002 |
| WO | WO-2002/092620 A3 | 11/2002 |
| WO | WO-2002/096948 A2 | 12/2002 |
| WO | WO-2002/096948 A3 | 12/2002 |
| WO | WO-2003/012069 A2 | 2/2003 |
| WO | WO-2003/019145 A2 | 3/2003 |
| WO | WO-2003/019145 A3 | 3/2003 |
| WO | WO-2003/030833 A2 | 4/2003 |
| WO | WO-2003/030833 A3 | 4/2003 |
| WO | WO-2003/031589 A2 | 4/2003 |
| WO | WO-2003/031589 A3 | 4/2003 |
| WO | WO-2003/035694 A2 | 5/2003 |
| WO | WO-2003/035835 A2 | 5/2003 |
| WO | WO-2003/035835 A3 | 5/2003 |
| WO | WO-2003/055993 A1 | 7/2003 |
| WO | WO-2003/057134 A2 | 7/2003 |
| WO | WO-2003/057134 A3 | 7/2003 |
| WO | WO-2003/066660 A2 | 8/2003 |
| WO | WO-03/073238 A2 | 9/2003 |
| WO | WO-03/073238 A3 | 9/2003 |
| WO | WO-2003/097105 A1 | 11/2003 |
| WO | WO-2003/104249 A1 | 12/2003 |
| WO | WO-2003/106501 A1 | 12/2003 |
| WO | WO-2004/032961 A1 | 4/2004 |
| WO | WO-2004/058298 A1 | 7/2004 |
| WO | WO-2004/062602 A2 | 7/2004 |
| WO | WO-2004/062602 A3 | 7/2004 |
| WO | WO-2004/065417 A2 | 8/2004 |
| WO | WO-2004/065540 A2 | 8/2004 |
| WO | WO-2004/065540 A3 | 8/2004 |
| WO | WO-2004/072117 A2 | 8/2004 |
| WO | WO-2004/072117 A3 | 8/2004 |
| WO | WO-2004/081051 A1 | 9/2004 |
| WO | WO-2004/092215 A2 | 10/2004 |
| WO | WO-2004/092215 A3 | 10/2004 |
| WO | WO-2005/000900 A1 | 1/2005 |
| WO | WO-2005/001025 A2 | 1/2005 |
| WO | WO-2005/001025 A3 | 1/2005 |
| WO | WO-2005/004809 A2 | 1/2005 |
| WO | WO-2005/004809 A3 | 1/2005 |
| WO | WO-2005/005635 A2 | 1/2005 |
| WO | WO-2005/005635 A3 | 1/2005 |
| WO | WO-2005/009378 A2 | 2/2005 |
| WO | WO-2005/009378 A3 | 2/2005 |
| WO | WO-2005/011735 A1 | 2/2005 |
| WO | WO-2005/018572 A2 | 3/2005 |
| WO | WO-2005/018572 A3 | 3/2005 |
| WO | WO-2005/027966 A2 | 3/2005 |
| WO | WO-2005/027966 A3 | 3/2005 |
| WO | WO-2005/035572 A2 | 4/2005 |
| WO | WO-2005/035572 A3 | 4/2005 |
| WO | WO-2005/35727 A2 | 4/2005 |
| WO | WO-2005/35727 A3 | 4/2005 |
| WO | WO-2005/044853 A2 | 5/2005 |
| WO | WO-2005/044853 A3 | 5/2005 |
| WO | WO-2005/044859 A2 | 5/2005 |
| WO | WO-2005/044859 A3 | 5/2005 |
| WO | WO-2005/047334 A1 | 5/2005 |
| WO | WO-2005/047335 A1 | 5/2005 |
| WO | WO-2005/047336 A1 | 5/2005 |
| WO | WO-2005/047337 A1 | 5/2005 |
| WO | WO-2005/051976 A2 | 6/2005 |
| WO | WO-2005/063816 A2 | 7/2005 |
| WO | WO-2005/063816 A3 | 7/2005 |
| WO | WO-2005/074417 A2 | 8/2005 |
| WO | WO-2005/74524 A2 | 8/2005 |
| WO | WO-2005/74524 A3 | 8/2005 |
| WO | WO-2005/075514 A2 | 8/2005 |
| WO | WO-2005/117973 A2 | 12/2005 |
| WO | WO-2006/020258 A2 | 2/2006 |
| WO | WO-2006/020258 A3 | 2/2006 |
| WO | WO-2005/074417 A3 | 3/2006 |
| WO | WO-2006/028956 A2 | 3/2006 |
| WO | WO-2006/028956 A3 | 3/2006 |
| WO | WO-2006/031370 A2 | 3/2006 |
| WO | WO-2006/031370 A3 | 3/2006 |
| WO | WO-2006/034488 A2 | 3/2006 |
| WO | WO-2006/034488 A3 | 3/2006 |
| WO | WO-2006/044908 A2 | 4/2006 |
| WO | WO-2006/044908 A3 | 4/2006 |
| WO | WO-2006/045049 A1 | 4/2006 |
| WO | WO-2006/068953 A2 | 6/2006 |
| WO | WO-2006/068953 A3 | 6/2006 |
| WO | WO-2006/082515 A2 | 8/2006 |
| WO | WO-2006/082515 A3 | 8/2006 |
| WO | WO-2006/089364 A1 | 8/2006 |
| WO | WO-2006/091209 A2 | 8/2006 |
| WO | WO-2006/091209 A3 | 8/2006 |
| WO | WO-2006/093794 A1 | 9/2006 |
| WO | WO-2006/103100 A2 | 10/2006 |
| WO | WO-2006/103100 A3 | 10/2006 |
| WO | WO-2006/113665 A2 | 10/2006 |
| WO | WO-2006/114700 A2 | 11/2006 |
| WO | WO-2006/114700 A3 | 11/2006 |
| WO | WO-2006/116260 A2 | 11/2006 |
| WO | WO-2006/116260 A3 | 11/2006 |
| WO | WO-2006/137932 A2 | 12/2006 |
| WO | WO-2006/137932 A3 | 12/2006 |
| WO | WO-2007/024715 A2 | 3/2007 |
| WO | WO-2007/031875 A2 | 3/2007 |
| WO | WO-2007/031875 A3 | 3/2007 |
| WO | WO-2007/038658 A2 | 4/2007 |
| WO | WO-2007/038658 A3 | 4/2007 |
| WO | WO-2007/044887 A2 | 4/2007 |
| WO | WO-2007/044887 A3 | 4/2007 |
| WO | WO-2007/048037 A2 | 4/2007 |
| WO | WO-2007/048037 A3 | 4/2007 |
| WO | WO-2007/059816 A1 | 5/2007 |
| WO | WO-2007/068895 A1 | 6/2007 |
| WO | WO-2007/069092 A2 | 6/2007 |
| WO | WO-2007/069092 A3 | 6/2007 |
| WO | WO-2007/084181 A2 | 7/2007 |
| WO | WO-2007/084181 A3 | 7/2007 |
| WO | WO-2007/089445 A2 | 8/2007 |
| WO | WO-2007/089445 A3 | 8/2007 |
| WO | WO-2007/095338 A2 | 8/2007 |
| WO | WO-2007/108013 A2 | 9/2007 |
| WO | WO-2007/108013 A3 | 9/2007 |
| WO | WO-2007/109254 A2 | 9/2007 |
| WO | WO-2007/110205 A2 | 10/2007 |
| WO | WO-2007/110205 A3 | 10/2007 |
| WO | WO-2008/005828 A2 | 1/2008 |
| WO | WO-2008/005828 A3 | 1/2008 |
| WO | WO-2008/017963 A2 | 2/2008 |
| WO | WO-2008/017963 A3 | 2/2008 |
| WO | WO-2008/077077 A2 | 6/2008 |

(56) References Cited

FOREIGN PATENT DOCUMENTS

| | | |
|---|---|---|
| WO | WO-2008/077077 A3 | 6/2008 |
| WO | WO-2008/077546 A1 | 7/2008 |
| WO | WO-2008/100624 A2 | 8/2008 |
| WO | WO-2008/100624 A3 | 8/2008 |
| WO | WO-2008/132568 A2 | 11/2008 |
| WO | WO-2008/132568 A3 | 11/2008 |
| WO | WO-2009/007124 A1 | 1/2009 |
| WO | WO-2009/018386 A1 | 2/2009 |
| WO | WO-2009/021745 A1 | 2/2009 |
| WO | WO-2009/021754 A2 | 2/2009 |
| WO | WO-2009/021754 A3 | 2/2009 |
| WO | WO-2009/023843 A1 | 2/2009 |
| WO | WO-2009/030780 A2 | 3/2009 |
| WO | WO-2009/030780 A3 | 3/2009 |
| WO | WO-2009/032782 A2 | 3/2009 |
| WO | WO-2009/032782 A3 | 3/2009 |
| WO | WO-2009/037659 A2 | 3/2009 |
| WO | WO-2009/037659 A3 | 3/2009 |
| WO | WO-2009/059278 A1 | 5/2009 |
| WO | WO-2009/080251 A1 | 7/2009 |
| WO | WO-2009/080252 A1 | 7/2009 |
| WO | WO-2009/080253 A1 | 7/2009 |
| WO | WO-2009/080254 A1 | 7/2009 |
| WO | WO-2009/105671 A2 | 8/2009 |
| WO | WO-2009/105671 A3 | 8/2009 |
| WO | WO-2009/126944 A1 | 10/2009 |
| WO | WO-2010/034441 A1 | 4/2010 |
| WO | WO-2010/040508 A1 | 4/2010 |
| WO | WO-2010/040508 A8 | 4/2010 |
| WO | WO-2010/040508 A9 | 4/2010 |
| WO | WO2010/045193 A1 | 4/2010 |
| WO | WO-2010/065882 A1 | 6/2010 |
| WO | WO-2010/069532 A1 | 6/2010 |
| WO | 2010/087994 A2 | 8/2010 |
| WO | WO-2010/087994 A2 | 8/2010 |
| WO | WO-2010/087994 A3 | 8/2010 |
| WO | 2010/099536 A2 | 9/2010 |
| WO | 2010/099536 A3 | 9/2010 |
| WO | WO-2010/099536 A2 | 9/2010 |
| WO | WO-2010/099536 A3 | 9/2010 |
| WO | WO-2010/112193 A1 | 10/2010 |
| WO | WO-2010/112194 A1 | 10/2010 |
| WO | WO-2010/115552 A1 | 10/2010 |
| WO | WO-2010/115589 A1 | 10/2010 |
| WO | WO-2010/115589 A8 | 10/2010 |
| WO | WO-2010/118169 A2 | 10/2010 |
| WO | WO-2010/118169 A3 | 10/2010 |
| WO | WO-2010/136172 A1 | 12/2010 |
| WO | WO-2010/145792 A1 | 12/2010 |
| WO | WO-2010/145792 A8 | 12/2010 |
| WO | WO-2010/145793 A1 | 12/2010 |
| WO | WO-2011/028952 A1 | 3/2011 |
| WO | WO-2011/034605 A2 | 3/2011 |
| WO | WO-2011/034605 A3 | 3/2011 |
| WO | WO-2011/112983 A2 | 9/2011 |
| WO | WO-2011/112983 A3 | 9/2011 |
| WO | WO-2011/133886 A2 | 10/2011 |
| WO | WO-2012/006633 A1 | 1/2012 |
| WO | WO-2012/025525 A1 | 3/2012 |
| WO | WO-2012/025530 A1 | 3/2012 |
| WO | WO-2012/073985 A1 | 6/2012 |
| WO | WO-2012/085069 A2 | 6/2012 |
| WO | WO-2012/085069 A3 | 6/2012 |
| WO | WO-2012/085111 A1 | 6/2012 |
| WO | WO-2012/085113 A1 | 6/2012 |
| WO | WO-2012/116927 A1 | 9/2012 |
| WO | WO-2013/003555 A1 | 1/2013 |
| WO | WO-2013/006544 A1 | 1/2013 |
| WO | WO-2013/006544 A8 | 1/2013 |
| WO | WO-2013/026833 A1 | 2/2013 |
| WO | WO-2013/092716 A1 | 6/2013 |
| WO | WO-2013/119966 A2 | 8/2013 |
| WO | WO-2013/174873 A1 | 11/2013 |
| WO | WO-2014/001326 A1 | 1/2014 |
| WO | WO-2010/035012 A1 | 4/2016 |
| WO | WO-2016/055432 A2 | 4/2016 |
| WO | WO-2016/055432 A3 | 4/2016 |

OTHER PUBLICATIONS

Brekke et al. Immunologist 1994, 2:125-130 (Year: 1994).*
Bolscher et al. "Sortase A as a Tool for High-Yield Histatin Cyclization," *The FASEB Journal* 25(8):2650-2658, (Aug. 2011; e-published on Apr. 27, 2011).
Brorson et al., "Mutational Analysis of Avidity and Fine Specificity of Anti-Levan Antibodies," *J. Immunol.* 163:6694-6701, (1994).
Brummell et al. "Probing the Combining Site of an Anti-Carbohydrate Antibody by Saturation-Mutagenesis: Role of the Heavy-Chain CDR3 Residues," *Biochemistry* 32(4):1180-1187, (1993).
Burks et al. "In Vitro Scanning Saturation Mutagenesis of an Antibody Binding Pocket," *PNAS* 94(2):412-417, (1997).
Chames et al. "Bispecific Antibodies for Cancer Therapy", *Current Opinion in Drug Discovery & Developments* 12(2):276-283, (2009).
Chen et al. "Improved Variants of SrtA for Site-Specific Conjugation on Antibodies and Proteins with High Efficiency," *Scientific Reports* 6:31899, pp. 1-12, (2016, e-published on Aug. 18, 2016).
Coleman. "Effects of Amino Acid Sequence Changes on Antibody-Antigen Interactions," *Research in Immunol.* 145(1):33-36, (1994).
Dufner et al. "Harnessing Phage and Ribosome Display for Antibody Optimization," *Trends Biotechol.* 24(11):523-529, (2006).
Goldenberg et al. "Multifunctional Antibodies by the Dock-and-Lock Method for Improved Cancer Imaging and Therapy by Pretargeting," *J. Nuc. Med.* 49(1):158-163, (Jan. 2008).
Hayashi et al. "Application of L-DNA as a Molecular Tag," *Nucl. Acids Symp. Ser.* 49:261-262, (2005).
Hudson et al. "Engineered Antibodies," *Nat. Med.* 9(1):129-134, (Jan. 2003).
Jang et al., "The Structural Basis for DNA Binding by an Anti-DNA Autoantibody," *Mol. Immunol.* 35(18):1207-1217 (1998).
Kobayashi et al. "Tryptophan H33 Plays an Important Role in Pyrimidine (6-4) Pyrimidone Photoproduct Binding by a High-Affinity Antibody," *Protein Engineering* 12(10):879-844, (1999).
Kontermann et al. "Dual Targeting Strategies with Bispecific Antibodies," *MABS Landes Bioscience* 4(2):182-197, (Mar./Apr. 2012).
Kostelny et al. "Formation of a Bispecific Antibody by the Use of Leucine Zippers," *J. Immunol.* 148:1547-1553, (Mar. 1, 1992).
Levary et al. "Protein-Protein Fusion Catalyzed by Sortase A," *PLOS One* 6:e18342.1-e18342.6, (2011). Supplementary material, eight pages.
Marvin et al. "Recombinant Approaches to IgG-like Bispecific Antibodies," *Acta Pharmacol. Sin.* 26(6):649-658, (Jun. 2005).
Müller et al. "A Dimeric Bispecific Miniantibody Combines Two Specificities with Avidity," *FEBS Lett.* 432:45-49, (1998).
Pack et al. "Miniantibodies: Use of Amphipathic Helices to Produce Functional, Flexibly Linked Dimeric Fv Fragments with High Avidity in *Escherichia Coli,*" *Biochem.* 31(6):1579-1584, (Feb. 18, 1992).
Sakamoto et al. "Enzyme-Mediated Site-Specific Antibody-Protein Modification Using a ZZ Domain as a Linker," *BioConjugate Chem.* 21:2227-2233, (2010, e-pub. Nov. 11, 2010).
Strijbis et al. "Protein Ligation in Living Cells Using Sortase" *Traffic* 13(6):780-789, (Jun. 2012, e-published on Mar. 23, 2012).
Strop et al. "Generating Bispecific Human IgG1 and IgG2 Antibodies from Any Antibody Pair," *Journal of Molecular Biology* 420(3):204-219, (2012).
Ta et al. "Enzymatic Single-Chain Antibody Tagging a Universal Approach to Targeted Molecular Imaging and Cell Homing in Cardiovascular Disease," *Circulation Research* 109(4):365-373, (Aug. 5, 2011).
Wagner et al. "Bispecific Antibody Generated with Sortase and Click Chemistry has Broad Antiinfluenza Virus Activity," *Proc. Natl. Acad. Sci. USA* 111(47):16820-16825, (Nov. 25, 2014).
Witte et al. "Preparation of Unnatural N-to-N and C-to-C Protein Fusions", *Proceedings of the National Academy of Sciences of the United States of America* 109(30):11993-11998, (Jul. 24, 2012).

(56) References Cited

OTHER PUBLICATIONS

International Search Report dated Aug. 5, 2014, for PCT Patent Application No. PCT/EP2013/063258, filed on Jun. 25, 2013, seven pages.
International Search Report dated Aug. 6, 2013, PCT Patent Application No. PCT/EP2013/063260, filed on Jun. 25, 2013, seven pages.
International Search Report dated Nov. 4, 2013, for PCT Application No. PCT/EP2013/068910, filed on Sep. 12, 2013, five pages.
Written Opinion of the International Searching Authority dated Nov. 4, 2013, for PCT Application No. PCT/EP2013/068910, filed on Sep. 12, 2013, six pages.
Written Opinion of the International Searching Authority dated Aug. 5, 2014, for PCT Patent Application No. PCT/EP2013/063258, filed on Jun. 25, 2013, seven pages.
Written Opinion of the International Searching Authority dated Aug. 6, 2013, PCT Patent Application No. PCT/EP2013/063260, filed on Jun. 25, 2013, eight pages.
Anthony, R.M. et al. (2008). "Recapitulation of IVIG anti-inflammatory activity with a recombinant IgG Fc," Science 320:373-376.
Armour, et al. (1999). "Recombinant human IgG molecules lacking Fcgamma receptor I binding and monocyte triggering activities," Eur. J. Immunol. 29:2613-2624.
Burton (1985). "Immunoglobulin G: functional sites," Mol. Immunol. 22:161-206.
Capel, et al. (1994). "Heterogeneity of human IgG Fc receptors," Immunomethods 4:25-34.
Carter, J.P. (2006). "Potent antibody therapeutics by design," Nature Reviews Immunology 6:343-357.
Chan et al. (2010). "Therapeutic antibodies for autoimmunity and inflammation," Nature Reviews Immunology 10:301-316.
Charlton, Methods in Molecular Biology 248 (2003) 245-254 (B.K.C. Lo, (ed.), Humana Press, Totowa, NJ.
Chin et al. (2002). "Addition of p-azido-L-phenylalanine to the genetic code of Escherichia coli," J. Am. Chem. Soc. 124:9026-9027.
Chin (2002). "In vivo photocrosslinking with unnatural amino acid mutagenesis," ChemBioChem 11:1135-1137.
Chin et al. (2002). "Addition of a photocrosslinking amino acid to the genetic code of Escherichia coli," PNAS 99:11020-11024.
Clancy et al. (2010). "Sortase transpeptidases: insights into mechanism, substrate specificity, and inhibition," Peptide Science 94:385-396.
Daëron (1997). "Fc receptor biology," Annu. Rev. Immunol. 15:203-234.
Dall'Acqua et al. (1998). "Contribution of domain interface residues to the stability of antibody CH3 domain homodimers," Biochem. 37:9266-9273.
De Haas, et al. (1995). "Fey receptors of phagocytes," J. Lab. Clin. Med. 126:330-341.
Edelman, et al. (1969). "The covalent structure of an entire gammaG immunoglobulin molecule," PNAS 63:78-85.
Ellman, et al. (1991). "Biosynthetic method for introducing unnatural amino acids site-specifically into proteins," Meth. Enzym. 202:301-336.
Extended European Search Report dated Nov. 13, 2012, for EP Application No. 12 173 876.9, filed on Jun. 27, 2012, six pages.
Friend, et al (1999). "Phase I study of an engineered aglycosylated humanized CD3 antibody in renal transplant rejection," Transplantation 68:1632-1637.
Gerngross (2004). "Advances in the production of human therapeutic proteins in yeasts and filamentous fungi," Nat. Biotech. 22:1409-1414.
Guyer, et al. (1976). "Immunoglobulin binding by mouse intestinal epithelial cell receptors," J. Immunol. 117: 587-593.
Huber, et al. (1976). "Crystallographic structure studies of an IgG molecule and an Fc fragment," Nature 264:415-420.

Ilangovan, H. et al. (2001). "Structure of sortase, the transpeptidase that anchors proteins to the cell wall of Staphylococcus aureus," PNAS 98:6056-6061.
International Search Report dated Aug. 13, 2013, for PCT Patent Application No. PCT/EP2013/063259, filed on Jun. 25, 2013, six pages.
Jefferis, et al. (2002). "Interaction sites on human IgG-Fc for FcgammaR: current models," Immunol. Lett. 82:57-65.
Jiang, X.-R., et al. (2011). "Advances in the assessment and control of the effector functions of therapeutic antibodies," Nature Reviews Drug Discovery 10:101-111.
Kim, et al., (1994). "Localization of the site of the murine IgG1 molecule that is involved in binding to the murine intestinal Fc receptor," Eur. J. Immunol. 24:2429-2434.
Kinet (1991). "Fc Receptors," Annu. Rev. Immunol. 9:457-492.
Levary et al. (2011). "Protein-Protein fusion catalyzed by sortase A," PLOS One 6:e18342.1-e18342.6.
Li, et al. (2006). "Optimization of humanized IgGs in glycoengineered Pichia pastoris," Nat. Biotech. 24:210-215.
Madej et al. (2011). "Engineering of an anti-epidermal growth factor receptor antibody to single chain format and labeling by sortase A-mediated protein ligation," Biotech. & Bioengineering 109(6):1461-1470.
Mather, J.P. (1980). "Establishment and characterization of two distinct mouse testicular epithelial cell lines," Biol. Reprod. 23:243-252.
Mather, J.P., et al. (1982). "Culture of testicular cells in hormone-supplemented serum-free medium," Annals N.Y. Acad. Sci. 383:44-68.
Mohlmann et al. (2011). "In vitro sortagging of an antibody fab fragment: overcoming unproductive reactions of sortase with water and lysine side chains," Chembiochem. 12(11):1774-1780.
Noren, et al. (1989). "A general method for site-specific incorporation of unnatural amino acids into proteins," Science 244:182-188.
Popp (2011). "Making and breaking peptide bonds: protein engineering using sortase," Angew. Chem. Int. Ed. 50:5024-5032.
Presta (2008). "Molecular engineering and design of therapeutic antibodies," Current Opinion in Immunology 20:460-470.
Ravetch et al. (1991). "Fc receptors," Annu. Rev. Immunol. 9:457-492.
Routledge, et al. (1995). "The effect of aglycosylation on the immunogenicity of a humanized therapeutic CD3 monoclonal antibody," Transplantation 60:847-853.
Roux, et al. (1998). "Comparisons of the ability of human IgG3 hinge mutants, IgM, IgE, and IgA2, to form small immune complexes: a role for flexibility and geometry," J. Immunol. 161:4083-4090.
Shields, et al. (2001). "High resolution mapping of the binding site on human IgG1 for Fc gamma RI, Fc gamma RII, Fc gamma RIII, and FcRn and design of IgG1 variants with improved binding to the Fc gamma R," J. Biol. Chem. 276:6591-6604.
Sondermann, et al. (2000). "The 3.2-A crystal structure of the human IgG1 Fc fragment-Fc gammaRIII complex," Nature 406:267-273.
Swee et al. (2013). "Sortase-mediated modification of αDEC205 affords optimization of antigen presentation and immunization against a set of viral epitopes," PNAS 110:1428-1433.
Thies, et al. (1999). "Folding and association of the antibody domain CH3: prolyl isomerization proceeds dimerization," J. Mol. Biol. 293:67-79.
Ton-That et al. (1999). "Purification and characterization of sortase, the transpeptidase that cleaves surface proteins of Staphylococcus aureus at the LPXTG motif," PNAS 96:12424-12429.
Tsukiji (2009). "Sortase-mediated ligation: a gift from Gram-positive bacteria to protein engineering," ChemBioChem 10:787-798.
Urlaub et al. (1980). "Isolation of Chinese hamster cell mutants deficient in dihydrofolate reductase activity," PNAS 77:42164220.
Wang et al. (2002). "Expanding the genetic code,"Chem. Comm. 7:1-11.
Ward et al. (1995). "The effector functions of immunoglobulins: implications for therapy," Ther. Immunol. 2:77-94.

(56) References Cited

OTHER PUBLICATIONS

Written Opinion of the International Searching Authority dated Aug. 13, 2013, for PCT Patent Application No. PCT/EP2013/063259, filed on Jun. 25, 2013, six pages.
Written Opinion (Second) of the International Searching Authority dated Jul. 11, 2014, for PCT Patent Application No. PCT/EP2013/063259, filed on Jun. 25, 2013, seven pages.
Yazaki, P. and Wu, A.M., Methods in Molecular Biology, vol. 248, Lo, B.K.C. (ed.), Humana Press, Totowa, NJ (2004), pp. 255-268.
U.S. Appl. No. 14/579,165, filed Dec. 22, 2014, by Heindl et al.
U.S. Appl. No. 14/579,218, filed Dec. 22, 2014, by Fenn et al.
Levary et al., "Protein-Protein Fusion Catalyzed by Sortase A" PLoS ONE 6(4 Suppl e18342):1-6 ( 2011).
Madej et al., "Engineering of an Anti-Epidermal Growth Factor Receptor Antibody to Single Chain format and Labeling by Sortase A-Mediated Protein Ligation" Biotechnology and Bioengineering 109(6):1461-1470 ( 2012).
Moehlmann et al., "In vitro Sortagging of an Antibody Fab Fragment: Overcoming Unproductive Reactions of Sortase with Water and Lysine Side Chains" ChemBioChem 12:1774-1780 ( 2011).
Swee, Lee Kim et al., "Sortase-mediated modification of αDEC205 affords optimization of antigen presentation and immunization against a set of viral epitopes" PNAS 110:1428-1433 ( 2013).
Adams et al. "Highly Specific In Vivo Tumor Targeting by Monovalent and Divalent Forms of 741F8 Anti-c-erbB-2 Single-Chain Fv," Cancer Res. 53:4026-4034, (1993).
Aggarwal et al. "Fibroblast Activation Protein Peptide Substrates Identified from Human Collagen I Derived Gelatin Cleavage Sites," Biochemistry 47(3):1076-1086, (Jan. 22, 2008).
Alt et al. "Novel Tetravalent and Bispecific IgG-Like Antibody Molecules Combining Single-Chain Diabodies With the Immunoglobulin γ1 Fc or CH3 Region," FEBS Lett. 454(1-2):90-94, (Jul. 2, 1999).
An et al. "Targeted Drug Delivery to Mesothelioma Cells Using Functionally Selected Internalizing Human Single-Chain Antibodies," Mol. Cancer Ther. 7:569-578, (2008).
Anonymous. "Production in Yeasts of Stable Antibody Fragments," Expert Opinion on Therapeutic Patents 7(2):179-183, (1997).
Arié et al. "Chaperone Function of FkpA, a Heat Shock Prolyl Isomerase, in the Periplasm of Escherichia coli," Mol. Microbiol. 39(1):199-210, (2001).
Arndt et al. "Factors influencing the dimer to monomer transition of an antibody single-chain Fv fragment," Biochemistry 37(37):12918-12926, (1998).
Arndt, K.M. et al. "Helix-Stabilized Fv (hsFv) Antibody Fragments: Substituting the Constant Domains of a Fab Fragment for a Heterodimeric Coiled-Coil Domain," J. Mol. Biology 312(1):221-228, (Sep. 7, 2001).
Atwell et al. "Stable Heterodimers From Remodeling the Domain Interface of a Homodimer Using a Phage Display Library," J. Mol. Biol. 270 (1):26-35, (1997).
Ausubel et al. Short Protocols in Molecular Biology, Greene Publishing and Wiley Interscience, New York, New York, (Table of Contents), (1987).
Avgeris et al. "Kallikrein-Related Peptidase Genes as Promising Biomarkers for Prognosis and Monitoring of Human Malignancies," Biol. Chem. 391(5):505-511, (May 2010).
Bachman. "Derivations and Genotypes of Some Mutant Derivatives of Esherichia coli K-12," Chapter 72 in Escherichia coli and Samonella Typimurium Cellular and Molecular Biology, vol. 2, American Society for Microbiology, Washington D.C., pp. 1190-1219, (1987).
Backer et al. "Molecular Vehicles for Targeted Drug Delivery," Bioconjugate Chem. 13:462-467, (2002).
Baldwin et al. "Monoclonal Antibodies in Cancer Treatment," Lancet 60:603-606, (1986).
Bao et al., "HER2-Mediated Upregulation of MMP-1 Is Involved in Gastric Cancer Cell Invasion," Arch Biochem Biophys 499(1-2):49-55, (Jul. 2010).

Barbin et al. "Influence of Variable N-Glycosylation on the Cytolytic Potential of Chimeric CD19 Antibodies," J. Immunother. 29(2):122-133, (Mar.-Apr. 2006).
Barnes et al. "Methods for Growth of Cultured Cells in Serum-Free Medium," Anal. Biochem. 102:255-270, (1980).
Barnes et al., "Advances in Animal Cell Recombinant Protein Production: GS-NS0 Expression System," Cytotechnology 32 (2):109-23 (Feb. 2000).
Barnes et al., "Characterization of the Stability of Recombinant Protein Production in the GS-NS0 Expression System," Biotechnol Bioeng. 73(4):261-70, (May 2001).
Bass et al. "Hormone Phage: An Enrichment Method for Variant Proteins With Altered Binding Properties," Proteins 8:309-314, (1990).
Behrens. "Synthesis of Achiral Linker Reagents for Direct Labelling of Oligonucleotides on Solid Supports," Nucleosides & Nucleotides 18:291-305, (1999).
Bendig. "Humanization of Rodent Monoclonal Antibodies by CDR Grafting," Methods: A companion to Methods in Enzymology 8:83-93, (1995).
Bera et al. "A Bivalent Disulfide-Stabilized Fv With Improved Antigen Binding to erbB2," J. Mol. Biol. 281(3):475-483, (Aug. 21, 1998).
Bird et al. "Single-chain antigen-binding proteins," Science 242:423-426, (1988).
Bird et al. "Single-Chain Antigen-Binding Proteins," Science 244(4903):409, Erratum, (Apr. 28, 1989).
Boado et al. "IgG-single Chain Fv Fusion Protein Therapeutic for Alzheimer's disease: Expression in CHO cells and Pharmacokinetics and Brain Delivery in the Rhesus Monkey," Biotechnology and Bioengineering 105(3):627-635, (Feb. 15, 2010).
Boerner et al. "Production of Antigen-Specific Human Monoclonal Antibodies From In Vitro-Primed Human Splenocytes," J. Immunol. 147(1):86-95, (Jul. 1991).
Booy et al. (Mar.-Apr. 2006, e-pub. Mar. 24, 2006). "Monoclonal and Bispecific Antibodies as Novel Therapeutics," Arch. Immunol. Ther. Exp. 54:85-101.
Bordusa. In Highlights in Bioorganic Chemistry, Schmuck, C. and Wennemers, H., (eds.), Wiley VCH, Weinheim, pp. 389-403, (2004).
Borgström et al. "Complete Inhibition of Angiogenesis and Growth of Microtumors by Anti-Vascular Endothelial Growth Factor Neutralizing Antibody: Novel Concepts of Angiostatic Therapy from Intravital Videomicroscopy," Cancer Research 56:4032-4039, (1996).
Bothmann et al. "The Periplasmic Escherichia coli Peptidylprolyl cis,trans-Isomerase FkpA. I. Increased Functional Expression of Antibody Fragments With and Without cis-Prolines," J. Biol. Chem. 275(22):17100-17105, (Jun. 2, 2000).
Brennan et al. "Preparation of Bispecific Antibodies by Chemical Recombination of Monoclonal Immunoglobulin G1 fragments," Science 229:81-83, (1985).
Briggs et al. "Cystatin E/M Suppresses Legumain Activity and Invasion of Human Melanoma," BMC Cancer 10(17):1-13, (Jan. 2010).
Brinkmann et al. "A Recombinant Immunotoxin Containing a Disulfide-Stabilized Fv Fragment," PNAS 90(16):7538-7542, (1993).
Brinkmann. "Disulfide-stabilized Fv fragments," Chapter 14 in Antibody Engineering, Kontermaan et al. eds., vol. 2, Springer-Verlag, Berlin Heidelberg, Germany, pp. 181-189, (Apr. 30, 2010).
Brüggemann et al. "Comparison of the Effector Functions of Human Immunoglobulins Using a Matched Set of Chimeric Antibodies," J Exp Med. 166(5):1351-61, (Nov. 1987).
Brüggemann et al. "Designer Mice: The Production of Human Antibody Repertoires in Transgenic Animals," Year in Immuno. 7:33-40, (1993).
Brunhouse et al. "Isotypes of IgG: Comparison of the Primary Structures of Three Pairs of Isotypes Which Differ in Their Ability to Activate Complement," Mol Immunol. 16(11): 907-917 (Nov. 1979).
Budtschanow et al. "System of Humoral Immunity Antibodies (Theme 2)," Guidance Manual for General Immunology, Twer (2008) p. 3, English Translation, 3 pages, (5 pages both English Equivalent and Russian Reference.).

(56) References Cited

OTHER PUBLICATIONS

Burgess et al. "Possible Dissociation of the Heparin-Binding and Mitogenic Activities of Heparin-Binding (Acidic Fibroblast) Growth Factor-1 From Its Receptor-Binding Activities by Site-Directed Mutagenesis of a Single Lysine Residue," *Journal of Cell Biology* 111:2129-2138, (Nov. 1990).
Burton et al. "The C1q Receptor Site on Immunoglobulin G," *Nature* 288(5789):338-344, (Nov. 27, 1980).
Cao et al. "Bispecific Antibody Conjugates in Therapeutics," *Advanced Drug Delivery Reviews* 55:171-197, (2003).
Carlsson et al. "Protein Thiolation and Reversible Protein-Protein Conjugation. N-Succinimidyl 3-(2-pyridyldithio)Propionate, a New Heterobifunctional Reagent," *Biochem. J.* 173:723-737, (Sep. 1, 1978).
Carmichael et al. "Evaluation of a Tetrazolium-Based Semiautomated Colorimetric Assay: Assessment of Chemosensitivity Testing," *Cancer Res.* 47:936-942, (1987).
Caron et al. "Engineered Humanized Dimeric Forms of Igg Are More Effective Antibodies," *J. Exp. Med.* 176(4):1191-1195, (Oct. 1, 1992).
Carro et al. "Serum Insulin-Like Growth Factor I Regulates Brain Amyloid-B Levels," *Nature Medicine* 8(12):1390-1397, (2002, e-pub. Nov. 4, 2002).
Carter et al. "High Level *Escherichia coli* Expression and Production of a Bivalent Humanized Antibody Fragment," *Bio/Technology* 10:163-167, (1992).
Carter et al. "Humanization of an Anti-P185$^{HER2}$ Antibody for Human Cancer Therapy," *Proc. Natl. Acad. Sci. USA.* 89(10):4285-4289, (May 1992).
Carter. "Bispecific Human IgG by Design," *Immunol. Methods* 248:7-15. (2001).
Chan et al. "Variable Region Domain Exchange in Human IgGs Promotes Antibody Complex Formation with Accompanying Structural Changes and Altered Effector Functions," *Molecular Immunology* 41(5):527-538, (2004).
Chang et al. "A General Method for Facilitating Heterodimeric Pairing Between Two Proteins: Application to Expression of α and p T-cell Receptor Extracellular Segments," *Proc. Natl'l Acad. Sci.* 91:11408-12, (Nov. 1994).
Chari et al. "Immunoconjugates containing novel maytansinoids: promising anticancer drugs," *Cancer Res.* 52:127-131, (1992).
Chen et al. "Selection and Analysis of an Optimized Anti-VEGF Antibody: Crystal Structure of an Affinity-Matured Fab in Complex With Antigen," *J. Mol. Biol.* 293:865-881, (Nov. 5, 1999).
Chen et al. "Chaperone Activity of DsbC," *J. Biol. Chem* 274(28):19601-19605, (Jul. 9, 1999).
Cheong et al. "Affinity enhancement of bispecific antibody against two different epitopes in the same antigen," *Biochem. Biophys. Res. Commun.* 173:795-800, (1990).
Chernaia. "[Cathepsin L from human brain tumor. Purification and contents]." *Ukr Biokhim Zh.* 70(5):97-103, (Sep.-Oct. 1998). (English Translation of Abstract.).
Chitnis et al. "The Type 1 Insulin-Like Growth Factor Receptor Pathway," *Clin. Cancer Res.* 14(20):6364-6370 (Oct. 16, 2008).
Chothia et al. "Canonical Structures for the Hypervariable Regions of Immunoglobulins," *J. Mol. Biol.* 196:901-917, (1987).
Chow et al. "Studies on the Subsite Specificity of Rat Nardilysin (N-Arginine Dibasic Convertase)," *J. Biol. Chem.* 275(26):19545-19551, (Jun. 30, 2000).
Chung et al. "Development of a Novel Albumin-Binding Prodrug That Is Cleaved by Urokinase-Type-Plasminogen Activator (uPA)," *Bioorg Med Chem Lett.* 16(19):5157-5163, (Oct. 1, 2006).
Clackson et al. "Making Antibody Fragments Using Phage Display Libraries," *Nature* 352:624-628, (1991).
Clynes et al. "Fc Receptors are Required in Passive and Active Immunity to Melanoma," *Proc. Natl. Acad. Sci. USA* 95:852-858, (Jan. 1998).
Cocuzza. "A Phosphoramidite Reagent for Automated Solid Phase Synthesis of 5'-biotinylated Oligonucleotides," *Tetrahedron Letters* 30:8287-8290, (1989).

Cohen et al., "Nonchromosomal Antibiotic Resistance in Bacteria: Genetic Transformation of *Escherichia coli* by R-Factor DNA," *Proc. Natl. Acad. Sci. USA* 69(8):2110-2114 (Aug. 1972).
Cole et al. "The EBV-Hybridoma Technique and Its Application to Human Lung Cancer," in *Monoclonal Antibodies and Cancer Therapy*, New York: Alan R. Liss, Inc., pp. 77-96 (1985).
Coloma and Morrison. "Design and production of novel tetravalent bispecific antibodies," *Nature Biotechnology* 15(2):159-163, (Feb. 1997).
Cordingley et al. "Substrate Requirements of Human Rhinovirus 3C Protease for Peptide Cleavage In Vitro," *J. Biol. Chem.* 265(16):9062-9065, (1990).
Cortesio et al. "Calpain 2 and PTP1B Function in a Novel Pathway With Src to Regulate Invadopodia Dynamics and Breast Cancer Cell Invasion," *J. Cell Biol.* 180(5):957-971, (Mar. 10, 2008).
Coxon et al. "Combined Treatment of Angiopoietin and VEGF Pathway Antagonists Enhances Antitumor Activity in Preclinical Models of Colon Carcinoma," *99th AACR Annual Meeting*, Abstract #1113, (Apr. 2008).
Crawford et al. "Matrix Metalloproteinase-7 Is Expressed by Pancreatic Cancer Precursors and Regulates Acinar-To-Ductal Metaplasia in Exocrine Pancreas," *J. Clin. Invest.* 109(11):1437-1444, (Jun. 2002).
Cruse et al. *Illustrated Dictionary of Immunology* 2nd ed., CRC Press, pp. 37, 316-317, (2003).
Cudic et al. "Extracellular Proteases as Targets for Drug Development," *Curr. Protein Pept Sci* 10(4):297-307, (Aug. 2009).
Cullen et al., "Granzymes in Cancer and Immunity," *Cell Death Differ* 17(4):616-623, (Apr. 2010).
Davies et al. "'Camelising' Human Antibody Fragments: NMR Studies on VH Domains," *Febs Letter* 339:285-290, (1994).
Davies et al. "Expression of GnTIII in a Recombinant Anti-CD20 CHO Production Cell Line: Expression of Antibodies With Altered Glycoforms Leads to an Increase in ADCC Through Higher Affinity for FcγRIII," *Biotechnol. Bioeng.* 74:288-294, (2001).
Davis et al. "SEEDbodies: Fusion Proteins Based on Strand-Exchange Engineered Domain (SEED) $C_H3$ Heterodimers in an Fc Analogue Platform for Asymmetric Binders or Immunofusions and Bispecific Antibodies," *Protein Engineering Design & Selection* 23(4):195-202, (2010, e-pub. Feb. 4, 2010).
De Graaf et al. "Nonnatural Amino Acids for Site Specific Protein Conjugation," *Bioconjug. Chem.* 20:1281-1295, (2009).
Dervan. "Molecular Recognition of DNA by Small Molecules," *Biooig. Med. Chem.* 9:2215-2235, (2001).
Deyev et al. "Modern Technologies for Creating synthetic Antibodies for Clinical Application," *Acta Naturae* 1:32-50, (2009).
Deyev. "Multivalency: the Hallmark of Antibodies Used for Optimization of Tumor Targeting by Design," *Bioessays* 30(9):904-918, (2008).
Dimmock et al. "Valency of Antibody Binding to Virions and Its Determination by Surface Plasmon Resonance," *Rev. Med. Virol.*, 14:123-135, (2004).
Ding et al. "Gold Nanorods Coated with Multilayer Polyelectrolyte as Contrast Agents for Multimodal Imaging," *J. Phys. Chem. C* 111:12552-12557, (2007).
Donaldson et al. "Design and development of masked therapeutic antibodies to limit off-target effects: Application to anti-EGFR antibodies," *Cancer Biology & Therapy* 8(22):2145-2150, (Nov. 15, 2009).
Dooley et al. "Antibody Repertoire Development in Cartilaginous Fish," *Dev. Comp. Immunol.* 30(1-2):43-56, (2006).
Doronina et al. "Development of Potent Monoclonal Antibody Auristatin Conjugates for Cancer Therapy," *Nat. Biotechnol.* 21(7):778-784, (Jul. 2, 2003, e-pub. Jun. 1, 2003).
Dubowchik et al. "Doxorubicin immunoconjugates containing bivalent, lysosomally-cleavable dipeptide linkages," *Bioorg. & Med. Chem. Letters* 12:1529-1532, (2002).
Durocher et al. "High-level and High-Throughput Recombinant Protein Production by Transient Transfection of Suspension-Growing Human 293-EBNA1 Cells," *Nucleic Acids Research* 30(2 e9):1-9, (2002).

(56) References Cited

OTHER PUBLICATIONS

Eaton et al. "Construction and Characterization of an Active Factor VIII Variant Lacking the Central One-Third of the Molecule," *Biochemistry* 25(26):8343-8347, (Dec. 30, 1986).
Els Conrath et al. "Camel Single-Domain Antibodies as Modular Building Units in Bispecific and Bivalent Antibody Constructs," *Journal of Biological Chemistry* 276(19):7346-7350, (Mar. 9, 2001).
Fischer et al. "Bispecific Antibodies: Molecules That Enable Novel Therapeutic Strategies," *Pathobiology* 74:3-14, (2007).
Flatman et al. "Process Analytics for Purification of Monoclonal Antibodies," *J. Chromatogr B* 848:79-87, (2007).
Fraker et al. "Protein and Cell Membrane Iodinations With a Sparingly Soluble Chloroamide, 1,3,4,6-Tetrachloro-3a,6a-Diphenylglycoluril," *Biochem. Biophys. Res. Commun.* 80(4):49-57, (Feb. 28, 1978).
Frese. "Formylglycine aldehyde Tag—protein engineering through a novel post-translational modification," *ChemBioChem* 10:425-427, (2009).
Gadgil et al. "Identification of Cysteinylation of a Free Cysteine in the Fab Region of a Recombinant Monoclonal IgG1 Antibody Using Iys-C Limited Proteolysis Coupled With LC/MS Analysis," *Analytical biochem.* 2006:355:185-174, (2006).
Galamb et al. "Inflammation, Adenoma and Cancer: Objective Classification of Colon Biopsy Specimens With Gene Expression Signature," *Dis Markers* 25(1):1-16, (2008).
Gautier et al. "An Engineered Protein Tag for Multiprotein Labeling in Living Cells," *Chem. Biol.* 15:128-136, (2008).
Gazzano-Santoro et al. "A Non-Radiactive Complement-Dependent Cytotoxicity Assay for Anti-CD20 Monoclonal Antibody," *J. Immunol. Methods* 202:163, (1996).
Geisse et al. "Eukaryotic Expression Systems: A Comparison," *Protein Expression and Purification* 8:271-282, (1996).
Geoghegan et al. "Site-Directed Conjugation of Nonpeptide Groups to Peptides and Proteins via Periodate Oxidation of a 2-Amino Alcohol. Application Modification at N Terminator Serine," *Bioconjugate Chem.* 3(2):138-146, (1992).
Gerspach et al. "Target-Selective Activation of a TNF Prodrug by Urokinase-Type Plasminogen Activator (uPA) Mediated Proteolytic Processing at the Cell Surface," *Cancer Immunol. Immunother* 55:1590-1600 (2006).
Gold et al. "A Novel Bispecific, Trivalent Antibody Construct for Targeting Pancreatic Carcinoma," *Cancer Res.* 68(12):4819-4826, (2008).
Goldenberg et al. "Bi-Specific Antibodies that Bind Specific Target Tissue and Targeted Conjugates," *Derwent Information Ltd.*, 12 pages, (2012).
Goodman et al. Chapter 6 in *Basic and Clinical Immunology*, 8th edition, Appleton & Lange, Norwalk, CT, pp. 66-79, (1994).
Graham et al. "A New Technique for the Assay of Infectivity of Human Adenovirus 5 DNA," *Virology* 52 (2):456-467, (1973).
Graham et al. "Characteristics of a Human Cell Line Transformed by DNA From Human Adenovirus Type 5," *J. Gen Virol.* 36:59-72, (1977).
Greenwood et al. "Structural Motifs Involved in Human IgG Antibody Effector Functions,". *Eur. J. Immunology* 23(5):1098-1104, (May 1993).
Grönwall C. et al. "Generation of Affibody Ligands Binding Interleukin-2 Receptor Alpha/CD25," *Biotechnol. Appl. Biochem.* 50(Pt. 2):97-112, (Jun. 2008).
Grote et al. "Bispecific Antibody Derivatives Based on Full-Length IgG Formats," Chapter 16 in *Methods in Molecular Biology* 901:247-263, (2012).
Gruber et al. "Efficient Tumor Cell Lysis Mediated by a Bispecific Single Chain Antibody Expressed in *Escherichia coli*," *J. Immunol.* 152:5368-5374, (1994).
Gunasekaran et al. "Enhancing Antibody Fc Heterodimer Formation Through Electrostatic Steering Effects: Applications to Bispecific Molecules and Monovalent IgG," *The Journal of Biological Chemistry* 285(25):19637-19646, (Jun. 18, 2010).

Guss et al. "Structure of the IgG-Binding Regions of Streptococcal Protein G," *EMBO J.* 5:1567-1575, (1986).
Hackenberger. "Chemoselective Ligation and Modification Strategies for Peptides and Proteins," *Angew. Chem. Int. Ed.* 47:10030-10074, (2008).
Ham et al. "Media and Growth Requirements," *Meth. Enzymol.* 58:44-93, (1979).
Hamers-Casterman et al. "Naturally Occurring Antibodies Devoid of Light Chains," *Nature* 363:446-448, (1993).
Hara et al. "Overproduction of Penicillin-Binding Protein 7 Suppresses Thermosensitive Growth Defect at Low Osmolarity Due to an spr Mutation of *Escherichia coli*," *Microbial Drug Resistance* 2:63-72, (1996).
Hartog et al. "The Insulin-Like Growth Factor 1 Receptor in Cancer: Old focus, New Future," European Journal of Cancer, Pergamon Press, Oxford, GB, 43(13):1895-1904, (Aug. 23, 2007).
Hatfield, K.J. et al. "Antiangiogenic Therapy in Acute Myelogenous Leukemia: Targeting of Vascular Endothelial Growth Factor and Interleukin 8 as Possible Antileukemic Strategies," *Curr. Cancer Drug Targets* 5(4):229-248, (2005).
Henry et al. "Clinical Implications of Fibroblast Activation Protein in Patients With Colon Cancer," *Clin Cancer Res.* 13(6):1736-1741, (Mar. 15, 2007).
Herberman. "Immunodiagnosis of Cancer", in *The Clinical Biochemistry of Cancer*, American Association of Clinical Chemists, Washington, D.C. pp. 347-364, (1979).
Hey et al. "Artificial, Non-Antibody Binding Proteins for Pharmaceutical and Industrial Applications," *Trends Biotechnol.* 23:514-522, (2005).
Hezareh et al. "Effector Function Activities of a Panel of Mutants of a Broadly Neutralizing Antibody against Human Immunodeficiency Virus Type 1," *Journal of Virology* 75(24):12161-12168, (Dec. 2001).
Hinman et al. "Preparation and Characterization of Monoclonal Antibody Conjugates of the Calicheamicins: A Novel and Potent Family of Antitumor Antibiotics," *Cancer Res.* 53:3336-3342, (1993).
Hollander. "Bispecific Antibodies for Cancer Therapy," *Immunotherapy* 1(2):211-222, (Mar. 2009).
Holliger et al. "Diabodies: Small Bivalent and Bispecific Antibody Fragments," *Proc. Natl. Acad. Sci. USA* 90:6444-6448, (1993).
Holliger et al. "Engineered Antibody Fragments and the Rise of Single Domains," *Nat Biotechnol.* 23(9):1126-1136, (Sep. 2005).
Holt et al. "Domain Antibodies: Proteins for Therapy," *Trends Biotechnol.* 21(11):484-490, (Nov. 2003).
Hoogenboom et al. "By-passing immunisation. Human antibodies from synthetic repertoires of germline $V_H$ gene segments rearranged in vitro," *J Mol Biol.* 227 (2):381-388, (Sep. 20, 1992).
Hoppe et al. "A Parallel Three Stranded Alpha-Helical Bundle at the Nucleation Site of Collagen Triple-Helix Formation," *FEBS Lett.* 344:191-195, (1994).
Hust et al. "Single Chain Fab (scFab) Fragment," *BMC Biotechnology* 7(14):1-15, (Mar. 8, 2007).
Huston et al. "Medical Applications of Single-Chain Antibodies," *Intern. Rev. Immunol.* 10(2-3):195-217, (1993).
Huston et al. "Protein engineering of antibody binding sites: recovery of specific activity in an anti-digoxin single-chain Fv analogue produced in *Escherichia coli*," *Proc. Natl. Acad. Sci. USA* 85:5879-5883, (1988).
Huynh et al. "Synthesis of Cholesteryl Supports and Phosphoramidites Containing a Novel Peptidyl Linker for Automated Synthesis of Triple-Helix Forming Oligonucleotides," *Nucleic Acids Symposium Series* 29 (Second International Symposium on Nucleic Acids Chemistry), pp. 19-20, (1993).
Ibragimova et al. "Stability of the β-Sheet of the WW domain: A Molecular Dynamics Simulation Study," *Biophysical Journal* 77:2191-2198, (Oct. 1999).
Idusogie et al. "Mapping of the C1q Binding Site on Rituxan, A Chimeric Antibody With a Human IgG1Fc," *The Journal of Immunology* 164:4178-4184, (2000).
Iyer. "Abasic Oligodeoxyribonucleoside Phosphorothioates: Synthesis and Evaluation as Anti-HIV-1 Agents," *Nucleic Acids Research* 18:2855-2859, (1990).

(56) References Cited

OTHER PUBLICATIONS

Jackman et al. "Development of a Two-part Strategy to Identify a Therapeutic Human Bispedfic Antibody That Inhibits IgE Receptor Signaling," *The Journal of Biological Chemistry* 285(27):20850-20859, (Jul. 2, 2010).
Jakobovits et al. "Analysis of Homozygous Mutant Chimeric Mice: Deletion of the Immunoglobulin Heavy-Chain Joining Region Blocks B-cell Development and Antibody Production," *Proc. Natl. Acad. Sci. USA* 90(6):2551-2555, (Mar. 15, 1993).
Jakobovits et al. "Germ-line Transmission and Expression of a Human-derived Yeast Artificial Chromosome," *Nature* 362:255-258, (Mar. 1993).
Janeway. "Immunotherapy by Peptdes?" *Nature* 341:482-483, (Oct. 12, 1989).
Jefferis et al. "IgG-Fc-Mediated Effector Functions: Molecular Definition of Interaction Sites for Effector Ligands and the Role of Glycosylation," *Immunol Rev.* 163:59-76, (1998).
Jeffrey et al. "Dipeptide-Based Highly Potent Doxorubicin Antibody Conjugates," *Bioorg. Med. Chem. Lett.* 16:358-362, (2006).
Jendreyko et al. "Simultaneous, Phenotypic Knockout of VEGF-R2 and Tie-2 With an Intradiabody Enhances Antiangiogenic Effects In Vivo," *Therapieoptimierung and Risikostratifizierung*, Scripps Research Institute, 218:143-151, (2006).
Jia et al. "A Novel Trifunctional IgG-Like Bispecific Antibody to Inhibit HIV-1 Infection and Enhance Lysis of HIV by Targeting Activation of Complement," *Virology Journal* 7(142):1-4, (Jun. 29, 2010).
Johnson et al. "Construction of Single-Chain Fv Derivatives Monoclonal Antibodies and their Production in *Escherichia coli*," *Methods Enzymol.* 203:88-98, (1991).
Johnson et al. "Kabat Database and Its Applications: 30 Years After the First Variability Plot," *Nucleic Acids Research* 28(1):214-218, (2000).
Johnson et al. "The Kabat Database and a Bioinformatics Example," Chapter 2 in *Methods in Molecular Biology*, Lo, B.K.C, Humana Press, Totawa, N.J., 248:11-25, (2003).
Joly et al. "Overexpression of *Escherichia coli* Oxidoreductases Increases Recombinant Insulin-like Growth Factor-I Accumulation," *Proc. Natl. Acad. Sci. USA* 95-2773-2777, (Mar. 1998).
Jones et al. "Replacing the Complementarity-Determining Regions in a Human Antibody With Those From a Mouse," *Nature* 321:522-525, (May 29, 1986).
Kabat et al. "Evolutionary and Structural Influences on Light Chain Constant ($C_L$) Region of Human and Mouse Immunoglobulins," *Proc. Natl. Acad. Sci. USA* 72(7):2785-2788, (Jul. 1975).
Kabat et al. *Sequences of Proteins of Immunological Interest* (Table of Contents and Introduction), 5th edition, Bethesda, MD: Public Health Service, NIH, vol. 1, (1991).
Karadag et al. "ADAM-9 (MDC-9/meltrin-γ), A Member of the A Disintegrin and Metalloproteinase Family, Regulates Myeloma-Cell-Induced Interleukin-6 Production in Osteoblasts by Direct Interaction With the αvβ5 Integrin," *Blood* 107(8):3271-3278, (Apr. 2006).
Kaufman. "Overview of Vector Design for Mammalian Gene Expression," *Molecular Biotechnology* 16:151-160, (2000).
Kazama et al. "Hepsin, A Putative Membrane-Associated Serine Protease, Activates Human Factor VII and initiates a Pathway of Blood Coagulation on the Cell Surface Leading to Thrombin Formation," *JBC* 270:66-72, (1995).
Kim et al. "Inhibition of Vascular Endothelial Growth Factor-Induced Angiogenesis Suppresses Tumour Growth In Vivo," *Nature* 362:841-844, (1993).
Kindt et al. *Kuby Immunology*, 6th ed., W.H. Freeman and Co., N.Y. p. 91, (2007).
King et al. "Monoclonal Antibody Conjugates of Doxorubicin Prepared With Branched Peptide Linkers: Inhibition of Aggregation by Methoxytriethyleneglycol Chains," *J. Med. Chem.* 45:4336-4343, (2002).
Klein et al. "Progress in Overcoming the Chain Association Issue in Bispecific Heterodimeric IgG Antibodies," *mAbs* 4(6):653-663, (2012).
Kleinschmidt et al. "Design of a modular immunotoxin connected by polyionic adapter peptides," *J. Mol. Biol.* 327(2):445-452, (Mar. 21, 2003).
Kobayashi et al. "Similarities in the Biodistribution of Iodine-Labeled Anti-Tac Single-Chain Disulfide-Stabilized Fv Fragment and Anti-Tac Disulfide-Stabilized Fv Fragment," *Nuclear Medicine & Biology* 25:387-393, (1998).
Kodukula et al. "Biosynthesis of phosphatidylinositol glycan-anchored membrane proteins. Design of a simple protein substrate to characterize the enzyme that cleaves the COOH-terminal signal peptide," *The Journal of Biological Chemistry* 266(7):4464-4470, (Mar. 5, 1991).
Kratz et al. "Prodrugs of Anthracyclines in Cancer Chemotherapy," *Current Med. Chem.* 13:477-523, (2006).
Krugmann et al. "Structural Requirements for Assembly of Dimeric IgA Probed by Site-Directed Mutagenesis of J Chain and a Cysteine Residue of the α-chain CH2 Domain," *The Journal of Immunology* 159:244-249, (1997).
Kumar et al. "Molecular Cloning and Expression of the Fabs of Human Autoantibodies in *Escherichia coli*," *J. Biol. Chem.* 275(45):35129-35136, (Nov. 10, 2000).
Labrijn et al. "Species-Specific Determinants in the IgG CH3 Domain Enable Fab-Arm Exhange by Affecting the Noncovalent CH3—CH3 Interaction Strength," *The Journal of Immmunology* 187:3238-3246, (2011, e-pub. Aug. 12, 2011).
Lamkanfi et al. "Inflammasomes: Guardians of Cytosolic Sanctity," *Immunol. Rev.* 227(1):95-105, (Jan. 2009).
Landschulz et al. "The Leucine Zipper: A Hypothetical Structure Common to a New Class of DNA Binding Proteins," *Science* 240:1759-1764, (1988).
Lazar et al. "Transforming Growth Factor α: Mutation of Aspartic Acid 47 and Leucine 48 Results in Different Biological Activities," *Molecular and Cellular Biology* 8(3):1247-1252, (Mar. 1988).
Lee et al. "Generation and Characterization of a Novel Single-Gene-Encoded Single-Chain Immunoglobulin Molecule With Antigen Binding Activity and Effector Functions" *Mol Immunol.* 36(1):61-71, (1999).
Lee et al. "Using Substrate Specificity of Antiplasmin-Cleaving Enzyme for Fibroblast Activation Protein Inhibitor Design," *Biochemistry* 48(23):5149-5158, (Jun. 16, 2009).
Leeman et al. "The Structure, Regulation, and Function of Human Matrix Metalloproteinase-13," *Crit. Rev Biochem Mol. Biol.* 37(3):149-166, (2002).
Liang et al. "Cross-species Vascular Endothelial Growth Factor (VEGF)-blocking Antibodies Completely Inhibit the Growth of Human Tumor Xenografts and Measure the Contribution of Stromal VEGF," *Journal of Biological Chemistry* 281(2):951-961, (2006).
Lifely et al. "Glycosylation and Biological Activity of CAMPATH-1H Expressed in Different Cell Lines and Grown Under Different Culture Conditions," *Glycobiology* 5(8):813-822, (Dec. 1995).
Lin et al. "Structure-Function relationships in glucagon: Properties of highly purified des-his-, monoiodo-, and [Des-Asn$^{28}$, Thr$^{29}$](homoserine lactone$^{27}$)-glucagon," *Biochemistry USA* 14:1559-1563, (1975).
Lindmark et al. "Binding of Immunoglobulins to Protein A and Immunoglobulin Levels in Mammalian Sera," *J. Immunol. Meth.* 62:1-13, (1983).
Liotta et al. "Metastatic potential correlates with enzymatic degradation of basement membrane collagen," *Nature* 284(5751) 67-68, (Mar. 6, 1980).
Liu et al. (Aug. 6, 1996) "Eradication of Large Colon Tumor Xenografts by Targeted Delivery of Maytansinoids," *Proc. Natl. Acad. Sci. USA* 93:8618-8623.
Liu et al. "Clinical and Imaging Diagnosis of Primary Hepatic Lymphoma," *J First Mil Med. Univ*, 25(10):1290-1292, three pages, (2005). (Translation of the Abstract Only.).
Liu et al. "Heterogeneity of Monoclonal Antibodies," *Journal of Pharmaceutical Sciences* 97(7):2426-2447, (Jul. 2008).
Liu et al. "Mapping tumor epitope space by direct selection of single-chain Fv antibody libraries on prostate cancer cells," *Cancer Res.* 64:704-710, (2004).
Lode et al. "Targeted Therapy With a Novel Enediyene Antibiotic Calicheamicin θ$^I{}_1$ Effectively Suppresses Growth and Dissemina-

(56) References Cited

OTHER PUBLICATIONS tion of Liver Metastases in a Syngeneic Model of Murine Neuroblastoma," *Cancer Res.* 58:2925-2928, (Jul. 15, 1998).
Lopez-Otin et al. "The Regulatory Crosstalk Between Kinases and Proteases in Cancer," *Nat. Rev. Cancer* 10(4):278-292, (Apr. 2010).
Love et al. "Recombinant Antibodies Possessing Novel Effector Functions," *Methods in Enzymology* 178:515-527, (1989).
Lu et al. "A Fully Human Recombinant IgG-Like Bispecific Antibody to Both the Epidermal growth Factor Receptor and the Insulin-Like Growth Factor Receptor for Enhanced Antitumor Activity," *The Journal of Biological Chemistry* 280(20):19665-19672, (May 20, 2005).
Lu et al. "ADAMTS1 and MMP1 Proteolytically Engage EGF-Like Ligands in an Osteolytic Signaling Cascade for Bone Metastasis," *Genes Dev.* 23(16):1882-1894, (Aug. 2009).
Lu et al. "Fab-scFv Fusion Protein: an Efficient Approach to Production of Bispecific Antibody Fragments" *J. Immunol Methods* 267(2):213-26, (2002).
Lu et al. "Simultaneous Blockage of Both the Epidermal Growth Factor Receptor and the Insulin-Like Growth Factor Receptor Signaling Pathways in Cancer Cells With a Fully Human Recombinant Bispecific Antibody" *J. Biol. Chem.* 279(4):2856-2865, (Jan. 23, 2004).
Lu et al. "The Effect of Variable Domain Orientation and Arrangement on the Antigen-Binding Activity of a Recombinant Human Bispecific Diabody" *Biochem. Biophys. Res. Common.* 318(2):507-513, (2004, E-pub. Apr. 22, 2004).
Lukas et al. "Inhibition of C1-Mediated Immune Hemolysis by Monomeric and Dimeric Peptides from the Second Constant Domain of Human Immunoglobulin G," *The Journal of Immunology* 127(6):2555-2560, (Dec. 1981).
Lund et al. "Oligosaccharide-Protein Interactions In IgG Can Modulate Recognition by Fcγ Receptors," *FASEB Journal* 9:115-119, (1995).
MacCallum et al. "Antibody-Antigen Interactions: Contact Analysis and Binding Site Topography," *J. Mol. Biol.* 262:732-745, (1996).
Makrides. "Components of Vectors for Gene Transfer and Expression in Mammalian Cells," *Protein Expression and Purification* 17:183-202, (1999).
Mallender et al. "Comparative Properties of the Single Chain Antibody and Fv Derivateives of mAb Apr. 4, 2020. Relationship Between Interdomain Interactions and the High Affinity for Fluorescein Ligand," *Journal of Biological Chemistry* 271(10):5338-5346, (Mar. 8, 1996).
Malmborg et al. "BIAcore as a Tool in Antibody Engineering," *J. Immunol. Methods* 183:7-13, (1995).
Mamoune et al. "Calpain-2 as a Target for Limiting Prostate Cancer Invasion," *Cancer Res.* 63(15):4632-4640, (Aug. 2003).
Mandler et al. "Immunoconjugates of Geldanamycin and Anti-HER2 Monoclonal Antibodies: Antiproliferative Activity on Human Breast Carcinoma Cell Lines," *J. of the Nat. Cancer Inst.* 92(19):1573-1581, (Oct. 4, 2000).
Mandler et al. "Modifications in Synthesis Strategy Improve the Yield and Efficacy of Geldanamycin-herceptin Immunoconjugates," *Bioconjugate Chem.* 13(4):786-791, (Jul.-Aug. 2002, e-pub. Jun. 19, 2002).
Mandler et al. "Synthesis and Evaluation of Antiproliferative Activity of a Geldanamycin-Herceptin Immunoconjugate," *Biorganic & Med. Chem. Letters* 10:1025-1028, (May 15, 2000).
Mann. "Proteomic Analysis of Post-Translational Modifications," *Biochemistry* 21:255-261, (2003).
Marks et al. "By-Passing Immunization: Human Antibodies From V-gene Libraries Displayed on Phage," *J Mol Biol.* 222(3):581-597, (Dec. 5, 1991).
Marvin et al. "Bispecific antibodies for dual-modality cancer therapy: killing two signaling cascades with one stone," *Curr. Opin. Drug Discov. Devl.* 9:184-193, (2006).
Mason et al. "Coiled Coil Domains: Stability, Specificity, and Biological Implications," *ChemBioChem* 5:170-176, (2004).

Matrisian. "Cancer Biology: Extracellular Proteinases in Malignancy," *Curr. Biol.* 9(20):R776-R778, (Oct. 1999).
McCarron et al. "Antibody conjugates and therapeutic strategies," *Mol. Interventions* 5:368-380, (2005).
McKeen et al. "Synthesis of fluorophore and quencher monomers for use in scorpion primers and nucleic acid structural probes," *Organic & Biomol. Chem.* 1:2267-2275, (2003).
McLean et al. "A Point Mutation in the CH3 Domain of Human IgG3 Inhibits Antibody Secretion Without Affecting Antigen Specificity," *Molecular Immunology*, 42:1111-1119, (2005).
Meissner et al. "Transient Gene Expression: Recombinant Protein Production with Suspension-Adapted HEK293-EBNA Cells," *Biotechnology and Bioengineering* 75:197-203, (2001).
Melnyk et al. "Vascular Endothelial Growth Factor Promotes Tumor Dissemination by a Mechanism Distinct from Its Effect on Primary Tumor Growth," *Cancer Research* 56:921-924, (1996).
Merchant et al. "An Efficient Route to Human Bispecific IgG," *Nature Biotechnology* 16:677-681, (1998).
Meyer et al. "Oligonucleotide Sequential Bis-Conjugation Via Click-Oxime and Click-Huisgen Procedures," *Journal of Organic Chemistry* 75:3927-3930, (2010).
Michaelson et al., "Anti-Tumor Activity of Stability-Engineered IgG-Like Bispecific Antibodies Targeting TRAIL-R2 and LTβR," *MAbs* 1(2):128-141, (Mar. 2009, e-pub. Mar. 11, 2009).
Miller et al. "Design, Construction, and In Vitro Analyses of Multivalent Antibodies," *J. Immunol.* 170:4854-4861, (2003).
Milstein et al. "Hybrid Hybridomas and Their Use in Immunohistochemistry" *Nature* 305:537-540, (Oct. 6, 1983).
Mimura et al. "Role of Oligosaccharide Residues of IgG1-Fc in FcγRIIb Binding," *The Journal of Biological Chemistry* 276(49):45539-45547, (Dec. 7, 2001).
Minn et al. "Genes that Mediate Breast Cancer Metastasis to Lung," *Nature* 436(7050):518-524, (Jul. 2005).
Mirny et al. "Protein Folding Theory: From Lattice to All-Atom Models", *Annu. Rev. Biophys. Biomol. Struct.*, 30:361-96, (2001).
Mizukami et al. "Induction of Interleukin-8 Preserves the Angiogenic Response in HIF-1α-Deficient Colon Cancer Cells," *Nature Med.* 11:992-997, (2005).
Morgan et al. "The N-terminal End of the $C_H2$ Domain of Chimeric Human IgG 1 anti-HLA-DR is Necessary for C1q, FcγγRI and FcγRIII Binding," *Immunology* 86:319-324, (1995).
Morimoto et al. "Single-step purification of F(ab')2 fragments of mouse monoclonal antibodies (immunoglobulins G1) by hydrophobic interaction high performance liquid chromatography using TSKgel Phenyl-5PW," *J. Biochem. Biophys. Meth.* 24:107-117, (1992).
Morocho et al. "Novel Biotin Phosphoramidites With Super-Long Tethering Arms," *Nucleosides, Nucleotides & Nucleic Acids* 22 (2003) 1439-1441.
Morrison et al. "Chimeric Human Antibody Molecules: Mouse Antigen-Binding Domains with Human Constant Region Domains," *Proc. Natl. Acad. Sci. USA* 81(21):6851-6855, (Nov. 1984).
Morrison et al. "Variable Region Domain Exchange Influences the Functional Properties of IgG," *Journal of Immunology, American Association of Immunologists* 160:2802-2808, (Jan. 1, 1998).
Morrison. "Success in Specification," *Nature* 368:812-813, (Apr. 1994).
Morrison. "Two Heads are Better than One," *Nature Biotechnology* 25(11):1233-1234, (Nov. 2007).
Mukhopadhyay et al. "Matrix metalloproteinase-12 is a therapeutic target for asthma in children and young adults," *J. Allergy Clin Immunol.* 126:70-76, (2010).
Muller et al. "Processing and Sorting of the Prohormone Convertase 2 Propeptide," *J. Biol. Chem.* 275(50):39213-39222, (Dec. 15, 2000).
Müller et al. "Bispecific Antibodies," Chapter 2 in Handbook of Therapeutic Antibodies, Dübel, S. ed., Wiley-VCH Verlag GmbH & Company KGaA, Weinheim, pp. 345-378, (2007).
Müller et al. "Recombinant Bispecific Antibodies for Cellular Cancer Immunotherapy," *Current Opinion in Molecular Therapeutics* 9:319-326, (2007).
Müller et al. "The first constant domain ($C_H1$ and $C_L$) of an antibody used as heterodimerization domain for bispecific miniantibodies," *FEBS Letters* 422:259-264, (1998).

(56) References Cited

OTHER PUBLICATIONS

Murakami et al. "Cell Cycle Regulation, Oncogenes, and Antineoplastic Drugs" Chapter 1 in *The Molecular Basis of Cancer*, Mendelsohn and Israel, Philadelphia, W.B. Saunders, Philadelphia pp. 3-17, (1995).
Muyldermas et al. "Recognition of Antigens by Single-domain Antibody Fragments: the Superfluous Luxury of Paired Domains," *Trend Biochem. Sci.* 26(4):230-235, (Apr. 2001).
Nagy, A., et al. "Stability of Cytotoxic Luteinizing Hormone-Releasing Hormone Conjugate (AN-152) Containing Doxorubicin 14-O-Hemiglutarate in Mouse and Human Serum In Vitro: Implications for the Design of Preclinical Studies," *Proc. Natl. Acad. Sci. USA* 97:829-834, (2000).
Natsume et al. "Fucose Removal From Complex-type Oligosaccharide Enhances the Antibody-dependent Cellular Cytotoxicity of Single-gene-encoded Bispecific Antibody Comprising of Two Single-Chain Antibodies Linked to the Antibody Constant Region," *Journal of Biochemistry* 140(3):359-368, (Sep. 1, 2006).
Nelson, P.S., et al. "Oligonucleotide Labeling Methods. 3. Direct Labeling of Oligonucleotides Employing a Novel, Non-Nucleosidic, 2-Aminobutyl-1,3-Propanediol Backbone," *Nucleic Acids Research* 20:6253-6259, (1992).
Neri et al. "High-Affinity Antigen Binding by Chelating Recombinant Antibodies (CRAbs)," *J. Mol. Biol.* 246:367-373, (1995).
Netzel-Arnett et al. "Comparative Sequence Specificities of Human 72- and 92-kDa Gelatinases (Type IV Collagenases) and PUMP (matrilysin)," *Biochemistry* 32(25):6427-6432, (Jun. 29, 1993).
Netzel-Arnett et al. "Sequence Specificities of Human Fibroblast and Neutrophil Collagenases," *J. Biol. Chem.* 266(11):6747-6755, (Apr. 15, 1991).
Neuberger et al. "A Hapten-Specific Chimaeric Ige Antibody With Human Physiological Effector Function," *Nature* 314:263-270, (Mar. 21, 1985).
Nicolaou et al. Calicheamicin $\theta^I_1$: A Rationally Designed Molecule with Extremely Potent and Selective DNA Cleaving Properties and Apoptosis Inducing Activity, *Agnew Chem. Intl. Ed. Engl.* 33(2):183-186, (1994).
Niculescu-Duvaz et al. "Antibody-Directed Enzyme Prodrug Therapy (ADEPT): A Review," *Adv. Drg. Del. Rev.* 26:151-172, (1997).
Nielsen et al. "Therapeutic Efficacy of Anti-ErbB2 Immunoliposomes Targeted by a Phage Antibody Selected for Cellular Endocytosis," *Biochim. Biophys. Acta* 1591:109-118, (2002).
Nieri et al. "Antibodies for Therapeutic Uses and the Evolution of Biotechniques," *Current Med. Chem.* 16(6):753-779, (Feb. 1, 2009).
Nilsson et al. "A Synthetic IgG-binding Domain Based on Staphylococcal Protein A," *Prot. Eng.* 1:107-133, (1987).
Niwa et al., "IgG Subclass-Independent Improvement of Antibody-Dependent Cellular Cytotoxicity by Fucose Removal From $Asn^{297}$-Linked Oligosaccharides," *J. Immunol. Methods* 306:151-160, (2005).
Nord et al. "A Combinatorial Library of an A-Helical Bacterial Receptor Domain," *Prot. Eng.* 8:601-608, (1995).
Nord et al. "Binding Proteins Selected From Combinatorial Libraries of an A-Helical Bacterial Receptor Domain," *Nat. Biotech.* 15:772-777, (1997).
Norderhaug et al. "Versatile Vectors for Transient and Stable Expression of Recombinant Antibody Molecules in Mammalian Cells," *Journal of Immunological Methods* 204:77-87, (1997).
Novellino et al. "A Listing of Human Tumor Antigens Recognized by T Cells: Mar. 2004 Update," *Cancer Immunol. Immunother.* 54:187-207, (2005).
Novotný, J. et al. "Structural Invariants of Antigen Binding: Comparison of Immunoglobulin $V_L$—$V_H$ and $V_L$-$V_L$ Domain Dimmers," *Proc. Natl. Acad. Sci. USA*, 82:4592-4596, (1985).
O'Shea et al. "Peptide 'Velcro': Design of a Heterodimeric Coiled Coil," *Current Biology* 3(10):658-667, (1993).
Offner et al. "T Cell Receptor Peptide Therapy Triggers Autoregulation of Experimental Encephalomyelitis," *Science* 251:430-432, (Jan. 25, 1991).
Ohno et al. "Antigen-Binding Specificities of Antibodies Are Primarily Determined by Seven Residues of $V_H$," *Proc. Natl. Acad. Sci. USA* 82(9):2945-2949, (May 1985).
Oliner et al. Suppression of Angiogenesis and Tumor Growth by Selective Inhibition of Angiopoietin-2, *Cancer Cell* 6:507-516, (2004).
Orcutt, et al. "A Modular IgG-scFv Bispecific Antibody Topology," *Protein Engineering, Design & Selection* 23(4):221-223, (Apr. 2010, e-pub. Dec. 17, 2009).
Orlandi et al. "Cloning Immunoglobulin Variable Domains for Expression by the Polymerase Chain Reaction," *Proc. Natl. Acad. Sci. USA* 86:3833-3837, (May 1989).
Pace et al. "How to Measure and Predict the Molar Absorption Coefficient of a Protein," *Protein Science* 4(11): 2411-2423, (Nov. 1995).
Pakula et al. "Genetic Analysis of Protein Stability and Function," *Annu. Rev. Genet.* 23:289-310, (1989).
Pan, Q. et al. "Blocking Neuropilin-1 Function Has an Additive Effect with nti-VEGF to Inhibit Tumor Growth," *Cancer Cell* 11:53-67, (Jan. 2007).
Parmiani et al. "Unique Human Tumor Antigens: Immunobiology and Use in Clinical Trials," *J. Immunol.* 178:1975-1979, (2007).
Paul. "Structure and Function of Immunoglobulins," Chapter 9 in *Fundamental Immunology*, Third Edition, Raven Press, New York, New York, pp. 292-295, (1993).
Pettit et al. "The Dolastatins," *Fortschr. Chem. Org. Naturst.* 70:1-79, (1997).
Pettit et al. "Antineoplastic Agents 360. Synthesis and Cancer Cell Growth Inhibitory Studies of Dolastatin 15 Structural Modifications," *Anti-Cancer Drug Design* 13:47-66, (1998).
Pettit et al. "Marine Animal Biosynthetic Constituents for Cancer Chemotherapy," *J. Nat. Prod.* 44:482-485, (Jul.-Aug. 1981).
Pettit et. al. "Specific Activities of Dolastatin 10 and Peptide Derivatives Against *Cryptococcus neoformans*," *Antimirob. Agents Chemother.* 42(11):2961-2965, (Nov. 1998).
Pleass et al. "Identification of Residues in the CH2/CH3 Domain Interface of IgA Essential for Interaction With the Human fcα Receptor (Fcα R) CD89," *The Journal of Biology Chemistry* 274(33):23508-23514, (Aug. 13, 1999).
Plückthun et al. "New Protein Engineering Approaches to Multivalent and Bispecific Antibody Fragments," *Immunotechnology* 3:83-105, (1997).
Plückthun. "Antibodies from *Escherichia coli*," in *The Pharmacology of Monoclonal Antibodies*, Rosenburg and Moore (eds.), Springer-Verlag, New York, 113:269-315, (1994).
Pon, R.T. "A Long Chain Biotin Phosphoramidite Reagent for the Automated Synthesis of 5'-Biotinylated Oligonucleotides," *Tetrahedron Letters* 32:1715-1718, (1991).
Poncet. "The Dolastatins, A Family of Promising Antineoplastic Agents," *Curr. Pharm. Des.* 5:139-162, (1999).
Portolano et al. "Lack of Promiscuity In Autoantigen-Specific H and L chain Combinations as Revealed by Human H and L Chain Roulette," *J. Immunol.* 150:880-887, (1993).
PreScission Protease, GE Healthcare Catalogue No. 27-0843-01, located at http://www.gelifesciences.com/webapp/wcs/stores/servlet/productById/en/GELifeScience, last visited on Jul. 10, 2013, 1 page.
Presta. "Antibody Engineering," *Curr. Op. Struct. Biol.* 2:593-596, (1992).
Presta et al. "Humanization of an Anti-Vascular Endothelial Growth Factor Monoclonal Antibody for the Therapy of Solid Tumors and Other Disorders," *Cancer Res.* 57:4593-4599, (1997).
Presta et al. "Humanization of an Antibody Directed Against IgE," *J. Immunol.* 151(5):2623-2632, (Sep. 1, 1993).
Proba et al. "Functional Antibody Single-Chain Fragments From the Cytoplasm of *Escherichia coli*: Influence of Thioredoxin Reductase (TrxB)," *Gene* 159:203-207, (Jul. 4, 1995).
Prokhorenko, I.A., et al."Incorporation of a Pyrene Nucleoside Analogue Into Synthetic Oligodeoxynucleotides Using a Nucleoside-Like Synthon," *Bioorganic & Medicinal Chemistry Letters* 5:2081-2084, (1995).

(56) References Cited

OTHER PUBLICATIONS

Putnam et al. "Synthesis and Evaluation of RNA transesterification Efficiency Using Stereospecific Serinol-Terpyridine Conjugates," *Nucleosides, Nucleotides & Nucleic Acids* 24:1309-1323, (2005).
Raag et al. "Single-chain Fvs," *The FASEB Journal* 9:73-80, (Jan. 1995).
Radaev et al. "Recognition of IgG by Fcγ Receptor," *The Journal of Biological Chemistry* 276(19):16478-16483, (May 11, 2001).
Rajagopal et al., "A Form of Anti-Tac(Fv) Which is Both Single-chain and Disulfide Stabilized: Comparison with its single-chain and Disulfide-stabilized Homologs," *Protein Engineering* 10(12):1453-1459, (1997).
Raju. "Glycosylation Variations with Expression Systems and Their Impact on Biological Activity of Therapeutic Immunoglobulins," *BioProcess International* 1(4): 44-53, (Apr. 2003).
Ramm et al. "The Peroplasmic *Escherichia coli* Peptidylproly cis,trans-Isomerase FkpA," *J. Biol. Chem.* 275(22):17106-17113, (Jun. 2, 2001).
Ramzaeva et al. Oligonucleotides Fuctionalized by Fluorescein and Rhodamine Dyes: Michael Addition of Methyl Acrylate to 2'-Deoxypseudouridine, Helv. Chim. Acta 83:1108-1126, (2000).
Rawlings. "A Large and Accurate Collection of Peptidase Cleavages in the MEROPS Database," *Database* (Oxford), pp. 1-14, (2009, e-pub. Nov. 2, 2009).
Reiter et al. "Engineering Interchain Disulfide Bonds Into Conserved Framework Regions of Fv Fragments: Improved Biochemical Characteristics of Recombinant Immunotoxins Containing Disulfide-Stabilized Fv," *Protein Eng.* 7(5):697-704, (May 1994).
Reiter et al. "Stabilization of the Fv Fragments in Recombinant Immunotoxins by Disulfide Bonds Engineered into Conserved Framework Regions," *Biochemistry* 33:5451-5449, (1994).
Reiter et al., "Antibody Engineering of Recombinant Fv Immunotoxins for Improved Targeting of Cancer: Disulfide-Stabilized Fv Immunotoxins," *Clin. Cancer Res.* 2(2):245-252, (Feb. 1, 1996).
Reiter et al. "Antitumor Activity and Pharmacokinetics in Mice of a Recombinant Immunotoxin Containing a Disulfide-Stabilized Fv Fragment," *Cancer Research* 54:2714-2718, (1994).
Reiter et al. "Construction of a Functional Disulfide-Stabilized TCR Fv Indicates That Antibody and TCR Fv Frameworks Are Very Similar in Structure," *Immunity* 2:281-287, (1995).
Reiter et al. "Cytotoxic and Antitumor Activity of a Recombinant Immunotoxin Composed of Disulfide-Stabilized Anti-Tac Fv Fragment and Truncated Pseudomonas exotoxin," *International Journal of Cancer* 58:142-149, (1994).
Reiter et al. "Disulfide Stabilization of Antibody Fv: Computer Predictions and Experimental Evaluation," *Protein Engineering* 8:1323-1331, (1995).
Reiter et al. "Engineering Antibody Fv Fragments for Cancer Detection and Therapy: Disulfide-Stabilized Fv Fragments," *Nature Biotechnology* 14:1233-1245, (1996).
Reiter et al. "Improved Binding and Antitumor Activity of a Recombinant Anti-erbB2 Immunotoxin by Disulfide Stabilization of the Fv Fragment," *JBC* 269:18327-18331, (1994).
Remacle et al. "Substrate Cleavage Analysis of Furin and Related Proprotein Convertases," *Journal of Biological Chemistry* 283(30):20897-20906, (Jul. 25, 2008).
Ren et al. A Biocompatible Condensation Reaction for the Labeling of Terminal Cysteine Residues on Proteins,"*Angew. Chem. Int. Ed.* 48:9658-9662, (2009)."
Ren et al. "Macrophage Migration Inhibitory Factor Stimulates Angiogenic Factor Expression and Correlates With Differentiation and Lymph Node Status in Patients With Esophageal Squamous Cell Carcinoma," *Ann. Surg.* 242:55-63, (2005).
Ridgway et al. "'Knobs-into-holes' Engineering of antibody $C_H3$ domains for heavy chain heterodimerization," *Protein Engineering* 9(7):617-621, (1996).
Riechmann et al. "Reshaping Human Antibodies for Therapy," *Nature* 332:323-327, (Mar. 24, 1988).

Roget et al. "Synthesis and Use of Labelled Nucleoside Phosphoramidite Building Blocks Bearing a Reporter Group: Biotinyl, Dinitrophenyl, Pyrenyl and Dansyl," *Nucleic Acids Research* 17:7643-7651, (1989).
Roitt A. et al. "Multispecific Antibodies Comprising Full Length Antibodies and Single Chain Fab Fragments," *Immunology*, English Translation, Moscow:Mir, pp. 388-389, (2000).
Roitt et al., "Immunology" English Translation by McElroy Translation Company, Moscow *Mir* p. 110-111, (2000), 8 pages.
Rose et al. "Quantitative Analysis of the Interaction Strength and Dynamics of Human IgG4 Half Molecules by Native Mass Spectrometry," *Structure* 19:1274-1282, (Sep. 7, 2011).
Rossi, E.A. et al. "Multivalent Anti-CD20/Anti-CD22 Bispecific Antibody Fusion Proteins Made by the DNL Method Show Potent Lymphoma Cytotoxicity," *Blood, American Society of Hematology* 8:11, pp. 707A, (2006).
Routier et al. "The Glycosylation Pattern of a Humanized IgGl Antibody (D1.3) Expressed in CHO Cells," *Glycoconjugate Journal* 14:201-207, (1997).
Rowland et al. "Drug Localisation and Growth Inhibition Studies of Vindesine-Monoclonal Anti-CEA Conjugates in a Human Tumour Xenograft," *Cancer Immunol. Immunother.* 21:183-187, (1986).
Ruppert et al. "Cloning and Expression of Human $TAF_{II}250$: a TBP-Associated Factor Implicated in Cell-Cycle Regulation," *Nature* 362:175-179, (Mar. 11, 1993).
Ruppert et al. "Protease Levels in Breast, Ovary and other Gynecological Tumor Tissues: Prognostic Importance in Breast Cancer," *Cancer Detect. Prev.* 21(5):452-459, (1997).
Salfeld. "Isotype Selection in Antibody Engineering," *Nat. Biotechnol.* 25(12):1369-1372, (Dec. 2007).
Sambrook et al. *Molecular Cloning: A Laboratory Manual* "The Table of Contents" Cold Spring Harbor, New York: Cold Spring Harbor Laboratory Press, (1989).
Santos et al. "Generation and Characterization of a Single Gene-Encoded Single-Chain-tetravalent Antitumor Antibody" *Clinical Cancer Research* 5(10 Suppl):3118s-3123s, (Oct. 1999).
Schaefer et al. "Immunoglobulin domain crossover as a generic approach for the production of bispecific IgG antibodies," *Proc. Natl. Acad. Sci. U.S.A.* 108(27):11187-11192, (Jul. 5, 2011, e-pub. Jun. 20, 2011).
Schirrmann et al. Oligomeric Forms of Single Chain Immunoglobulin (sclgG),"*Landes Bioscience* 2(1):73-76, (Jan./Feb. 2010)."
Schlaeger et al. "Transient Gene Expression in Mammalian Cells Grown in Serum-free Suspension Culture," *Cytotechnology* 30:71-83, (1999).
Schlaeger. "The Protein Hydrolysate, Primatone RL, is a Cost Effective Multiple Growth Promoter of Mammalian Cell Culture in Serum-containing and Serum-free Media and Displays Anti-apoptosis Properties," *Journal of Immunological Methods* 194:191-199, (1996).
Schmidt et al. "Suppression of Metastasis Formation by a Recombinant Single Chain Antibody-Toxin Targeted to Full-Length and Oncogenic Variant EGF Receptors," *Oncogene* 18:1711-1721, (1999).
Schmiedl et al. "Expression of a Bispecific dsFv-dsFv' Antibody Fragment in *Escherichia coli,*" *Protein Engineering* 13(10):725-734, (Oct. 2000).
Schmiedl et al. "Effects of Unpaired Cysteines on Yield, Solubility and Activity of Different Recombinant Antibody Constructs Expressed in *E. coli,*" *Journal of Immunological Methods* 242: 101-114, (2000).
Schoonjans et al. "Efficient Heterodimerization of Recombinant Bi- and Trispecific Antibodies" *Bioseparation* 9(3):179-183, (2000).
Schoonjans et al. "Fab Chains as an Efficient Heterodimerization Scaffold for the Production of Recombinant Bispecific and Trispecific Antibody Derivatives," *Journal of Immunology* 165:7050-7057, (2000).
Schouten, A. et al. "The C-Terminal KDEL Sequence Increases the Expression Level of a Single-Chain Antibody Designed to be Targeted to Both the Cytosol and the Secretory Pathway in Transgenic Tobacco," *Plant Molecular Biology* 30:781-793. (1996).
Schröder et al. "III. Formation of the Peptide Bond," *The Peptides*, vol. 1, Academic Press, New York, New York, pp. 76-136, (1965).
Schwartz et al., "A Superactive Insulin: (B10-Aspartic Acid]Insulin(Human)," *Proc. Natl. Acad. Sci. USA* 84:6408-6411, (Sep. 1987).

(56) References Cited

OTHER PUBLICATIONS

Scott et al., "Biologic protease Inhibitors as Novel Therapeutic Agents," *Biochimie* 92(11):1681-1688, (Nov. 2010).
Seela, F. "Oligodeoxyribonucleotides Containing 1,3-Propanediol as Nucleoside Substitute," *Nucleic Acids Research* 15:3113-3129, (1987).
Sensi et al. "Unique Tumor Antigens: Evidence for Immune Control of Genome Integrity and Immunogenic Targets for T Cell-Mediated Patient-Specific Immunotherapy," *Clin. Cancer Res.* 12:5023-5032, (2006).
Senter, P.D., "Potent antibody drug conjugates for cancer therapy," *Curr. Opin. Chem. Biol.* 13:235-244, (2009).
Seo. "Post-Translational Modifications and Their Biological Functions: Proteomic Analysis and Systematic Approaches," *Biochemistry and Molecular Biology* 37(1):35-44, (2004).
Shechter et al. "Selective Chemical Cleavage of Tryptophanyl Peptide Bonds by Oxidative Chlorination With N-Chlorosuccinimide," *Biochemistry* 15(23):5071-5075, (1976).
Shen et al. "Single variable domain-IgG fusion: A novel recombinant approach to Fc domain-containing bispecific antibodies," *J. of Biological Chemistry* 281(16):10706-10714, (Apr. 21, 2006, e-pub. Feb. 15, 2006).
Shen et al. "Single variable domain antibody as a versatile building block for the construction of IgG-like bispecific antibodies," *Journal of Immunological Methods* 318:65-74, (2007).
Sheriff et al. "Redefining the minimal antigen-binding fragment," *Nature Struct. Biol.* 3:733-736, (1996).
Shi et al. "A stereospecific synthesis of L-deoxyribose, L-ribose and L-ribosides," *Tetrahed.* 58:3287-3296, (2002).
Shields et al. "Lack of Fucose on Human IgG1 N-Linked Oligosaccharide Improves Binding to Human FcγRIII and Antibody-dependent Cellular Toxicity," *J Biol Chem.* 277(30):26733-26740, (Jul. 26, 2002).
Shinkawa et al. "The Absence of Fucose but Not the Presence of galactose or Bisecting N-Acetylglucosamine of Human IgG1 Complex-Type Oligosaccharides Shows the Critical Role of Enhancing Antibody-Dependent Cellular cytotoxicity," *J. Biol. Chem.* 278 (5) 3466-3473, (2003).
Siebenlist et al. "*E. coli* RNA Polymerase Interacts Homologously with Two Different Promoters," *Cell* 20:269-281. (Jun. 1980).
Silva et al. "Synthesis of a new phosphoramidite nucleoside Biotinylated for the Preparation Oligonucleotide Multibiotinilados," *Biotecnologia Aplicada* 15:154-158, (1998). (English Abstract Only.).
Simmons et al., "Expression of Full-Length Immunoglobulins in *Escherichia coli*: Rapid and Efficient Production of Aglycosylated Antibodies," *Journal of Immunological Methods* 263:133-147, (2002).
Simon et al. "Antibody Domain Mutants Demonstrate Autonomy of the Antigen Binding Site," *The EMBO Journal* 9(4):1051-1056, (1990).
Sims et al. "A Humanized CD18 Antibody Can Block Function Without Cell Destruction," *J. Immunol.* 151(4):2296-2308, (Aug. 15, 1993).
Singer, M. and Berg, P. "Genes and genomes," Moscoer, MIR 1:63-64, (1998). (With English Translation.).
Smith-Gill et al. "Contributions of Immunoglobulin Heavy and Light Chain to Antibody Specificity for Lysozyme and Two Haptens," *J. Immunol.* 139(12):4135-4144, (Dec. 15, 1987).
Song et al. "Light Chain of Natural Anibody Plays a Dominant Role in Protein Antigen Binding," *Biochem. Biophys. Res. Comm.* 268(2):390-394, (2000).
Steiner. "The Biosynthesis of Biologically Active Peptides: A Perspective," Chapter 1 in *Peptide Biosynthesis and Processing*, Fricker ed., CRC Press, Boca Raton, FL, pp. 1-15, (1991).
Stella et al. "Prodrugs: A Chemical Approach to Target Drug Delivery" in *Directed Drug Delivery*, Borchardt et al (ed.), Human Press, pp. 247-267, (1985).
Stetler-Stevenson et al., "Progelatinase A Activation During Tumor Cell Invasion," *Invasion Metastasis* 14(1-6):259-268, (1994-1995).

Stevenson et al. "A Chimeric Antibody With Dual Fc Regions (bisFabFc) Prepared by Manipulations at the IgG Hinge," *Anti-cancer Drug Des.* 3(4):219-230, (Mar. 1989).
Stites et al. "Immunoglobulin Protiens," Chapter 6 in *Basic Clinical Immunology*, 8th Edition, Appleton & Lange, Norwalk, CT, p. 71, (1994).
Stork et al. "A Novel Tri-Functional Antibody Fusion Protein With Improved Pharmacokinetic Properties Generated by Fusing a Bispecific Single-Chain Diabody With an Albumin-Binding Domain From Streptococcal Protein G," *Protein Eng. Des. Sel.* 20(11):569-576, (Nov. 2007, e-pub. Nov. 3, 2007).
Su et al. "Novel Non-Nucleosidic Phosphoramidites for Oligonucleotide Modification and Labeling," *Bioorganic & Medicinal Chemistry Letters* 7:1639-1644, (1997).
Sunbul. "Site Specific Protein Labeling by Enzymatic Post-translational Modification," Org. *Biomol. Chem.* 7:3361-3371, (2009).
Syrigos et al. "Antibody Directed Enzyme Prodrug Therapy (ADEPT): A Review of the Experimental and Clinical Considerations," *Anti-cancer Research* 19:605-614, (1999).
Taki, M. et al. "Transglutaminase-Mediated N- and C-Terminal Fluorescein Labeling of a Protein Can Support the Native Activity of the Modified Protein," *Prot. Eng. Des. Sel.* 17:119-126, (2004).
Tao et al. "The Differential Ability of Human IgG1 and IgG4 to Activate Complement is Determined by the COOH-terminal Sequence of the $C_H2$ Domain," *J. Exp. Med* 173:1025-1028, (Apr. 1991).
Taylor, E. et al. "Native Chemical Ligation: SemiSynethesis of Post-Translationally Modified Proteins and Biological Probes," *Nucl. Acids Mol. Biol.* 22:65-96, (2009).
Theisen, P. et al. "Fluorescent Dye Phosphoramidite Labelling of Oligonucleotides," *Nucleic Acids*, Symposium Series 27 (Nineteenth Symposium on Nucleic Acids Chemistry), pp. 99-100, (1992).
Thie et al. "Multimerization Domains for Antibody Phage Display and Antibody Production," *New Biotech.* 26(6):314-321, (Jul. 22, 2009).
Thommesen et al. "Lysine 322 in the human IgG3 $C_H2$ domain is crucial for antibody dependent complement activation," *Molecular Immunology* 37:995-1004, (2000).
Thorpe. "Antibody Carriers of Cyotoxic Agents in Cancer Therapy: A Review," in *A Monoclonal Antibodies 84: Biological and Clinical Applications*, A. Pinchera et al (eds) pp. 475-506, (1985).
Torgov, M.Y. et al. "Generation of an intensely potent anthracycline by a monoclonal antibody-beta-galactosidase conjugate," *Bioconjug. Chem.* 16:717-721, (2005).
Torres, M. et al. "Variable-Region-Identical Antibodies Differing in Isotype Demonstrate Differences in Fine Specificity and Idiotype," *The Journal of Immunology*, 174:2132, (2005).
Tripathi et al. "Laminin-332 is a substrate for hepsin, a protease associated with prostate cancer progression," *JBC* 283:30576-30584, (2008).
Tso et al. "Preparation of a Bispecific F(ab')₂ Targeted to the Human II-2 Receptor," *J. Hematotherapy* 4:389-394, (1995).
Umaña et al. "Engineered Glycoforms of an Antineuroblastoma IgG1 with Optimized Antibody-Dependent Cellular Cytotoxic Activity" *Nature Biotechnology* 17(2):176-180 (Feb. 1999).
Urata, H., et al., "Synthesis and Properties of Mirror-Image DNA," *Nucl. Acids Res.* 20:3325-3332, (1992).
Vallbohmer et al. "Molecular Determinants of Cetuximab Efficacy," *J. Clin. Oncol.* 23:3536-3544, (2005).
Van Dijk and Van De Winkel., "Human antibodies as next generation therapeutics," *Curr. Opin. Chem. Biol.* 5(4): 368-74, (Aug. 2001).
Van Spriel et al. "Immunotherapeutic perspective for bispecific antibodies," *Immunology Today* 21(8):391-397, (Aug. 2000).
Van't Veer et al. "Gene expression profiling predicts clinical outcome of breast cancer," *Nature* 415(6871):530-536, (Jan. 2002).
Vazquez-Ortiz et al. "Overexpression of cathepsin F, matrix metalloproteinases 11 and 12 in cervical cancer," *BMC Cancer* 5:68, (Jun. 30, 2005).
Velasco et al. "Human cathepsin O. Molecular cloning from a breast carcinoma, production of the active enzyme in *Escherichia coli*, and expression analysis in human tissues," *J. Biol Chem* 269(43):27136-27142, (Oct. 28, 1994).

(56) References Cited

OTHER PUBLICATIONS

Verhoeyen et al. "Reshaping Human Antibodies: Grafting an Antilysozyme Activity," *Science* 239:1534-1536, (Mar. 25, 1988).
Veveris-Lowe et al. "Seminal Fluid Characterization for Male Fertility and Prostate Cancer: Kallikrein-Related Serine Proteases and whole Proteome Approaches," *Semin Thromb Hemost.* 33(1):87-99, (2007).
Vijayalakshmi. "Antibody Purification Methods" *Applied Biochemistry and Biotechnology* 75:93-102, (1998).
Vitetta, E.S., et al., "Redesigning nature's poisons to create antitumor reagents," *Science* 238 (1987) 1098-1104.
Walker et al. "Efficient Recovery of High-Affinity Antibodies From a Single-Chain Fab Yeast Display Library," *J. Mol. Biol.* 389(2):365-375, (Jun. 5, 2009, e-pub. Apr. 16, 2009).
Walker et al. "Efficient and Rapid Affinity Purification of Proteins Using Recombinant Fusion Proteases," *Bio/Technology* 12:601-605, (1994).
Wang et al. "Site-Specific Fluorescent Labeling of DNA Using Staudinger Ligation," *Bioconjugate Chemistry* 14:697-701, (2003).
Ward et al. "Binding Activities of a Repertoire of Single Immunoglobulin Variable Domains Secreted From *Escherichia coli,*" *Nature* 341:544-546, (1989).
Warren et al. "Regulation by Vascular Endothelial Growth Factor of Human Colon Cancer Tumorigenesis in a Mouse Model of Experimental Liver Metastasis," *J. Clin. Invest.* 95:1789-1797, (1995).
Webber et al. "Preparation and characterization of a disulfide-stabilized Fv fragment of the anti-Tac antibody: comparison with its single-chain analog," *Molecular Immunology* 32:249-258, (1995).
Werner et al. "Appropriate Mammalian Expression Systems for Biopharmaceuticals" *Drug Research* 48(8):870-880, (1998).
Wielockx et al. "Matrilysin (Matrix Metalloproteinase-7): A New Promising Drug Target in Cancer and Inflammation?" *Cytokine Growth Factor Rev.* 15(2-3):111-115, (Apr.-Jun. 2004).
Willems et al. "Optimizing Expression and Purification From Cell Culture Medium of Trispecific Recombinant Antibody Derivatives," *Journal of Chromatography B* 786:161-176, (2003).
Wilman. "Prodrugs in Cancer Chemotherapy" Biochemical Society Transactions, vol. 14, 615th Meeting Belfast, pp. 375-382, (1986).
Wojczewski et al. "Fluorescent oligonucleotides—versatile tools as probes and primers for DNA and RNA analysis," *Synlett* 10:1667-1678, (1999).
Woof et al. "Human antibody-FC receptor interactions illuminated by crystal structures," *Nat. Rev. Immunol.* 4:1-11, (2004).
Woyke et al. "In Vitro Activities and Postantifungal Effects of the Potent Dolastatin10 Derivative Auristatin PHE," *Antimicrob. Agents and Chemother.* 45(12):3580-3584, (Dec. 2001).
Wrank et al. "Luz-Y: A Novel Platform for the Mammalian Cell Production of Full-length IgG Bispeciic Antibodies," *Journal of Biological Chemistry* 287(52):43331-43339, (Dec. 21, 2012).
Wright and Morrison, "Effect of Glycosylation on Antibody Function: Implications for Genetic Engineering," *Trends in Biotechnology* 15:26-32, (1997).
Wright et al. "Phage Display of Chelating Recombinant Antibody Libraries," *Molecular Immunology* 44:2860-2869, (2007).
Wright et al. "ADAM28: A Potential Oncogene Involved in Asbestos-Related Lung Adenocarcinomas," *Genes Chromosomes Cancer* 49(8):688-698, (Aug. 2010).
Wu et al. "Simultaneous Targeting of Multiple Disease Mediators by a Dual-Variable-Domain Immunoglobulin" *Nature Biotechnology* 25(11):1290-1297, (Nov. 2007).
Xie et al. "A New Format of Bispecific Antibody: Highly Efficient Heterodimerization, Expression and Tumor Cell Lysis," *J. of Immunol. Methods* 296:95-101, (2005).

Xu et al. "Diversity in the CDR3 Region of V(H) Is Sufficient for Most Antibody Specificities," *Immunity* 13:37-45, (2000).
Yamaguchi et al. "Proteolytic Fragmentation With High Specificity of Mouse Immunoglobulin G," *Journal of Immunological Methods* 181:259-267, (1995).
Yaniv. "Enhancing Elements for Activation of Eukaryotic Promoters," *Nature* 297:17-18, (May 6, 1982).
Zahn et al. "Alternative heterocycles for DNA recognition: a 3-pyrazole/pyrrole pair specifies for G.C base pairs," *Bioorg. Med. Chem.* 8:2467-2474, (2000).
Zapata et al. "Engineering Linear F(ab')$_2$ Fragments for Efficient Production in *Escherichia coli* and Enhanced Antiproliferative Activity," *Protein Eng.* 8(10):1057-1062, (1995).
Zeidler et al. "Simultaneous activation of T cells and accessory cells by a new class of intact bispecific antibody results in efficient tumor cell killing," *Journal of Immunology* 163:1246-1252, (1999).
Zhu et al. "Remodeling Domain Interfaces to Enhance Heterodimer Formation," *Protein Science* 6:781-788, (1997).
Zuo et al. "An Efficient Route to the Production of an IgG-Like Bispecific Antibody," *Protein Engineering* 13(5):361-367, (2000).
Extended European Search Report dated Aug. 5, 2013, for European Patent Application No. 10817575.3, 11 pages.
International Preliminary Report on Patentability for PCT/EP2011/054505, dated Oct. 2, 2012, filed on Mar. 24, 2011, 8 pages.
International Preliminary Report on Patentability dated Aug. 21, 2014, for PCT Patent Application No. PCT/US2013/025365, filed on Feb. 8, 2013, 11 pages.
International Search Report for PCT/EP2011/054505 dated Jun. 28, 2011, filed on Mar. 24, 2011, 7 pages.
International Search Report dated Aug. 6, 2013, for PCT Application No. PCT/US2013/025365, filed Feb. 8, 2013, 6 pages.
International Search Report dated Dec. 6, 2011, for PCT Patent Application No. PCT/EP2011/064468 filed on Aug. 23, 2011, 7 pages.
International Search Report dated Dec. 6, 2011, for PCT Patent Application No. PCT/EP2011/064476 filed on Aug. 23, 2011, 7 pages.
International Search Report dated Jun. 15, 2011 for PCT Patent Application No. PCT/US2010/002546 filed on Sep. 16, 2010, 5 pages.
Written Opinion dated Aug. 6, 2013, for PCT Application No. PCT/US2013/025365, filed Feb. 8, 2013, 9 pages.
Written Opinion of the International Searching Authority dated Dec. 6, 2011, for PCT Patent Application No. PCT/EP2011/064468 filed on Aug. 23, 2011, 4 pages.
Written Opinion of the International Searching Authority dated Dec. 6, 2011, for PCT Patent Application No. PCT/EP2011/064476 filed on Aug. 23, 2011, 4 pages.
Written Opinion of the International Searching Authority dated Jun. 15, 2011 for PCT Patent Application No. PCT/US2010/002546 filed on Sep. 16, 2010, 7 pages.
Kunik, V. et al. "Paratome: An Online Tool for Systematic Identification of Antigen-Binding Regions in Antibodies Based on Sequence or Structure," *Nucleic Acids Research* 40:W521-W524, (2012, e-pub. Jun. 6, 2012).
Baer, S. et al. (2014). "Comparison of Alternative Nucleophiles for Sortase A-Mediated Bioconjugation and Application in Neuronal Cell Labelling," Org. Biomol Chem. 12:2675-2685.
Yin, Y. et al. (2019). "Preparation of a Novel One-Armed Anti-c-Met Antibody With Antitumor Activity Against Hepatocellular Carcinoma," Drug Design, Development and Therapy 13:4173-4184.

* cited by examiner

METHOD FOR MAKING ANTIBODY FC-REGION CONJUGATES COMPRISING AT LEAST ONE BINDING ENTITY THAT SPECIFICALLY BINDS TO A TARGET AND USES THEREOF

CROSS REFERENCE TO RELATED APPLICATIONS

This application is a continuation of International Application No. PCT/EP2013/063259 having an international filing date of Jun. 25, 2013, the entire contents of which are incorporated herein by reference, and which claims benefit under 35 U.S.C. § 119 to European Patent Application No. 12173876.9 filed Jun. 27, 2012.

SEQUENCE LISTING

Submission of Sequence Listing on ASCII Text File

The content of the following submission on ASCII text file is incorporated herein by reference in its entirety: a computer readable form (CRF) of the Sequence Listing (file name: 146392031301SUB2SEQLIST.TXT, date recorded: Aug. 23, 2018, size: 88 KB).

Herein are reported a method for enzymatically making antibody Fc-region conjugates in vitro by using a transpeptidase (e.g. the enzyme Sortase A) for covalently linking at least one binding entity that specifically binds to a target to an antibody Fc-region as well as the use of this method for the generation of novel e.g. monospecific or bispecific antibodies.

BACKGROUND OF THE INVENTION

Monoclonal antibodies have a great therapeutic potential and play an important role in today's medical portfolio. During the last decade, a significant trend in the pharmaceutical industry has been the development of monoclonal antibodies (mAbs) and antibody Fc-fusion polypeptides (crystallizable fragment-fusion polypeptides) as therapeutic agents across diverse clinical settings including oncology, chronic inflammatory diseases, transplantation, infectious diseases, cardiovascular medicine, or ophthalmologic diseases (Carter, J. P., Nature Reviews Immunology 6 (2006) 343-357; Chan, A. C. and Carter, J. P., Nature Reviews Immunology 10 (2010) 301-316).

The clinical efficiency of a therapeutic antibody relies mainly on two functionalities: i) the target-specific binding mediated by the Fv-domain, and ii) the immune-mediated effector function such as ADCC (antibody-dependent cell-mediated cytotoxicity), CDC (complement-dependent cytotoxicity), and ADCP (antibody-dependent cellular phagocytosis) which are mediated by the antibody Fc-region. The Fc-region of an immunoglobulin of the IgG class comprises the hinge region and two constant domains (CH2 and CH3). The Fc-region also interacts with the neonatal FcRn receptor and thereby determines the half-life of the antibody in vivo. The hinge region is the region at which the arms of an antibody molecule form a Y-like structure enabling flexibility in the molecule at this point. The IgG subclass/subclasses differ in the number of disulfide bonds in and the length of the hinge region.

The effector functions associated with the Fc-region of an antibody vary with the class and subclass of the antibody and include e.g. binding of the antibody via its Fc-region to a specific Fc receptor (FcR) on a cell which triggers various biological responses (see e.g. Jiang, X.-R., et al., Nature Reviews Drug Discovery 10 (2011) 101-110; Presta, L. G., Current Opinion in Immunology 20 (2008) 460-470).

The hinge region of an antibody or of an Fc-region comprising fusion polypeptide or conjugate is involved in at least a part of the antibody's functions such as antigen binding and Fc-region-mediated antibody effector functions. Whereas antigen binding (especially bivalent avid antibody binding) depends on the flexibility, length and spatial orientation of a particular/native hinge region the Fc-region mediated effector functions are dependent on the class and subclass of the antibody. The functional monovalency observed for some human IgG4 antibodies in comparison with the bivalency for other IgG antibodies is another example showing the involvement of the Fc-region in antigen binding properties.

In WO 2010/087994 a method for ligation and uses thereof is reported. Engineered proteins with high affinity for DOTA chelates are reported in WO 2010/099536.

SUMMARY OF THE INVENTION

It has been found that in a transpeptidase, e.g. Sortase A, catalyzed enzymatic conjugation reaction the formation of side reaction products can be reduced or even eliminated if a specifically engineered sortase motif in combination with a specifically engineered Fc-region are used.

In particular,
i) the reverse reaction based on the recognition of the LPX1TG (SEQ ID NO: 01) amino acid sequence within the product conjugate as substrate, and/or
ii) the generation of a dead-end hydrolysis polypeptide fragment (polypeptide without/cleaved LPX1TG (SEQ ID NO: 01) recognition sequence generated through cleavage of the thioacyl-transpeptidase intermediate by water instead by the oligoglycine nucleophile)

can be reduced or even eliminated in an enzymatic conjugation reaction if i) an antibody Fc-region, which comprises an oligoglycine ($G_m$ with m=2, or 3, or 4, or 5) at least at one of its N-termini, and
ii) a binding entity that specifically binds to a target, such as single chain antigen binding polypeptides (e.g. scFvs, scFabs and darpins) or a multi-chain antigen binding polypeptides (e.g. dsFvs and Fab-antibody fragments), which comprises a $G_nSLPX1TG$ (SEQ ID NO: 02, n=1, 2, or 3, and wherein X1 can be any amino acid residue) amino acid sequence in its C-terminal region is used.

Additionally it has been found that by using the above combination of C-terminal and N-terminal amino acid sequences an improved reaction yield can be obtained.

One aspect as reported herein is a method for producing an antibody Fc-region conjugate from exclusively recombinantly produced starting polypeptides comprising a first recombinant component comprising an antibody Fc-region and a second recombinant component comprising at least one binding entity, which specifically binds to a target, using a transpeptidase for enzymatic conjugation of the antibody Fc-region to the at least one binding entity.

In one embodiment the transpeptidase is Sortase A. In one embodiment the Sortase A is *Staphylococcus aureus* Sortase A.

In one embodiment the binding entities are independently of each other selected from a darpin domain based binding entity, an anticalin domain based binding entity, a T-cell receptor fragment like scTCR domain based binding entity, a camel VH domain based binding entity, a tenth fibronectin 3 domain based binding entity, a tenascin domain based binding entity, a cadherin domain based binding entity, an ICAM domain based binding entity, a titin domain based binding entity, a GCSF-R domain based binding entity, a cytokine receptor domain based binding entity, a glycosidase inhibitor domain based binding entity, a superoxide dismutase domain based binding entity, or antibody fragments like Fab or scFv fragments.

In one embodiment the target binding scaffold is selected from darpins, hemopexin-like molecule, and anticalins.

In one embodiment the binding entity that specifically binds to a target is selected from antibodies, antibody fragments, receptors, receptor ligands, and target binding scaffolds, with the proviso that the receptor ligand is not an incretin receptor ligand polypeptide.

In one embodiment the antibody fragment is selected from the group comprising Fv, Fab, Fab', Fab'-SH, F(ab')$_2$, diabody, linear antibody, scFv, scFab, and dsFv.

In one embodiment the receptor is selected from T-cell receptor fragments and scTCR.

In one embodiment the antibody Fc-region comprises two polypeptide chains linked by at least one disulfide bond.

In one embodiment the antibody Fc-region comprises two disulfide-linked full length heavy chain antibody Fc-regions, or two heavy chain antibody Fc-region fragments, or a full length antibody heavy chain paired with the cognate full length light chain and a disulfide-linked full length heavy chain antibody Fc-region, or a full length antibody heavy chain disulfide-linked to a full length antibody heavy chain Fc-region polypeptide.

In one embodiment the method comprises the following step:

incubating i) a binding entity that specifically binds to a target comprising the amino acid sequence $G_n$SLPX1TG (SEQ ID NO: 02, n=1, 2, or 3, and wherein X1 can be any amino acid residue) within its 20 C-terminal amino acid residues, and ii) an antibody Fc-region comprising at least at one N-terminus an oligoglycine $G_m$ (with m=1, 2, or 3) with the enzyme Sortase A and thereby producing the antibody Fc-region conjugate.

In one embodiment the binding entity that specifically binds to a target comprises the amino acid sequence $G_n$SLPX1TGGSGS (SEQ ID NO: 03, n=1, 2 or 3 and wherein X1 can be any amino acid residue) within the 20 C-terminal amino acid residues.

In one embodiment the binding entity that specifically binds to a target comprises the amino acid sequence X2GSLPX1TGGSGS (SEQ ID NO: 04, wherein X1 can be any amino acid residue) within the 20 C-terminal amino acid residues, whereby X2 can be any amino acid residue except glycine.

In one embodiment the binding entity that specifically binds to a target comprises the amino acid sequence $G_n$SLPX1TGGSGSX3 (SEQ ID NO: 05, n=1, 2 or 3 and wherein X1 can be any amino acid residue) within the 20 C-terminal amino acid residues, whereby X3 is an amino acid sequence tag.

In one embodiment the binding entity that specifically binds to a target comprises the amino acid sequence X2GSLPX1TGGSGSX3 (SEQ ID NO: 06, wherein X1 can be any amino acid residue) within the 20 C-terminal amino acid residues, whereby X2 can be any amino acid residue except glycine, and whereby X3 is an amino acid sequence tag.

In one embodiment the binding entity that specifically binds to a target comprises the amino acid sequence of SEQ ID NO: 02, or SEQ ID NO: 03, or SEQ ID NO: 04, or SEQ ID NO: 05, or SEQ ID NO: 06 at its C-terminus as C-terminal amino acid residues.

In one embodiment the antibody Fc-region comprises at least at one of its N-termini two glycine residues.

In one embodiment the antibody Fc-region comprises at both of its N-termini two glycine residues.

In one embodiment the antibody Fc-region comprises at least at one of its N-termini the amino acid sequence GGCPX4C (SEQ ID NO: 07), or the amino acid sequence GGHTCPX4C (SEQ ID NO: 08), wherein X4 is either S or P.

In one embodiment the antibody Fc-region comprises at both of its N-termini independently of each other the amino acid sequence GGCPX4C (SEQ ID NO: 07) or the amino acid sequence GGHTCPX4C (SEQ ID NO: 08), wherein X4 is independently of each other either S or P.

In one embodiment the binding entity that specifically binds to a target specifically binds to a first epitope or antigen and the antibody Fc-region comprises a second binding entity that specifically binds to a second epitope or antigen that is different from the first epitope or antigen.

One aspect as reported herein is an antibody Fc-region conjugate obtained by a method as reported herein.

One aspect as reported herein is an antibody Fc-region conjugate comprising the amino acid sequence $G_n$SLPX1TGG (SEQ ID NO: 09, n=1, 2 or 3 and wherein X1 can be any amino acid residue).

In one embodiment the antibody Fc-region conjugate comprises the amino acid sequence $G_n$SLPX1TGGCPX4C (SEQ ID NO: 10, n=1, 2 or 3), wherein X1 can be any amino acid residue, and wherein X4 is either S or P.

In one embodiment the antibody Fc-region conjugate comprises the amino acid sequence X2GSLPX1TGGCPX4C (SEQ ID NO: 11), wherein X1 can be any amino acid residue, wherein X4 is either S or P, and wherein X2 can be any amino acid residue except glycine.

In one embodiment the antibody Fc-region conjugate comprises the amino acid sequence $G_n$SLPX1TGGHTCPX4C (SEQ ID NO: 12, n=1, 2 or 3), wherein X1 can be any amino acid residue, and wherein X4 is either S or P.

In one embodiment the antibody Fc-region conjugate comprises the amino acid sequence X2GSLPX1TGGHTCPX4C (SEQ ID NO: 13), wherein X1 can be any amino acid residue, wherein X4 is either S or P, and wherein X2 can be any amino acid residue except glycine.

In one embodiment the antibody Fc-region conjugate comprises a first and a second polypeptide chain that are covalently linked by at least one disulfide bond.

In one embodiment the antibody Fc-region conjugate comprises a first polypeptide chain that is a full length antibody heavy chain and a second polypeptide chain that is an antibody heavy chain that comprises the amino acid sequence $G_n$SLPX1TGGCPX4C (SEQ ID NO: 10, n=1, 2 or 3), whereby the first and second polypeptide chain are covalently linked by at least one disulfide bond, wherein X1 can be any amino acid residue, and wherein X4 is either S or P.

In one embodiment the antibody Fc-region conjugate comprises a first polypeptide chain that is a full length antibody heavy chain and a second polypeptide chain that is an antibody heavy chain that comprises the amino acid sequence $G_n$SLPX1TGGHTCPX4C (SEQ ID NO: 12, n=1, 2 or 3), whereby the first and second polypeptide chain are covalently linked by at least one disulfide bond, wherein X1 can be any amino acid residue, and wherein X4 is either S or P.

In one embodiment the antibody Fc-region conjugate comprises two polypeptide chains whereof each is an antibody heavy chain that comprises the amino acid sequence G$_n$SLPX1TGGHTCPX4C (SEQ ID NO: 12, n=1, 2 or 3), whereby the two polypeptide chains are covalently linked by at least one disulfide bond, wherein X1 can be any amino acid residue, and wherein X4 is either S or P.

In one embodiment of all aspects X1 is E.

In one embodiment of all aspects as reported herein the antibody Fc-region is a human antibody Fc-region or a variant thereof.

In one embodiment the human antibody Fc-region is of human IgG1 subclass, or of human IgG2 subclass, or of human IgG3 subclass, or of human IgG4 subclass.

In one embodiment the antibody Fc-region is a human antibody Fc-region of the human IgG1 subclass, or of the human IgG4 subclass.

In one embodiment the human antibody Fc-region comprises a mutation of the naturally occurring amino acid residue at least at one of the following amino acid positions 228, 233, 234, 235, 236, 237, 297, 318, 320, 322, 329, and/or 331 to a different residue, wherein the residues in the antibody Fc-region are numbered according to the EU index of Kabat.

In one embodiment the human antibody Fc-region comprises a mutation of the naturally occurring amino acid residue at position 329 and at least one further mutation of at least one amino acid residue selected from the group comprising amino acid residues at position 228, 233, 234, 235, 236, 237, 297, 318, 320, 322 and 331 to a different residue, wherein the residues in the Fc-region are numbered according to the EU index of Kabat. The change of these specific amino acid residues results in an altering of the effector function of the Fc-region compared to the non-modified (wild-type) Fc-region.

In one embodiment the human antibody Fc-region has a reduced affinity to the human FcγRIIIA, and/or FcγRIIA, and/or FcγRI compared to a conjugate comprising the corresponding wild-type IgG Fc-region.

In one embodiment the amino acid residue at position 329 in the human antibody Fc-region is substituted with glycine, or arginine, or an amino acid residue large enough to destroy the proline sandwich within the Fc-region.

In one embodiment the mutation in the human antibody Fc-region of the naturally occurring amino acid residue is at least one of S228P, E233P, L234A, L235A, L235E, N297A, N297D, P329G, and/or P331S.

In one embodiment the mutation is L234A and L235A if the antibody Fc-region is of human IgG1 subclass, or S228P and L235E if the antibody Fc-region is of human IgG4 subclass.

In one embodiment the antibody Fc-region comprises the mutation P329G.

In one embodiment the antibody Fc-region comprises the mutation T366W in the first heavy chain Fc-region polypeptide and the mutations T366S, L368A and Y407V in the second heavy chain Fc-region polypeptide, wherein the numbering is according to the EU index of Kabat.

In one embodiment the antibody Fc-region comprises the mutation S354C in the first heavy chain Fc-region polypeptide and the mutation Y349C in the second heavy chain Fc-region polypeptide.

DETAILED DESCRIPTION OF EMBODIMENTS OF THE INVENTION

I. Definitions

Figure 1:
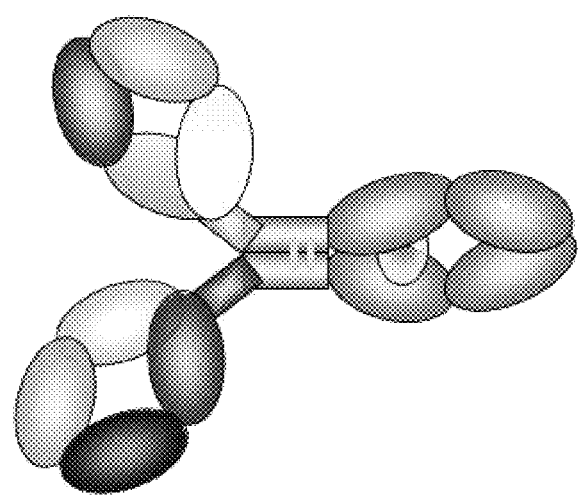
FIG. 1 Schematic outline of the generation of bivalent antibodies using Sortase A.
Figure 1:
Figure 1:
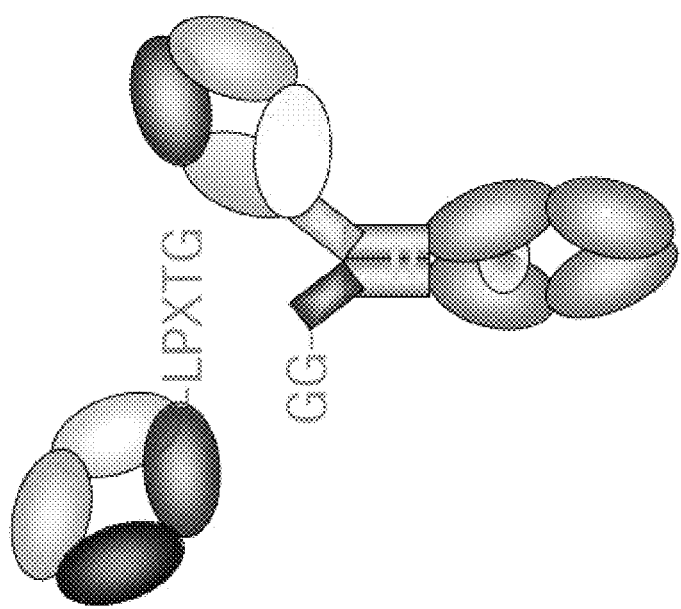
Figure 2:
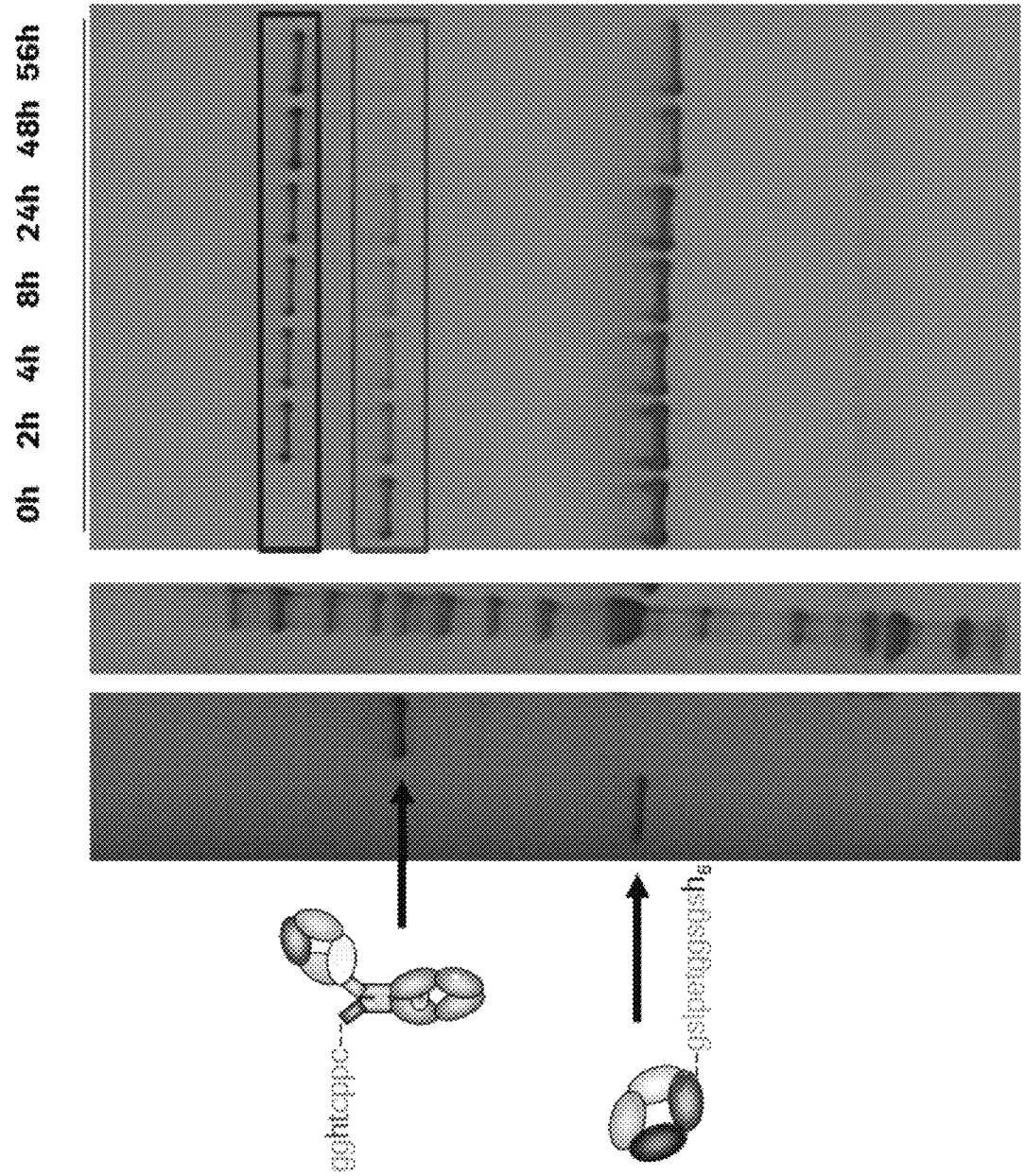
FIG. 2 SDS-page analysis of the course of the coupling reaction. GGHTCPPC (SEQ ID NO: 18), GSL-PETGGSGSHHHHHH (SEQ ID NO: 15).

In the present specification and claims the numbering of the residues in an immunoglobulin heavy chain Fc-region is that of the EU index of Kabat (Kabat, E. A., et al., Sequences of Proteins of Immunological Interest, 5th ed., Public Health Service, National Institutes of Health, Bethesda, Md. (1991), NIH Publication 91-3242, expressly incorporated herein by reference).

The term "alteration" denotes the mutation, addition, or deletion of one or more amino acid residues in a parent amino acid sequence, e.g. of an antibody or fusion polypeptide comprising at least an FcRn binding portion of an Fc-region, to obtain a variant antibody or fusion polypeptide.

The term "amino acid mutation" denotes a modification in the amino acid sequence of a parent amino acid sequence. Exemplary modifications include amino acid substitutions, insertions, and/or deletions. In one embodiment the amino acid mutation is a substitution. The term "amino acid mutations at the position" denotes the substitution or deletion of the specified residue, or the insertion of at least one amino acid residue adjacent the specified residue. The term "insertion adjacent to a specified residue" denotes the insertion within one to two residues thereof. The insertion may be N-terminal or C-terminal to the specified residue.

The term "amino acid sequence tag" denotes a sequence of amino acid residues connected to each other via peptide bonds that has specific binding properties. In one embodiment the amino acid sequence tag is an affinity or purification tag. In one embodiment the amino acid sequence tag is selected from Arg-tag, His-tag, Flag-tag, 3×Flag-tag, Strep-tag, Nano-tag, SBP-tag, c-myc-tag, S-tag, calmodulin-binding-peptide, cellulose-binding-domain, chitin-binding-domain, GST-tag, or MBP-tag. In one embodiment the amino acid sequence tag is selected from SEQ ID NO: 20 (RRRRR), or SEQ ID NO: 21 (RRRRRR), or SEQ ID NO: 22 (HHHHHH), or SEQ ID NO: 23 (KDHLIHNVHKEFHAHAHNK), or SEQ ID NO: 24 (DYKDDDDK), or SEQ ID NO: 25 (DYKDHDGDYKDHDIDYKDDDDK), or SEQ ID NO: 26 (AWRHPQFGG), or SEQ ID NO: 27 (WSHPQFEK), or SEQ ID NO: 28 (MDVEAWLGAR), or SEQ ID NO: 29 (MDVEAWLGARVPLVET), or SEQ ID NO: 30 (MDEKTTGWRGGHVVEGLAGELEQLRARLEHHPQGQREP), or SEQ ID NO: 31 (EQKLISEEDL), or SEQ ID NO: 32 (KETAAAKFERQHMDS), or SEQ ID NO: 33 (KRRWKKNFIAVSAANRFKKISSSGAL), or SEQ ID NO: 34 (cellulose binding domain), or SEQ ID NO: 35 (cellulose binding domain), or SEQ ID NO: 36 (TNPGVSAWQVNTAYTAGQLVTYNGKTYKCLQPHTSLAGWEP SNVPALWQLQ), or SEQ ID NO: 37 (GST-tag) or SEQ ID NO: 38 (MBP-tag).

The term "amino acid substitution" denotes the replacement of at least one amino acid residue in a predetermined parent amino acid sequence with a different "replacement" amino acid residue. The replacement residue or residues may be a "naturally occurring amino acid residue" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). In one embodiment the replacement residue is not cysteine. Substitution with one or more non-naturally occurring amino acid residues is also encompassed by the definition of an amino acid substitution herein. A "non-naturally occurring amino acid residue" denotes a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine, aib and other amino acid residue analogues such as those described in Ellman, et al., Meth. Enzym. 202 (1991) 301-336. To generate such non-naturally occurring amino acid residues, the procedures of Noren, et al. (Science 244 (1989) 182) and/or Ellman, et al. (supra) can be used. Briefly, these procedures involve chemically activating a suppressor tRNA with a non-naturally occurring amino acid residue followed by in vitro transcription and translation of the RNA. Non-naturally occurring amino acids can also be incorporated into peptides via chemical peptide synthesis and subsequent fusion of these peptides with recombinantly produced polypeptides, such as antibodies or antibody fragments.

The term "amino acid insertion" denotes the incorporation of at least one additional amino acid residue into a predetermined parent amino acid sequence. While the insertion will usually consist of the insertion of one or two amino acid residues, the present application contemplates larger "peptide insertions", e.g. insertion of about three to about five or even up to about ten amino acid residues. The inserted residue(s) may be naturally occurring or non-naturally occurring as defined above.

The term "amino acid deletion" denotes the removal of at least one amino acid residue at a predetermined position in an amino acid sequence.

Within this application whenever an amino acid alteration is mentioned it is a deliberated amino acid alteration and not a random amino acid modification.

The term "antibody-dependent cell-mediated cytotoxicity", short "ADCC", denotes a cell-mediated reaction in which non-antigen specific cytotoxic cells that express FcRs (e.g. natural killer cells (NK cells), neutrophils, and macrophages) recognize a target cell by binding to immunoglobulin Fc-region and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9 (1991) 457-492.

The term "antibody-dependent cellular phagocytosis", short "ADCP", denotes a process by which antibody-coated cells are internalized, either in whole or in part, by phagocytic immune cells (e.g. macrophages, neutrophils, or dendritic cells) that bind to an immunoglobulin Fc-region.

The term "antibody fragment" denotes a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g. scFv), and multispecific antibodies formed from antibody fragments.

The term "binding to an Fc receptor" denotes the binding of an Fc-region to an Fc receptor in, for example, a BIAcore® assay (Pharmacia Biosensor AB, Uppsala, Sweden).

In the BIAcore® assay the Fc receptor is bound to a surface and binding of the analyte, e.g. an Fc-region comprising fusion polypeptide or an antibody, is measured by surface plasmon resonance (SPR). The affinity of the binding is defined by the terms ka (association constant: rate constant for the association of the Fc-region fusion polypeptide or conjugate to form an Fc-region/Fc receptor complex), kd (dissociation constant; rate constant for the dissociation of the Fc-region fusion polypeptide or conjugate from an Fc-region/Fc receptor complex), and KD (kd/ka). Alternatively, the binding signal of a SPR sensorgram can be compared directly to the response signal of a reference, with respect to the resonance signal height and the dissociation behaviors.

The term "C1q" denotes a polypeptide that includes a binding site for the Fc-region of an immunoglobulin. C1q together with two serine proteases, C1r and C1s, forms the complex C1, the first component of the complement dependent cytotoxicity (CDC) pathway. Human C1q can be purchased commercially from, e.g. Quidel, San Diego, Calif.

The term "CH2 domain" denotes the part of an antibody heavy chain polypeptide that extends approximately from EU position 231 to EU position 340 (EU numbering system according to Kabat). In one embodiment a CH2 domain has the amino acid sequence of APELLGGPSVFLFPPKPKDTLMISRTPEVTCVWDVSHEDPEVKFNWYVDG VEVHNAKTKPREEQESTYRWSVLTVLHQDWLNGKEYKCKVSNKALPAPI EKTISKAK (SEQ ID NO: 39). The CH2 domain is unique in that it is not closely paired with another domain. Rather, two N-linked branched carbohydrate chains are interposed between the two CH2 domains of an intact native Fc-region. It has been speculated that the carbohydrate may provide a substitute for the domain-domain pairing and help stabilize the CH2 domain. Burton, Mol. Immunol. 22 (1985) 161-206.

The term "CH3 domain" denotes the part of an antibody heavy chain polypeptide that extends approximately from EU position 341 to EU position 446. In one embodiment the CH3 domain has the amino acid sequence of GQPREPQVYTLPPSRDELTKNQVSLTCLVKGFYPS-DIAVEWESNGQPENNY KTTPPVLDSDGSFFLYSK-LTVDKSRWQQGNVFSCSVMHEALHNHYTQKSL SLSPG (SEQ ID NO: 40).

The term "class" of an antibody denotes the type of constant domain or constant region possessed by its heavy chain. There are five major classes of antibodies in humans: IgA, IgD, IgE, IgG, and IgM, and several of these may be further divided into subclasses, e.g., IgG1, IgG2, IgG3, IgG4, IgA1, and IgA2. The heavy chain constant domains that correspond to the different classes of immunoglobulins are called α, δ, ε, γ, and μ, respectively.

The term "complement-dependent cytotoxicity", short "CDC", denotes a mechanism for inducing cell death in which an Fc-region of a target-bound Fc-region fusion polypeptide or conjugate activates a series of enzymatic reactions culminating in the formation of holes in the target cell membrane. Typically, antigen-antibody complexes such as those on antibody-coated target cells bind and activate complement component C1q which in turn activates the complement cascade leading to target cell death. Activation of complement may also result in deposition of complement components on the target cell surface that facilitate ADCC or ADCP by binding complement receptors (e.g., CR3) on leukocytes.

The term "effector function" denotes those biological activities attributable to the Fc-region of an antibody, which vary with the antibody subclass. Examples of antibody effector functions include: C1q binding and complement dependent cytotoxicity (CDC); Fc receptor binding; antibody-dependent cell-mediated cytotoxicity (ADCC); phagocytosis (ADCP); down regulation of cell surface receptors (e.g. B-cell receptor); and B-cell activation. Such function can be effected by, for example, binding of an Fc-region to an Fc receptor on an immune cell with phagocytic or lytic activity, or by binding of an Fc-region to components of the complement system.

The term "reduced effector function" denotes a reduction of a specific effector function associated with a molecule, like for example ADCC or CDC, in comparison to a control molecule (for example a polypeptide with a wild-type Fc-region) by at least 20%. The term "strongly reduced effector function" denotes a reduction of a specific effector function associated with a molecule, like for example ADCC or CDC, in comparison to a control molecule by at least 50%.

The term "Fc-region" denotes the C-terminal region of an immunoglobulin. The Fc-region is a dimeric molecule comprising two disulfide-linked antibody heavy chain fragments (heavy chain Fc-region polypeptide chains). An Fc-region can be generated by papain digestion, or IdeS digestion, or trypsin digestion of an intact (full length) antibody or can be produced recombinantly.

The Fc-region obtainable from a full length antibody or immunoglobulin comprises at least residues 226 (Cys) to the C-terminus of the full length heavy chain and, thus, comprises a part of the hinge region and two or three constant domains, i.e. a CH2 domain, a CH3 domain, and an additional/extra CH4 domain on IgE and IgM class antibodies. It is known from U.S. Pat. Nos. 5,648,260 and 5,624,821 that the modification of defined amino acid residues in the Fc-region results in phenotypic effects.

The formation of the dimeric Fc-region comprising two identical or non-identical antibody heavy chain fragments is mediated by the non-covalent dimerization of the comprised CH3 domains (for involved amino acid residues see e.g. Dall'Acqua, Biochem. 37 (1998) 9266-9273). The Fc-region is covalently stabilized by the formation of disulfide bonds in the hinge region (see e.g. Huber, et al., Nature 264 (1976) 415-420; Thies, et al., J. Mol. Biol. 293 (1999) 67-79). The introduction of amino acid residue changes within the CH3 domain in order to disrupt the dimerization of CH3-CH3 domain interactions do not adversely affect the neonatal Fc receptor (FcRn) binding due to the location of the CH3-CH3-domain dimerization involved residues are located on the inner interface of the CH3 domain, whereas the residues involved in Fc-region-FcRn interaction are located on the outside of the CH2-CH3 domain.

The residues associated with effector functions of an Fc-region are located in the hinge region, the CH2, and/or the CH3 domain as determined for a full length antibody molecule. The Fc-region associated/mediated functions are:
  (i) antibody-dependent cellular cytotoxicity (ADCC),
  (ii) complement (C1q) binding, activation and complement-dependent cytotoxicity (CDC),
  (iii) phagocytosis/clearance of antigen-antibody complexes,
  (iv) cytokine release in some instances, and
  (v) half-life/clearance rate of antibody and antigen-antibody complexes.

The Fc-region associated effector functions are initiated by the interaction of the Fc-region with effector function specific molecules or receptors. Mostly antibodies of the IgG1 subclass can effect receptor activation, whereas antibodies of the IgG2 and IgG4 subclasses do not have effector function or have limited effector function.

The effector function eliciting receptors are the Fc receptor types (and sub-types) FcγRI, FcγRII and FcγRIII. The effector functions associated with an IgG1 subclass can be reduced by introducing specific amino acid changes in the lower hinge region, such as L234A and/or L235A, which are involved in FcγR and C1q binding. Also certain amino acid residues, especially located in the CH2 and/or CH3 domain, are associated with the circulating half-life of an antibody molecule or an Fc-region fusion polypeptide in the blood stream. The circulatory half-life is determined by the binding of the Fc-region to the neonatal Fc receptor (FcRn).

The sialyl residues present on the Fc-region glycostructure are involved in anti-inflammatory mediated activity of the Fc-region (see e.g. Anthony, R. M., et al. Science 320 (2008) 373-376).

The numbering of the amino acid residues in the constant region of an antibody is made according to the EU index of Kabat (Kabat, E. A., et al., Sequences of Proteins of Immunological Interest, 5th ed., Public Health Service, National Institutes of Health, Bethesda, Md. (1991), NIH Publication 91 3242).

The term "human antibody Fc-region" denotes the C-terminal region of an immunoglobulin heavy chain of human origin that contains at least a part of the hinge region, the CH2 domain and the CH3 domain. In one embodiment, a human IgG antibody heavy chain Fc-region extends from about Glu216, or from about Cys226, or from about Pro230, to the carboxyl-terminus of the heavy chain. However, the C-terminal lysine (Lys447) of the antibody Fc-region may or may not be present.

The term "variant Fc-region" denotes an amino acid sequence which differs from that of a "native" or "wild-type" Fc-region amino acid sequence by virtue of at least one "amino acid alteration/mutation". In one embodiment the variant Fc-region has at least one amino acid mutation compared to a native Fc-region or to the Fc-region of a parent polypeptide, e.g. from about one to about ten amino acid mutations, and in one embodiment from about one to about five amino acid mutations in a native Fc-region or in the Fc-region of the parent polypeptide. In one embodiment the (variant) Fc-region has at least about 80% homology with a wild-type Fc-region and/or with an Fc-region of a parent polypeptide, and in one embodiment the variant Fc-region has least about 90% homology, in one embodiment the variant Fc-region has at least about 95% homology.

The variant Fc-regions as reported herein are defined by the amino acid alterations that are contained. Thus, for example, the term P329G denotes a variant Fc-region with the mutation of proline to glycine at amino acid position 329 relative to the parent (wild-type) Fc-region. The identity of the wild-type amino acid may be unspecified, in which case the aforementioned variant is referred to as 329G. For all positions discussed in the present invention, numbering is according to the EU index. The EU index or EU index as in Kabat or EU numbering scheme refers to the numbering of the EU antibody (Edelman, et al., Proc. Natl. Acad. Sci. USA 63 (1969) 78-85, hereby entirely incorporated by reference.) The alteration can be an addition, deletion, or mutation. The term "mutation" denotes a change to naturally occurring amino acids as well as a change to non-naturally occurring amino acids, see e.g. U.S. Pat. No. 6,586,207, WO 98/48032, WO 03/073238, US 2004/0214988, WO 2005/35727, WO 2005/74524, Chin, J. W., et al., J. Am. Chem. Soc. 124 (2002) 9026-9027; Chin, J. W. and Schultz, P. G., ChemBioChem 11 (2002) 1135-1137; Chin, J. W., et al., PICAS United States of America 99 (2002) 11020-11024; and, Wang, L. and Schultz, P. G., Chem. (2002) 1-10 (all entirely incorporated by reference herein).

A polypeptide chain of a wild-type human Fc-region of the IgG1 subclass has the following amino acid sequence:

(SEQ ID NO: 41)
CPPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVSN

KALPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVFSC

SVMHEALHNHYTQKSLSLSPGK.

A polypeptide chain of a variant human Fc-region of the IgG1 subclass with the mutations L234A, L235A has the following amino acid sequence:

(SEQ ID NO: 42)
CPPCPAPEAAGGPSVFLFPPKPKDTLMISRTPEVTCVVVDVSHEDPEVKF

NWYVDGVEVHNAKTKPREEQYNSTYRVVSVLTVLHQDWLNGKEYKCKVSN

KALPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVFSC

SVMHEALHNHYTQKSLSLSPGK.

A polypeptide chain of a variant human Fc-region of the IgG1 subclass with a T366S, L368A and Y407V mutation has the following amino acid sequence:

(SEQ ID NO: 43)
CPPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVSN

KALPAPIEKTISKAKGQPREPQVCTLPPSRDELTKNQVSLSCAVKGFYPS

DIAVEWESNGQPENNYKTTPPVLDSDGSFFLVSKLTVDKSRWQQGNVFSC

SVMHEALHNHYTQKSLSLSPGK.

A polypeptide chain of a variant human Fc-region of the IgG1 subclass with a T366W mutation has the following amino acid sequence:

(SEQ ID NO: 44)
CPPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVSN

KALPAPIEKTISKAKGQPREPQVYTLPPCRDELTKNQVSLWCLVKGFYPS

DIAVEWESNGQPENNYKTTPPVLDSDGSFFLYSKLTVDKSRWQQGNVFSC

SVMHEALHNHYTQKSLSLSPGK.

A polypeptide chain of a variant human Fc-region of the IgG1 subclass with a L234A, L235A and T366S, L368A and Y407V mutation has the following amino acid sequence:

(SEQ ID NO: 45)
CPPCPAPEAAGGPSVFLFPPKPKDTLMISRTPEVTCVVVDVSHEDPEVKF

NWYVDGVEVHNAKTKPREEQYNSTYRVVSVLTVLHQDWLNGKEYKCKVS

NKALPAPIEKTISKAKGQPREPQVCTLPPSRDELTKNQVSLSCAVKGFYP

SDIAVEWESNGQPENNYKTTPPVLDSDGSFFLVSKLTVDKSRWQQGNVES

CSVMHEALHNHYTQKSLSLSPGK.

A polypeptide chain of a variant human Fc-region of the IgG1 subclass with a L234A, L235A and T366W mutation has the following amino acid sequence:

(SEQ ID NO: 46)
CPPCPAPEAAGGPSVFLFPPKPKDTLMISRTPEVTCVVVDVSHEDPEVKF

NWYVDGVEVHNAKTKPREEQYNSTYRVVSVLTVLHQDWLNGKEYKCKVS

NKALPAPIEKTISKAKGQPREPQVYTLPPCRDELTKNQVSLWCLVKGFYP

SDIAVEWESNGQPENNYKTTPPVLDSDGSFFLYSKLTVDKSRWQQGNVFS

CSVMHEALHNHYTQKSLSLSPGK.

A polypeptide chain of a variant human Fc-region of the IgG1 subclass with a P329G mutation has the following amino acid sequence:

(SEQ ID NO: 47)
CPPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVSN

KALGAPIEKTISKAKGQPREPQVYTLPPSRDELTKNQVSLTCLVKGFYPS

DIAVEWESNGQPENNYKTTPPVLDSDGSFFLYSKLTVDKSRWQQGNVFSC

SVMHEALHNHYTQKSLSLSPGK.

A polypeptide chain of a variant human Fc-region of the IgG1 subclass with a L234A, L235A and P329G mutation has the following amino acid sequence:

(SEQ ID NO: 48)
CPPCPAPEAAGGPSVFLFPPKPKDTLMISRTPEVTCVVVDVSHEDPEVKF
NWYVDGVEVHNAKTKPREEQYNSTYRVVSVLTVLHQDWLNGKEYKCKVS
NKALGAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFS
CSVMHEALHNHYTQKSLSLSPGK.

A polypeptide chain of a variant human Fc-region of the IgG1 subclass with a P239G and T366S, L368A and Y407V mutation has the following amino acid sequence:

(SEQ ID NO: 49)
CPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSN
KALGAPIEKTISKAKGQPREPQVCTLPPSRDELTKNQVSLSCAVKGFYPS
DIAVEWESNGQPENNYKTTPPVLDSDGSFFLVSKLTVDKSRWQQGNVFSC
SVMHEALHNHYTQKSLSLSPGK.

A polypeptide chain of a variant human Fc-region of the IgG1 subclass with a P329G and T366W mutation has the following amino acid sequence:

(SEQ ID NO: 50)
CPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSN
KALGAPIEKTISKAKGQPREPQVYTLPPCRDELTKNQVSLWCLVKGFYPS
DIAVEWESNGQPENNYKTTPPVLDSDGSFFLYSKLTVDKSRWQQGNVFSC
SVMHEALHNHYTQKSLSLSPGK.

A polypeptide chain of a variant human Fc-region of the IgG1 subclass with a L234A, L235A, P329G and T366S, L368A and Y407V mutation has the following amino acid sequence:

(SEQ ID NO: 51)
CPPCPAPEAAGGPSVFLFPPKPKDTLMISRTPEVTCVVVDVSHEDPEVKF
NWYVDGVEVHNAKTKPREEQYNSTYRVVSVLTVLHQDWLNGKEYKCKVS
NKALGAPIEKTISKAKGQPREPQVCTLPPSRDELTKNQVSLSCAVKGFYP
SDIAVEWESNGQPENNYKTTPPVLDSDGSFFLVSKLTVDKSRWQQGNVFS
CSVMHEALHNHYTQKSLSLSPGK.

A polypeptide chain of a variant human Fc-region of the IgG1 subclass with a L234A, L235A, P329G and T366W mutation has the following amino acid sequence:

(SEQ ID NO: 52)
CPPCPAPEAAGGPSVFLFPPKPKDTLMISRTPEVTCVVVDVSHEDPEVKF
NWYVDGVEVHNAKTKPREEQYNSTYRVVSVLTVLHQDWLNGKEYKCKVS
NKALGAPIEKTISKAKGQPREPQVYTLPPCRDELTKNQVSLWCLVKGFYP
SDIAVEWESNGQPENNYKTTPPVLDSDGSFFLYSKLTVDKSRWQQGNVFS
CSVMHEALHNHYTQKSLSLSPGK.

A polypeptide chain of a wild-type human Fc-region of the IgG4 subclass has the following amino acid sequence:

(SEQ ID NO: 53)
CPSCPAPEFLGGPSVFLFPPKPKDTLMISRTPEVTCVVVDVSQEDPEVQF
NWYVDGVEVHNAKTKPREEQFNSTYRVVSVLTVLHQDWLNGKEYKCKVSN
KGLPSSIEKTISKAKGQPREPQVYTLPPSQEEMTKNQVSLTCLVKGFYPS
DIAVEWESNGQPENNYKTTPPVLDSDGSFFLYSRLTVDKSRWQEGNVFSC
SVMHEALHNHYTQKSLSLSLGK.

A polypeptide chain of a variant human Fc-region of the IgG4 subclass with a S228P and L235E mutation has the following amino acid sequence:

(SEQ ID NO: 54)
CPPCPAPEFEGGPSVFLFPPKPKDTLMISRTPEVTCVVVDVSQEDPEVQF
NWYVDGVEVHNAKTKPREEQFNSTYRVVSVLTVLHQDWLNGKEYKCKVSN
KGLPSSIEKTISKAKGQPREPQVYTLPPSQEEMTKNQVSLTCLVKGFYPS
DIAVEWESNGQPENNYKTTPPVLDSDGSFFLYSRLTVDKSRWQEGNVFSC
SVMHEALHNHYTQKSLSLSLGK.

A polypeptide chain of a variant human Fc-region of the IgG4 subclass with a S228P, L235E and P329G mutation has the following amino acid sequence:

(SEQ ID NO: 55)
CPPCPAPEFEGGPSVFLFPPKPKDTLMISRTPEVTCVVVDVSQEDPEVQF
NWYVDGVEVHNAKTKPREEQFNSTYRVVSVLTVLHQDWLNGKEYKCKVSN
KGLGSSIEKTISKAKGQPREPQVYTLPPSQEEMTKNQVSLTCLVKGFYPS
DIAVEWESNGQPENNYKTTPPVLDSDGSFFLYSRLTVDKSRWQEGNVFSC
SVMHEALHNHYTQKSLSLSLGK.

The term "Fc receptor", short "FcR", denotes a receptor that binds to an Fc-region. In one embodiment the FcR is a native sequence human FcR. Moreover, in one embodiment the FcR is an FcR which binds an IgG antibody (an Fc gamma receptor) and includes receptors of the FcγRI, FcγRII, and FcγRIII subclasses, including allelic variants and alternatively spliced forms thereof. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see e.g. Daeron, M., Annu. Rev. Immunol. 15 (1997) 203-234). FcRs are reviewed in Ravetch and Kinet, Annu. Rev. Immunol. 9 (1991) 457-492, Capel, et al., Immunomethods 4 (1994) 25-34, de Haas, et al., J. Lab. Clin. Med. 126 (1995) 330-341. Other FcRs, including those to be identified in the future, are encompassed by the term "FcR" herein. The term also includes the neonatal receptor, FcRn, which is responsible for the transfer of maternal IgGs to the fetus (see e.g. Guyer, et al., J. Immunol. 117 (1976) 587; Kim, et al., J. Immunol. 24 (1994) 249).

The term "Fc gamma receptor", short "FcγR", denotes any member of the family of proteins that bind the IgG antibody Fc-region and is encoded by an FcγR gene. In humans this family includes but is not limited to FcγRI (CD64), including isoforms FcγRIA, FcγRIB, and FcγRIC, FcγRII (CD32), including isoforms FcγRIIA (including allotypes H131 and R131), FcγRIIB (including FcγRIIB-1 and FcγRIIB-2), and FcγRIIC, and FcγRIII (CD16), including isoforms FcγRIIIA (including allotypes V158 and F158) and FcγRIIIB (including allotypes FcγRIIB-NA1 and FcγRIIB-NA2) (see e.g. Jefferis, et al., Immunol. Lett. 82 (2002) 57-65, entirely incorporated by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes. The Fc-region-FcγR interaction involved amino acid residues are 234-239 (lower hinge region), 265-269 (B/C loop), 297-299 (D/E loop), and 327-332 (F/G) loop (Sondermann, et al., Nature 406 (2000) 267-273).

Amino acid mutations that result in a decreased binding/affinity for the FcγRI, FcγRIIA, FcγRIIB, and/or FcγRIIIA include N297A (concomitantly with a decreased immunogenicity and prolonged half-life binding/affinity) (Routledge, et al., Transplantation 60 (1995) 847; Friend, et al., Transplantation 68 (1999) 1632; Shields, et al., J. Biol. Chem. 276 (2001) 6591-6604), residues 233-236 (Ward and Ghetie, Ther. Immunol. 2 (1995) 77; Armour, et al., Eur. J. Immunol. 29 (1999) 2613-2624). Some exemplary amino acid substitutions are described in U.S. Pat. Nos. 7,355,008 and 7,381,408.

The term "neonatal Fc Receptor", short "FcRn", denotes a protein that binds the IgG antibody Fc-region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin. The interacting amino acid residues of the Fc-region with the FcRn are near the junction of the CH2 and CH3 domains. The Fc-region-FcRn contact residues are all within a single IgG heavy chain. The involved amino acid residues are 248, 250-257, 272, 285, 288, 290-291, 308-311, and 314 (all in the CH2 domain) and amino acid residues 385-387, 428, and 433-436 (all in the CH3 domain) Amino acid mutations that result in an increased binding/affinity for the FcRn include T256A, T307A, E380A, and N434A (Shields, et al., J. Biol. Chem. 276 (2001) 6591-6604).

The term "full length antibody" denotes an antibody that has a structure and amino acid sequence substantially identical to a native antibody structure as well as polypeptides that comprise the Fc-region as reported herein.

The term "full length antibody heavy chain" denotes a polypeptide comprising in N- to C-terminal direction an antibody variable domain, a first constant domain, an antibody heavy chain hinge region, a second constant domain, and a third constant domain.

The term "full length antibody light chain" denotes a polypeptide comprising in N- to C-terminal direction an antibody variable domain and a constant domain.

The term "hinge region" denotes the part of an antibody heavy chain polypeptide that joins in a wild-type antibody heavy chain the CH1 domain and the CH2 domain, e. g. from about position 216 to about position 230 according to the EU number system of Kabat, or from about position 226 to about position 230 according to the EU number system of Kabat. The hinge regions of other IgG subclasses can be determined by aligning with the hinge-region cysteine residues of the IgG1 subclass sequence.

The hinge region is normally a dimeric molecule consisting of two polypeptides with identical amino acid sequence. The hinge region generally comprises about 25 amino acid residues and is flexible allowing the antigen binding regions to move independently. The hinge region can be subdivided into three domains: the upper, the middle, and the lower hinge domain (see e.g. Roux, et al., J. Immunol. 161 (1998) 4083).

In one embodiment the hinge region has the amino acid sequence DKTHTCPX4CP (SEQ ID NO: 56), wherein X4 is either S or P. In one embodiment the hinge region has the amino acid sequence HTCPX4CP (SEQ ID NO: 57), wherein X4 is either S or P. In one embodiment the hinge region has the amino acid sequence CPX4CP (SEQ ID NO: 58), wherein X4 is either S or P.

The term "lower hinge region" of an Fc-region denotes the stretch of amino acid residues immediately C-terminal to the hinge region, i.e. residues 233 to 239 of the Fc-region according to the EU numbering of Kabat.

The term "wild-type Fc-region" denotes an amino acid sequence identical to the amino acid sequence of an Fc-region found in nature. Wild-type human Fc-regions include a native human IgG1 Fc-region (non-A and A allotypes), native human IgG2 Fc-region, native human IgG3 Fc-region, and native human IgG4 Fc-region as well as naturally occurring variants thereof.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "position" denotes the location of an amino acid residue in the amino acid sequence of a polypeptide. Positions may be numbered sequentially, or according to an established format, for example the EU index of Kabat for antibody numbering.

The term "altered" FcR binding affinity or ADCC activity denotes a polypeptide that has either enhanced or diminished FcR binding activity and/or ADCC activity compared to a parent polypeptide (e.g. a polypeptide comprising a wild-type Fc-region). The variant polypeptide which "has increased binding" to an FcR binds at least one FcR with lower dissociation constant (i.e. better/higher affinity) than the parent or wild-type polypeptide. The polypeptide variant which "has decreased binding" to an FcR, binds at least one FcR with higher dissociation constant (i.e. worse/lower affinity) than the parent or a wild-type polypeptide. Such variants which display decreased binding to an FcR may possess little or no appreciable binding to an FcR, e.g., 0-20% binding to the FcR compared to a wild-type or parent IgG Fc-region.

The polypeptide which binds an FcR with "reduced affinity" in comparison with a parent or wild-type polypeptide, is a polypeptide which binds any one or more of the above identified FcRs with (substantially) reduced binding affinity compared to the parent polypeptide, when the amounts of polypeptide variant and parent polypeptide in the binding assay are (essentially) about the same. For example, the polypeptide variant with reduced FcR binding affinity may display from about 1.15 fold to about 100 fold, e.g. from about 1.2 fold to about 50 fold reduction in FcR binding affinity compared to the parent polypeptide, where FcR binding affinity is determined.

The polypeptide comprising a variant Fc-region which "mediates antibody-dependent cell-mediated cytotoxicity (ADCC) in the presence of human effector cells less effectively" than a parent polypeptide is one which in vitro or in vivo is (substantially) less effective at mediating ADCC, when the amounts of variant polypeptide and parent polypeptide used in the assay are (essentially) about the same. Generally, such variants will be identified using the in vitro ADCC assay as disclosed herein, but other assays or methods for determining ADCC activity, e.g. in an animal model etc., are contemplated. In one embodiment the variant is from about 1.5 fold to about 100 fold, e.g. from about two fold to about fifty fold, less effective at mediating ADCC than the parent, e.g. in the in vitro assay disclosed herein.

The term "receptor" denotes a polypeptide capable of binding at least one ligand. In one embodiment the receptor is a cell-surface receptor having an extracellular ligand-binding domain and, optionally, other domains (e.g. transmembrane domain, intracellular domain and/or membrane anchor). The receptor to be evaluated in the assay described herein may be an intact receptor or a fragment or derivative thereof (e.g. a fusion protein comprising the binding domain of the receptor fused to one or more heterologous polypeptides). Moreover, the receptor to be evaluated for its binding properties may be present in a cell or isolated and optionally coated on an assay plate or some other solid phase.

The term "pharmaceutical formulation" denotes a preparation which is in such form as to permit the biological activity of an active ingredient contained therein to be effective, and which contains no additional components which are unacceptably toxic to a subject to which the formulation would be administered.

A "pharmaceutically acceptable carrier" denotes an ingredient in a pharmaceutical formulation, other than an active ingredient, which is nontoxic to a subject. A pharmaceutically acceptable carrier includes, but is not limited to, a buffer, excipient, stabilizer, or preservative.

II. Method for Producing an Antibody Fc-Region Conjugate as Reported Herein

Herein is reported a method for producing an antibody Fc-region conjugate comprising an antibody Fc-region and a binding entity that specifically binds to a target comprising the following step:

incubating i) a binding entity that specifically binds to a target comprising the amino acid sequence $G_n$SLPX1TG (SEQ ID NO: 02, n=1, 2, or 3, X1 can be any amino acid residue) within the 20 C-terminal amino acid residues, and ii) an antibody Fc-region comprising an oligoglycine ($G_m$; m=1, 2, or 3) at least at one N-terminus with the enzyme Sortase A and thereby producing the antibody Fc-region conjugate.

The invention is based on the finding that a conjugate comprising an antibody Fc-region and a binding entity that specifically binds to a target can be obtained in high yield in an enzymatic conjugation by using (i) a binding entity that specifically binds to a target comprising the amino acid sequence $G_n$SLPX1TG (SEQ ID NO: 02, n=1, 2, or 3, and wherein X1 can be any amino acid residue) in its C-terminal region, (ii) an antibody Fc-region comprising an oligoglycine ($G_m$; m=1, 2, or 3) at least at one of its N-termini, and (iii) the enzyme Sortase A.

With this combination of reagents i) the reverse reaction recognizing the LPX1TG (SEQ ID NO: 01) amino acid sequence within the product conjugate as substrate, and/or ii) the generation of a dead-end hydrolysis polypeptide fragment (polypeptide with without/cleaved LPX1TG (SEQ ID NO: 01) recognition sequence generated through cleavage of the thioacyl-binding entity Sortase A intermediate by water instead by the $G_m$-antibody Fc-region nucleophile)

that is normally occurring at increased reaction times can be reduced or even eliminated.

Figure 3:
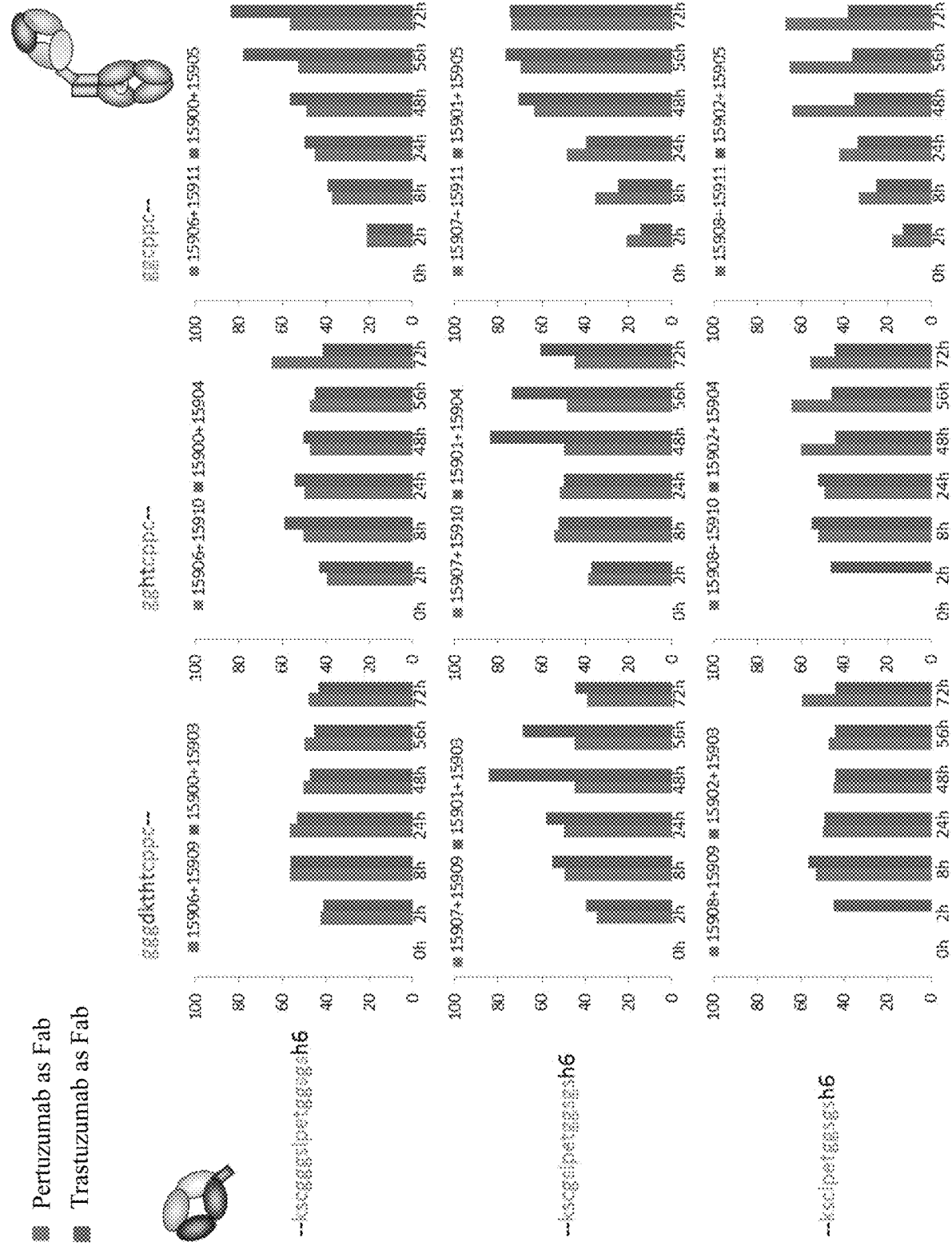
FIG. 3 Comparison of the conversion of the Sortase A catalyzed conjugation of two Fab antibody fragments with different binding specificity containing three different C-terminal amino acid sequences at the VH—CH1 heavy chain Fab fragment (LPETGGSGSHHHHHH (SEQ ID NO: 14), GSLPETGGSGSHHHHHH (SEQ ID NO: 15) and GGGSL-PETGGSGSHHHHHH (SEQ ID NO: 16), respectively) with three different one armed antibody Fc-regions (OA-Fc antibodies) containing three N-terminally different Fc-chains (GGCPPC (SEQ ID NO: 17), GGHTCPPC (SEQ ID NO: 18), and GGGDKTHTCPPC (SEQ ID NO: 19), respectively).
Figure 4:
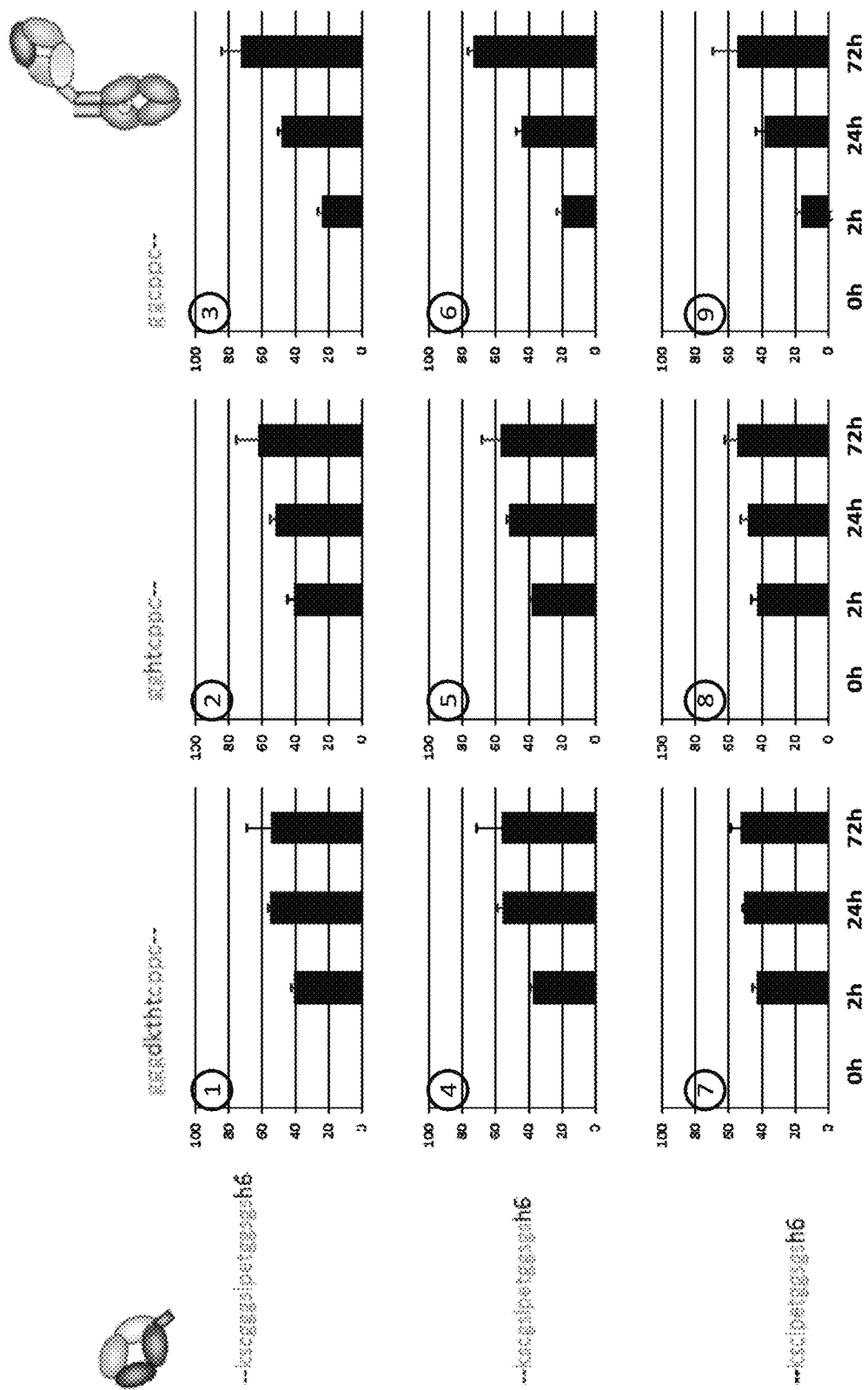
FIG. 4 Comparison of the conversion of the Sortase A catalyzed conjugation of two Fab antibody fragments with different binding specificity containing three different C-terminal amino acid sequences at the VH—CH1 heavy chain Fab fragment with three different one armed antibody Fc-regions (OA-Fc antibodies) containing three N-terminally different Fc-chains reduced to four time points wherein the values for all combinations are averaged in order to obtain binding specificity independent (i.e. Fab independent) values wherein the differences are only based on the different combinations. Each value comprises four measurements.

Different combinations of C-terminal and N-terminal amino acid sequence combinations have been tested (see e.g. FIG. 3).

In more detail, as an exemplary binding entity an antibody Fab fragment was used and as exemplary antibody Fc-region a one armed antibody Fc-region (OA-Fc-region=a pair of a full length antibody heavy chain and its cognate light chain and an heavy chain antibody Fc-region polypeptide) was used. Three different sequences at the C-terminus of the antibody Fab fragment VH—CH1 heavy chain and at the N-terminus of the OA-Fc-region respectively were conjugated using the exemplary transpeptidase Sortase A. Nine different conjugates were obtained. The progress/efficiency of the coupling reaction was determined at different time points. To this end aliquots of the transpeptidation reactions were analyzed by SDS-PAGE. The efficiency of ligation at 72 h reaction time was estimated densitometrically from the gel. The results are given in the following Table 1.

TABLE 1

| Fab VH-CH1 heavy chain | One armed antibody Fc-region (OA-Fc-region) | | |
|---|---|---|---|
| | GGGDKTHTCPPC (SEQ ID NO: 19) | GGHTCPPC (SEQ ID NO: 18) | GGCPPC (SEQ ID NO: 17) |
| KSCGGGSLPETGGSGSHHHHHH (SEQ ID NO: 75) | approx. 0.54% | approx. 0.62% | approx. 0.73% |
| KSCGSLPETGGSGSHHHHHH (SEQ ID NO: 76) | approx. 0.56% | approx. 0.56% | approx. 0.73% |
| KSCLPETGGSGSHHHHHH (SEQ ID NO: 77) | approx. 0.52% | approx. 0.54% | approx. 0.54% |

The three amino acid residues KSC are the last three C-terminal amino acid residues of the CH1 domain.

It can be seen that by using the C-terminal amino acid sequences GSLPX1TG (SEQ ID NO: 2 with n=1 and wherein X1 can be any amino acid residue) and GGGSLPX1TG (SEQ ID NO: 2 with n=3 and wherein X1 can be any amino acid residue) in the C-terminal region of the Fab VH—CH1 heavy chain fragment the best yields in combination with the N-terminal amino acid sequence GGCPPC (SEQ ID NO: 07 wherein X4 is P, SEQ ID NO: 17) of the antibody Fc-region can be obtained.

In one embodiment the binding entity that specifically binds to a target comprises the amino acid sequence $G_n$SLPX1TGGSGS (SEQ ID NO: 03, n=1, 2 or 3 and wherein X1 can be any amino acid residue) within the 20 C-terminal amino acid residues.

In one embodiment the binding entity that specifically binds to a target comprises the amino acid sequence X2GSLPX1TGGSGS (SEQ ID NO: 04, wherein X1 can be any amino acid residue) within the 20 C-terminal amino acid residues, whereby X2 can be any amino acid residue except glycine.

In one embodiment the binding entity that specifically binds to a target comprises the amino acid sequence $G_n$SLPX1TGGSGSX3 (SEQ ID NO: 05, n=1, 2 or 3 and wherein X1 can be any amino acid residue) within the 20 C-terminal amino acid residues, whereby X3 is an amino acid sequence tag.

In one embodiment the binding entity that specifically binds to a target comprises the amino acid sequence X2GSLPX1TGGSGSX3 (SEQ ID NO: 06, wherein X1 can be any amino acid residue) within the 20 C-terminal amino acid residues, whereby X2 can be any amino acid residue except glycine, and X3 is an amino acid sequence tag.

In one embodiment at least one of the N-termini of the antibody Fc-region comprises two glycine residues.

In one embodiment the antibody Fc-region comprises the amino acid sequence GGCPPC (SEQ ID NO: 17) at least at one of its N-termini.

In one embodiment the binding entity that specifically binds to a target is an antigen binding single chain polypeptide (scFv, scFab, darpin, single domain antibodies derived from humans, camels or sharks) or a an antigen binding multi chain polypeptide (Fab, dsFv or diabody). In one embodiment the binding entity that specifically binds to a target is a Fab or a scFv.

In one embodiment the antibody Fc-region comprises a first (antibody heavy chain) and a second polypeptide ($G_m$-Fc-region, m=1, 2, or 3, or 4, or 5) chain covalently linked by at least one disulfide bond.

In one embodiment the antibody Fc-region comprises a first polypeptide chain that is a full length antibody heavy chain and a second polypeptide chain that is a modified $G_m$-Fc-region (m=1, 2, or 3, or 4, or 5) heavy chain fragment which are covalently linked by at least one disulfide bond.

In one embodiment the binding entity that specifically binds to a target specifically binds to a first epitope or antigen and the full length antibody heavy chain when paired with the corresponding cognate full length light chain specifically binds to a second epitope or antigen that is different from the first epitope or antigen.

One aspect as reported herein is an antibody Fc-region conjugate obtained by a method as reported herein.

One aspect as reported herein is an antibody Fc-region conjugate comprising the amino acid sequence $G_n$SLPX1TGG (SEQ ID NO: 09, n=1, 2 or 3 and wherein X1 can be any amino acid residue).

In one embodiment the antibody Fc-region conjugate comprises the amino acid sequence $G_n$SLPX1TGGCPX4C (SEQ ID NO: 10, n=1, 2 or 3), wherein X1 can be any amino acid residue, and wherein X4 is P) within the 20 C-terminal amino acid residues.

In one embodiment the antibody Fc-region conjugate comprises the amino acid sequence $G_n$SLPX1TGGHTCPX4C (SEQ ID NO: 12, n=1, 2 or 3), wherein X1 can be any amino acid residue, and wherein X4 is P) within the 20 C-terminal amino acid residues.

In one embodiment the antibody Fc-region conjugate comprises the amino acid sequence X2GSLPX1TGGCPX4C (SEQ ID NO: 11, wherein X1 can be any amino acid residue, wherein X4 is P) within the 20 C-terminal amino acid residues whereby X2 can be any amino acid residue except glycine.

In one embodiment the antibody Fc-region conjugate comprises the amino acid sequence X2GSLPX1TGGCPX4C (SEQ ID NO: 11, wherein X1 can be any amino acid residue, wherein X4 is P) within the 20 C-terminal amino acid residues whereby X2 can be any amino acid residue except glycine.

In one embodiment the antibody Fc-region conjugate comprises a second binding entity that specifically binds to a target.

In one embodiment the binding entity that specifically binds to a target is a Fab or a scFv.

In one embodiment the antibody Fc-region conjugate comprises a first and a second polypeptide chain that are covalently linked by at least one disulfide bond.

In one embodiment the antibody Fc-region conjugate comprises a first polypeptide chain that is a full length antibody heavy chain and a second antibody heavy chain Fc-region polypeptide that comprises the amino acid sequence $G_n$SLPX1TGGCPPC (SEQ ID NO: 10, n=1, 2 or 3, wherein X1 can be any amino acid residue, and wherein X4 is P), whereby the first and second polypeptide chain are covalently linked by at least one disulfide bond.

In one embodiment the antibody Fc-region comprises a full length antibody heavy chain paired with the cognate full length light chain and binds specifically to a first epitope or antigen and the binding entity conjugated to the antibody Fc-region binds to a second epitope or antigen that is different from the first epitope or antigen.

In one embodiment of all aspects X1 is E.

In one embodiment of all aspects as reported herein the antibody Fc-region is of human origin.

By the combination of two mutations at defined positions in the antibody Fc-region a complete reduction of the Fc-region associated effector function can be achieved.

The selection of an effector function eliciting Fc-region is dependent on the intended use of the antibody Fc-region conjugate.

If the desired use is the functional neutralization of a soluble target a non-effector function eliciting subclass or variant should be selected.

If the desired use is the removal of a target an effector function eliciting subclass or variant should be selected.

If the desired use is the antagonization of a cell-bound target a non-effector function eliciting subclass or variant should be selected.

If the desired use is the removal of a target presenting cell an effector function eliciting subclass or variant should be selected.

The circulating half-life of an antibody or antibody Fc-region conjugate can be influenced by modulating the Fc-region-FcRn interaction.

The minimization or even removal of antibody-dependent cell-mediated cytotoxicity (ADCC) and complement-dependent cytotoxicity (CDC) can be achieved by so called hinge-region amino acid changes/substitutions.

The minimization or even removal of the activation of the classical complement cascade can be achieved by so called hinge-region amino acid changes/substitutions.

An increase of the circulatory half-life of an antibody or antibody Fc-region conjugate can be achieved by increased binding to the neonatal Fc receptor and results in an improved efficacy, a reduced dose or frequency of administration, or an improved delivery to the target. A reduction of the circulatory half-life of an antibody or antibody Fc-region conjugate can be achieved by reduced binding to the neonatal Fc receptor and results in a reduced whole body exposure or an improved target-to-non-target binding ratio.

Generally, the method as reported herein is applicable to the production of antibody Fc-region conjugates comprising either a wild-type Fc-region or an altered/variant Fc-region.

In one embodiment the Fc-region is a human Fc-region.

In one embodiment the Fc-region is "conceptual" and, while it does not physically exist, the antibody engineer may decide upon a variant Fc-region to be used.

In one embodiment the nucleic acid encoding the Fc-region part of the antibody Fc-region conjugate is altered to generate a variant nucleic acid sequence encoding the variant Fc-region part of the antibody Fc-region conjugate.

The nucleic acid encoding the amino acid sequence of the Fc-region part of the antibody Fc-region conjugate can be prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the polypeptides of the antibody Fc-region conjugate.

The Fc-region interacts with a number of receptors or ligands including but not limited to Fc receptors (e.g. FcγRI, FcγRIIA, FcγRIIIA), the complement protein C1q, and other molecules such as proteins A and G. These interactions are essential for a variety of effector functions and downstream signaling events including, but not limited to, antibody dependent cell-mediated cytotoxicity (ADCC), antibody dependent cellular phagocytosis (ADCP) and complement dependent cytotoxicity (CDC).

In one embodiment the antibody Fc-region conjugate (as produced with the method as reported herein) has at least one or more of the following properties: reduced or ablated effector function (ADCC and/or CDC and/or ADCP), reduced or ablated binding to Fc receptors, reduced or ablated binding to C1q, or reduced or ablated toxicity.

In one embodiment the antibody Fc-region conjugate (as produced with the method as reported herein) comprises a wild-type Fc-region that has at least two amino acid mutations, additions, or deletions.

In one embodiment the antibody Fc-region conjugate (as produced with the method as reported herein) has a reduced affinity to a human Fc receptor (FcγR) and/or a human complement receptor compared to an antibody or antibody Fc-region conjugate comprising a wild-type human Fc-region.

In one embodiment the antibody Fc-region conjugate (as produced with the method as reported herein) comprises an Fc-region that has a reduced affinity to a human Fc receptor (FcγR) and/or human complement receptor compared to an antibody or antibody Fc-region conjugate comprising a wild-type human Fc-region.

In one embodiment the antibody Fc-region conjugate (as produced with the method as reported herein) has reduced affinity to at least one of FcγRI, FcγRII, and/or FcγRIIIA In one embodiment the affinity to FcγRI and FcγRIIIA is reduced. In one embodiment the affinity to FcγRI, FcγRII and FcγRIIIA is reduced.

In one embodiment the affinity to FcγRI, FcγRIIIA and C1q is reduced.

In one embodiment the affinity to FcγRI, FcγRII, FcγRIIIA and C1q is reduced.

In one embodiment the antibody Fc-region conjugate (as produced with the method as reported herein) has a reduced ADCC compared to an antibody or antibody Fc conjugate comprising a wild-type Fc-region. In one embodiment the ADCC is reduced by at least 20% compared to the ADCC induced by an Fc-region fusion polypeptide or conjugate comprising a wild-type Fc-region.

In one embodiment the antibody Fc-region conjugate (as produced with the method as reported herein) has an ADCC and CDC induced by the Fc-region that is decreased or ablated compared to an antibody Fc-region conjugate comprising a wild-type Fc-region.

In one embodiment the antibody Fc-region conjugate (as produced with the method as reported herein) has a decreased ADCC, CDC, and ADCP compared to an OA-Fc-region conjugate comprising a wild-type Fc-region.

In one embodiment the antibody Fc-region conjugate comprises at least one amino acid substitution in the Fc-region that is selected from the group comprising S228P, E233P, L234A, L235A, L235E, N297A, N297D, P329G, and P331S.

In one embodiment the wild-type Fc-region is a human IgG1 Fc-region or a human IgG4 Fc-region.

In one embodiment the antibody Fc-region comprises besides a mutation of the amino acid residue proline at position 329 at least one further addition, mutations, or deletion of an amino acid residue in the Fc-region that is correlated with increased stability of the antibody Fc-region conjugate.

In one embodiment the further addition, mutation, or deletion of an amino acid residue in the Fc-region is at position 228 and/or 235 of the Fc-region if the Fc-region is of IgG4 subclass. In one embodiment the amino acid residue serine at position 228 and/or the amino acid residue leucine at position 235 is/are substituted by another amino acid. In one embodiment the antibody Fc-region conjugate comprises a proline residue at position 228 (mutation of the serine residue to a proline residue). In one embodiment the antibody Fc-region conjugate comprises a glutamic acid residue at position 235 (mutation of the leucine residue to a glutamic acid residue).

In one embodiment the Fc-region comprises three amino acid mutations. In one embodiment the three amino acid mutations are P329G, S228P and L235E mutation (P329G/SPLE).

In one embodiment the further addition, mutation, or deletion of an amino acid residue in the Fc-region is at position 234 and/or 235 of the Fc-region if the Fc-region is of IgG1 subclass. In one embodiment the amino acid residue leucine at position 234 and/or the amino acid residue leucine at position 235 is/are mutated to another amino acid.

In one embodiment the Fc-region comprises an amino acid mutation at position 234, wherein the leucine amino acid residue is mutated to an alanine amino acid residue.

In one embodiment the Fc-region comprises an amino acid mutation at position 235, wherein the leucine amino acid residue is mutated to a serine amino acid residue.

In one embodiment the Fc-region comprises an amino acid mutation at position 329, wherein the proline amino acid residue is mutated to a glycine amino acid residue, an amino acid mutation at position 234, wherein the leucine amino acid residue is mutated to an alanine amino acid residue, and an amino acid mutation at position 235, wherein the leucine amino acid residue is mutated to an alanine amino acid residue.

Fc-region variants with increased affinity for FcRn have longer serum half-lives, and such molecules will have useful applications in methods of treating mammals where long systemic half-life of the administered antibody Fc-region conjugate is desired, e.g., to treat a chronic disease or disorder.

Antibody Fc-region conjugates with decreased FcRn binding affinity have shorter serum half-lives, and such molecules will have useful applications in methods of treating mammals where a shorter systemic half-life of the administered antibody Fc-region conjugate is desired, e.g. to avoid toxic side effects or for in vivo diagnostic imaging applications. Fc-region fusion polypeptides or conjugates with decreased FcRn binding affinity are less likely to cross the placenta, and thus may be utilized in the treatment of diseases or disorders in pregnant women.

Fc-regions with altered binding affinity for FcRn is in one embodiment an Fc-region with an amino acid alteration at one or more of the amino acid positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439, and/or 447.

The Fc-region is in one embodiment an Fc-region with one or more amino acid alterations at the amino acid positions 252, 253, 254, 255, 288, 309, 386, 388, 400, 415, 433, 435, 436, 439, and/or 447.

Fc-regions which display increased binding to FcRn comprise in one embodiment one or more amino acid alterations at the amino acid positions 238, 256, 265, 272, 286, 303, 305, 307, 311, 312, 317, 340, 356, 360, 362, 376, 378, 380, 382, 413, 424, and/or 434.

In one embodiment the Fc-region is an Fc-region of the IgG1 subclass and comprises the amino acid mutations P329G, and/or L234A and L235A.

In one embodiment the Fc-region is an Fc-region of the IgG4 subclass and comprises the amino acid mutations P329G, and/or S228P and L235E.

In one embodiment the antibody Fc-region comprises the mutation T366W in the first heavy chain Fc-region polypeptide and the mutations T366S, L368A and Y407V in the second heavy chain Fc-region polypeptide, wherein the numbering is according to the EU index of Kabat.

In one embodiment the antibody Fc-region comprises the mutation S354C in the first heavy chain Fc-region polypeptide and the mutation Y349C in the second heavy chain Fc-region polypeptide.

Enzymatic Conjugation Using Sortase A

An antibody Fc-region conjugate comprising one or more, e.g. one, or two, or three, or four, binding entities can be obtained by Sortase A mediated ligation in vitro of e.g. an antibody Fc-region and a single chain antigen binding polypeptide (e.g. scFv, scFab or darpin) or a multi chain antigen binding complex (e.g. dsFv or Fab).

Many gram-positive bacteria use sortase to covalently anchor a variety of surface proteins including virulence factors to their cell wall (peptidoglycan). Sortases are extracellular membrane associated enzymes. The wild-type *Staphylococcus aureus* Sortase A (SrtA) is a polypeptide of 206 amino acids with an N-terminal membrane-spanning region. In a first step, sortase A recognizes substrate proteins that contain a LPX1TG (SEQ ID NO: 01) amino acid sequence motif and cleaves the amide bond between the Thr and Gly by means of an active-site Cys. This peptide cleaving reaction results in a sortase A thioester intermediate. In a second step the thioester acyl-enzyme intermediate is resolved by nucleophilic attack of an amino group of oligoglycine containing second substrate polypeptide (corresponding to the pentaglycine unit of peptidoglycan in *S. aureus*) leading to a covalently linked cell wall protein and the regeneration of sortase A. In the absence of oligoglycine nucleophiles, the acyl-enzyme intermediate is hydrolyzed by a water molecule.

Sortase-mediated ligation/conjugation has begun to be applied for a variety of protein engineering and bioconjugation purposes. This new technique enables the introduction of natural and unnatural functionalities into LPX1TG (SEQ ID NO: 01)-tagged recombinant or chemically synthesized polypeptides. Examples include the covalent attachment of oligoglycine derivatized polymers (e.g. PEG), fluorophores, vitamins (e.g. biotin and folate) lipids, carbohydrates, nucleic acids, synthetic peptides and proteins (e.g. GFP) (Tsukiji, S. and Nagamune, T., ChemBioChem 10 (2009) 787-798; Popp, M. W.-L. and Ploegh, H. L., Angew. Chem. Int. Ed. 50 (2011) 5024-5032).

It has been shown that a triglycine and even a diglycine motif of the amino component is sufficient for the SrtA-mediated ligation step (Clancy, K. W., et al., Peptide Science 94 (2010) 385-396).

For the enzymatic conjugation a soluble truncated sortase A lacking the membrane-spanning region (SrtA; amino acid residues 60-206 of *Staphylococcus aureus* SrtA) can be used (Ton-That, H., et al., Proc. Natl. Acad. Sci. USA 96 (1999) 12424-12429; Ilangovan, H., et al., Proc. Natl. Acad. Sci. USA 98 (2001) 6056-6061). The truncated soluble sortase A variant can be produced in *E. coli*.

The antibody Fc-region comprising an oligoglycine at least at one of its N-termini ($G_m$, m=1, 2, or 3, or 4, or 5) can be expressed and purified from the supernatant of eukaryotic cells (e.g. HEK293 cells, CHO cells).

The binding entity (e.g. a single chain antigen binding polypeptide such as a scFv, a scFab, or a darpin, or a multi chain antigen binding polypeptide such as a dsFv or a Fab) comprising the SrtA recognition motif at the C-terminus of one polypeptide chain can be expressed and purified from the supernatant of eukaryotic cells (e.g. HEK293 cells, CHO cells).

One aspect as reported herein is an antibody Fc-region conjugate that is obtained by conjugating a binding entity to an antibody Fc region (Gm-Fc-region) using the enzyme Sortase A, wherein a sortase recognition sequence is located in the C-terminal region of the binding entity, and wherein an oligoglycine ($G_m$; m=1, 2, or 3, or 4, or 5) is located at the N-terminus of at least one chain of the antibody Fc-region-chain.

One aspect as reported herein is a pharmaceutical formulation comprising the antibody Fc-region conjugate as reported herein and optionally a pharmaceutically acceptable carrier.

One aspect as reported herein is an antibody Fc-region conjugate as reported herein for use as a medicament.

One aspect as reported herein is the use of an antibody Fc-region conjugate as reported herein in the manufacture of a medicament.

III. Recombinant Methods

The ligation components of an antibody Fc-region conjugate, in particular, a one-armed antibody variant (OA-Fc-region-$G_m$, with m=1, or 2, or 3) and a single chain antigen binding polypeptide (e.g. scFv, scFab or darpin) or a multi chain antigen binding complex (e.g. dsFv or Fab) may be produced using recombinant methods and compositions, see e.g. U.S. Pat. No. 4,816,567.

In one aspect a method of making an antibody Fc-region conjugate is provided, wherein the method comprises (i) culturing a first host cell comprising a nucleic acid encoding the antibody Fc-region part of the conjugate under conditions suitable for expression/secretion of the antibody Fc-region and optionally recovering the antibody Fc-region part from the host cell (or host cell culture medium), and (ii) culturing a second host cell comprising a nucleic acid encoding the binding entity part of the conjugate under conditions suitable for expression/secretion of the binding entity and optionally recovering the binding entity part from the host cell (or host cell culture medium), and (iii) conjugating the recombinantly produced parts enzymatically using Sortase A mediated transpeptidation.

For recombinant production of the antibody Fc-region part of the antibody Fc-region conjugate and the binding entity part, a nucleic acid encoding the antibody Fc-region part and the binding entity part of the conjugate, e.g., as described above, is isolated and inserted into one or more vectors for further cloning and/or expression/secretion in a host cell. Such nucleic acid may be readily isolated and/or produced using conventional procedures.

Suitable host cells for cloning or expression/secretion of polypeptide-encoding vectors include prokaryotic or eukaryotic cells described herein. For example, polypeptides may be produced in bacteria, in particular when glycosylation and Fc effector function are not needed (see, e.g., U.S. Pat. Nos. 5,648,237, 5,789,199, and 5,840,523, Charlton, Methods in Molecular Biology 248 (2003) 245-254 (B.K.C. Lo, (ed.), Humana Press, Totowa, N.J.), describing expression of antibody fragments in *E. coli*.). After expression, the polypeptide may be isolated from the bacterial cell paste in a soluble fraction or may be isolated from the insoluble fraction so called inclusion bodies which can be solubilized and refolded to bioactive forms. Thereafter the polypeptide can be further purified.

In addition to prokaryotes, eukaryotic microbes such as filamentous fungi or yeasts are suitable cloning or expression hosts for polypeptide-encoding vectors, including fungi and yeast strains whose glycosylation pathways have been "humanized", resulting in the production of a polypeptide with a partially or fully human glycosylation pattern (see e.g. Gerngross, Nat. Biotech. 22 (2004) 1409-1414, and Li, et al., Nat. Biotech. 24 (2006) 210-215).

Suitable host cells for the expression of glycosylated polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts (see, e.g., U.S. Pat. Nos. 5,959,177, 6,040,498, 6,420,548, 7,125,978, and 6,417,429 (describing PLANTIBODIES™ technology for producing antibodies in transgenic plants)).

Vertebrate cells may also be used as hosts. For example, mammalian cell lines that are adapted to grow in suspension may be useful. Other examples of useful mammalian host cell lines are the COS-7 cell line (monkey kidney CV1 cell transformed by SV40; the HEK293 cell line (human embryonic kidney) BHK cell line (baby hamster kidney); the TM4 mouse sertoli cell line (TM4 cells as described, e.g., in Mather, Biol. Reprod. 23 (1980) 243-251); the CV1 cell line (monkey kidney cell); the VERO-76 cell line (African green monkey kidney cell); the HELA cell line (human cervical carcinoma cell); the MDCK cell line (canine kidney cell); the BRL-3A cell line (buffalo rat liver cell); the W138 cell line (human lung cell); the HepG2 cell line (human liver cell); the MMT 060562 cell line (mouse mammary tumor cell); the TRI cell line, as described, e.g., in Mather, et al., Annals N.Y. Acad. Sci. 383 (1982) 44-68; the MRCS cell line; and FS4 cell-s line. Other useful mammalian host cell lines include the CHO cell line (Chinese hamster ovary cell), including DHFR negative CHO cell lines (Urlaub, et al., Proc. Natl. Acad. Sci. USA 77 (1980) 4216), and myeloma cell lines such as Y0, NS0 and Sp2/0 cell line. For a review of certain mammalian host cell lines suitable for polypeptide production, see, e.g., Yazaki, and Wu, Methods in Molecular Biology, Antibody Engineering 248 (2004) 255-268 (B.K.C. Lo, (ed.), Humana Press, Totowa, N.J.).

Description of the Sequence Listing:
SEQ ID NO: 01 to 06 Sortase motifs
SEQ ID NO: 07 to 08 Fc-region nucleophiles
SEQ ID NO: 09 to 13 Sortase motif remainders in the antibody Fc-region conjugate
SEQ ID NO: 14 to 16 Exemplary binding entity C-terminal amino acid sequences
SEQ ID NO: 17 to 19 Exemplary antibody Fc-region N-terminal amino acid sequences
SEQ ID NO: 20 to 38 Amino acid sequence tag
SEQ ID NO: 39 Human CH2 domain
SEQ ID NO: 40 Human CH3 domain
SEQ ID NO: 41 to 55 Exemplary wild-type and variant antibody heavy chain Fc-region polypeptides
SEQ ID NO: 56 to 58 Exemplary antibody hinge region amino acid sequences
SEQ ID NO: 59 to 74 Sequences used in the examples.
SEQ ID NO: 78 Sortase motif

EXAMPLES

The following examples are examples of methods and compositions of the invention. It is understood that various other embodiments may be practiced, given the general description provided above.

Although the foregoing invention has been described in some detail by way of illustration and example for purposes of clarity of understanding, the descriptions and examples should not be construed as limiting the scope of the invention.

Materials and Methods

Recombinant DNA Techniques

Standard methods were used to manipulate DNA as described in Sambrook, J., et al., Molecular Cloning: A Laboratory Manual; Cold Spring Harbor Laboratory Press, Cold Spring Harbor, N.Y. (1989). The molecular biological reagents were used according to the manufacturer's instructions.

Gene Synthesis

Desired gene segments were prepared by chemical synthesis at Geneart GmbH (Regensburg, Germany) The synthesized gene fragments were cloned into an *E. coli* plasmid for propagation/amplification. The DNA sequence of the subcloned gene fragments were verified by DNA sequencing.

Protein Determination

The protein concentration of purified polypeptides was determined by determining the optical density (OD) at 280 nm, using the molar extinction coefficient calculated on the basis of the amino acid sequence of the polypeptide.

Example 1

Generation of the Expression Plasmids

Description of the Basic/Standard Mammalian Expression Plasmid

Desired proteins were expressed by transient transfection of human embryonic kidney cells (HEK 293). For the expression of a desired gene/protein (e.g. full length antibody heavy chain, full length antibody light chain, or an Fc-chain containing an oligoglycine at its N-terminus) a transcription unit comprising the following functional elements was used:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence (SS),
- a gene/protein to be expressed (e.g. full length antibody heavy chain), and
- the bovine growth hormone polyadenylation sequence (BGH pA).

Beside the expression unit/cassette including the desired gene to be expressed the basic/standard mammalian expression plasmid contains
- an origin of replication from the vector pUC18 which allows replication of this plasmid in *E. coli*, and
- a beta-lactamase gene which confers ampicillin resistance in *E. coli*.

Expression plasmids coding for the following polypeptides/proteins were constructed:

Pertuzumab heavy chain variable domain combined with a human heavy chain constant region of the subclass IgG1 containing a T366W mutation:

(SEQ ID NO: 59)
EVQLVESGGGLVQPGGSLRLSCAASGFTFTDYTMDWVRQAPGKGLEW

VADVNPNSGGSIYNQRFKGRFTLSVDRSKNTLYLQMNSLRAEDTAVYY

CARNLGPSFYFDYWGQGTLVTVSSASTKGPSVFPLAPSSKSTSGGTAAL

GCLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPSV

FLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTI

SKAKGQPREPQVYTLPPCRDELTKNQVSLWCLVKGFYPSDIAVEWESN

GQPENNYKTTPPVLDSDGSFFLYSKLTVDKSRWQQGNVFSCSVMHEAL

HNHYTQKSLSLSPGK.

Pertuzumab light chain variable domain combined with a human kappa light chain constant region:

(SEQ ID NO: 60)
DIQMTQSPSSLSASVGDRVTITCKASQDVSIGVAWYQQKPGKAPKLLIY

SASYRYTGVPSRFSGSGSGTDFTLTISSLQPEDFATYYCQQYYIYPYTFG

QGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEV

THQGLSSPVTKSFNRGEC.

Trastuzumab heavy chain variable domain combined with a human heavy chain constant region of the subclass IgG1 containing a T366S, L368A, and Y407V mutation:

(SEQ ID NO: 61)
EVQLVESGGGLVQPGGSLRLSCAASGFNIKDTYIHWVRQAPGKGLEWV

ARIYPTNGYTRYADSVKGRFTISADTSKNTAYLQMNSLRAEDTAVYYC

SRWGGDGFYAMDYWGQGTLVTVSSASTKGPSVFPLAPSSKSTSGGTA

ALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGP

SVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIE

KTISKAKGQPREPQVCTLPPSRDELTKNQVSLSCAVKGFYPSDIAVEWE

SNGQPENNYKTTPPVLDSDGSFFLVSKLTVDKSRWQQGNVFSCSVMHE

ALHNHYTQKSLSLSPGK.

Trastuzumab light chain variable domain combined with a human kappa light chain constant region:

(SEQ ID NO: 62)
DIQMTQSPSSLSASVGDRVTITCRASQDVNTAVAWYQQKPGKAPKLLI

YSASFLYSGVPSRFSGSRSGTDFTLTISSLQPEDFATYYCQQHYTTPPTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACE

VTHQGLSSPVTKSFNRGEC.

antibody Fab fragment comprising a Pertuzumab heavy chain variable domain and a human heavy chain constant region 1 (CH1) of the subclass IgG1 containing a C-terminal GGGSLPETGGSGSHHHHHH (SEQ ID NO: 16) amino acid sequence:

(SEQ ID NO: 63)
EVQLVESGGGLVQPGGSLRLSCAASGFTFTDYTMDWVRQAPGKGLEW

VADVNPNSGGSIYNQRFKGRFTLSVDRSKNTLYLQMNSLRAEDTAVYY

CARNLGPSFYFDYWGQGTLVTVSSASTKGPSVFPLAPSSKSTSGGTAAL

GCLVKDYFPEPVTVSWNSGALTSGVHTFPAVLQSSGLYSLSSVVTVPSS

SLGTQTYICNVNHKPSNTKVDKKVEPKSCGGGSLPETGGSGSHHHHHH.

antibody Fab fragment comprising a Pertuzumab heavy chain variable domain and a human heavy chain constant region 1 (CH1) of the subclass IgG1 containing a C-terminal GSLPETGGSGSHHHHHH (SEQ ID NO: 15) sequence:

(SEQ ID NO: 64)
EVQLVESGGGLVQPGGSLRLSCAASGFTFTDYTMDWVRQAPGKGLEW

VADVNPNSGGSIYNQRFKGRFTLSVDRSKNTLYLQMNSLRAEDTAVYY

CARNLGPSFYFDYWGQGTLVTVSSASTKGPSVFPLAPSSKSTSGGTAAL

GCLVKDYFPEPVTVSWNSGALTSGVHTFPAVLQSSGLYSLSSVVTVPSS

SLGTQTYICNVNHKPSNTKVDKKVEPKSCGSLPETGGSGSHHHHHH.

antibody Fab fragment comprising a Pertuzumab heavy chain variable domain and a human heavy chain constant region 1 (CH1) of the subclass IgG1 containing a C-terminal LPETGGSGSHHHHHH (SEQ ID NO: 14) sequence:

(SEQ ID NO: 65)
EVQLVESGGGLVQPGGSLRLSCAASGFTFTDYTMDWVRQAPGKGLEW

VADVNPNSGGSIYNQRFKGRFTLSVDRSKNTLYLQMNSLRAEDTAVYY

CARNLGPSFYFDYWGQGTLVTVSSASTKGPSVFPLAPSSKSTSGGTAAL

GCLVKDYFPEPVTVSWNSGALTSGVHTFPAVLQSSGLYSLSSVVTVPSS

SLGTQTYICNVNHKPSNTKVDKKVEPKSCLPETGGSGSHHHHHH.

antibody Fab fragment comprising a Trastuzumab heavy chain variable domain and a human heavy chain constant region 1 (CH1) of the subclass IgG1 containing a C-terminal GGGSLPETGGSGSHHHHHH (SEQ ID NO: 16) sequence:

(SEQ ID NO: 66)
EVQLVESGGGLVQPGGSLRLSCAASGFNIKDTYIHWVRQAPGKGLEWV

ARIYPTNGYTRYADSVKGRFTISADTSKNTAYLQMNSLRAEDTAVYYC

SRWGGDGFYAMDYWGQGTLVTVSSASTKGPSVFPLAPSSKSTSGGTA

ALGCLVKDYFPEPVTVSWNSGALTSGVHTFPAVLQSSGLYSLSSVVTVP

SSSLGTQTYICNVNHKPSNTKVDKKVEPKSCGGGSLPETGGSGSHHHH

HH.

antibody Fab fragment comprising a Trastuzumab heavy chain variable domain and a human heavy chain constant region 1 (CH1) of the subclass IgG1 containing a C-terminal GSLPETGGSGSHHHHHH (SEQ ID NO: 15) sequence:

(SEQ ID NO: 67)
EVQLVESGGGLVQPGGSLRLSCAASGFNIKDTYIHWVRQAPGKGLEWV

ARIYPTNGYTRYADSVKGRFTISADTSKNTAYLQMNSLRAEDTAVYYC

SRWGGDGFYAMDYWGQGTLVTVSSASTKGPSVFPLAPSSKSTSGGTA

ALGCLVKDYFPEPVTVSWNSGALTSGVHTFPAVLQSSGLYSLSSVVTVP

SSSLGTQTYICNVNHKPSNTKVDKKVEPKSCGSLPETGGSGSHHHHHH.

antibody Fab fragment comprising a Trastuzumab heavy chain variable domain and a human heavy chain constant region 1 (CH1) of the subclass IgG1 containing a C-terminal LPETGGSGSHHHHHH (SEQ ID NO: 14) sequence:

(SEQ ID NO: 68)
EVQLVESGGGLVQPGGSLRLSCAASGFNIKDTYIHWVRQAPGKGLEWV

ARIYPTNGYTRYADSVKGRFTISADTSKNTAYLQMNSLRAEDTAVYYC

SRWGGDGFYAMDYWGQGTLVTVSSASTKGPSVFPLAPSSKSTSGGTA

ALGCLVKDYFPEPVTVSWNSGALTSGVHTFPAVLQSSGLYSLSSVVTVP

SSSLGTQTYICNVNHKPSNTKVDKKVEPKSCLPETGGSGSHHHHHH.

heavy chain Fc-region polypeptide (human IgG1(CH2-CH3)) with T366S, L368A, and Y407V mutation containing an N-terminal GGGDKTHTCPPC (SEQ ID NO: 19) sequence:

(SEQ ID NO: 69)
GGGDKTHTCPPCPAPELLGGPSVFLFPPKPKDTLMISRTPEVTCVVVDV

SHEDPEVKFNWYVDGVEVHNAKTKPREEQYNSTYRVVSVLTVLHQD

WLNGKEYKCKVSNKALPAPIEKTISKAKGQPREPQVCTLPPSRDELTKN

QVSLSCAVKGFYPSDIAVEWESNGQPENNYKTTPPVLDSDGSFFLVSKL

TVDKSRWQQGNVFSCSVMHEALHNHYTQKSLSLSPGK.

heavy chain Fc-region polypeptide (human IgG1(CH2-CH3)) with T366S, L368A, and Y407V mutation containing an N-terminal GGHTCPPC (SEQ ID NO: 18) sequence:

(SEQ ID NO: 70)
GGHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGK

EYKCKVSNKALPAPIEKTISKAKGQPREPQVCTLPPSRDELTKNQVSLSC

AVKGFYPSDIAVEWESNGQPENNYKTTPPVLDSDGSFFLVSKLTVDKSR

WQQGNVFSCSVMHEALHNHYTQKSLSLSPGK.

heavy chain Fc-region polypeptide (human IgG1(CH2-CH3)) with T366S, L368A, and Y407V mutation containing an N-terminal GGCPPC (SEQ ID NO: 17) sequence:

(SEQ ID NO: 71)
GGCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEY

KCKVSNKALPAPIEKTISKAKGQPREPQVCTLPPSRDELTKNQVSLSCA

VKGFYPSDIAVEWESNGQPENNYKTTPPVLDSDGSFFLVSKLTVDKSR

WQQGNVFSCSVMHEALHNHYTQKSLSLSPGK.

heavy chain Fc-region polypeptide (human IgG1(CH2-CH3)) with T366W mutation containing an N-terminal GGGDKTHTCPPC (SEQ ID NO: 19) sequence:

(SEQ ID NO: 72)
GGGDKTHTCPPCPAPELLGGPSVFLFPPKPKDTLMISRTPEVTCVVVDV

SHEDPEVKFNWYVDGVEVHNAKTKPREEQYNSTYRVVSVLTVLHQD

WLNGKEYKCKVSNKALPAPIEKTISKAKGQPREPQVYTLPPCRDELTK

NQVSLWCLVKGFYPSDIAVEWESNGQPENNYKTTPPVLDSDGSFFLYS

KLTVDKSRWQQGNVFSCSVMHEALHNHYTQKSLSLSPGK.

heavy chain Fc-region polypeptide (human IgG1(CH2-CH3)) with T366W mutations containing an N-terminal GGHTCPPC (SEQ ID NO: 18) sequence:

(SEQ ID NO: 73)
GGHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGK

EYKCKVSNKALPAPIEKTISKAKGQPREPQVYTLPPCRDELTKNQVSLW

CLVKGFYPSDIAVEWESNGQPENNYKTTPPVLDSDGSFFLYSKLTVDKS

RWQQGNVFSCSVMHEALHNHYTQKSLSLSPGK.

heavy chain Fc-region polypeptide (human IgG1(CH2-CH3)) with T366W mutation containing an N-terminal GGCPPC (SEQ ID NO: 17) sequence:

(SEQ ID NO: 74)
GGCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEY

KCKVSNKALPAPIEKTISKAKGQPREPQVYTLPPCRDELTKNQVSLWCL

VKGFYPSDIAVEWESNGQPENNYKTTPPVLDSDGSFFLYSKLTVDKSR

WQQGNVFSCSVMHEALHNHYTQKSLSLSPGK.

Example 2

Transient Expression, Purification and Analytical Characterization

The antibody chains were generated by transient transfection of HEK293 cells (human embryonic kidney cell line 293-derived) cultivated in F17 Medium (Invitrogen Corp.). For transfection "293-Fectin" Transfection Reagent (Invitrogen) was used. The antibody chains were expressed from three different plasmids, coding for a full length heavy chain (either Pertuzumab-knob, or Trastuzumab-hole), a corresponding full length light chain, and a heavy chain Fc-region polypeptide containing one of the N-terminal oligoglycine sequences either as knob, or as hole variant. The three plasmids were used at an equimolar plasmid ratio upon transfection. Transfections were performed as specified in the manufacturer's instructions. Antibody Fc-region-containing cell culture supernatants were harvested seven days after transfection. Supernatants were stored frozen until purification.

The antibody Fc-region-containing culture supernatants were filtered and purified by two chromatographic steps. The antibody Fc-regions were captured by affinity chromatography using HiTrap MabSelectSuRe (GE Healthcare) equilibrated with PBS (1 mM $KH_2PO_4$, 10 mM $Na_2HPO_4$, 137 mM NaCl, 2.7 mM KCl), pH 7.4. Unbound proteins were removed by washing with equilibration buffer, and the antibody Fc-region was recovered with 0.1 M citrate buffer, pH 3.0 Immediately after elution the solution was neutralized to pH 6.0 with 1 M Tris-base, pH 9.0. Size exclusion chromatography on Superdex 200™ (GE Healthcare) was used as second purification step. The size exclusion chromatography was performed in 40 mM Tris-HCl buffer, 0.15 M NaCl, pH 7.5. The eluted antibody Fc-regions were concentrated with an Ultrafree-CL centrifugal filter unit equipped with a Biomax-SK membrane (Millipore, Billerica, Mass.) and stored at −80° C.

The protein concentrations of the antibody Fc-regions were determined by measuring the optical density (OD) at 280 nm, using the molar extinction coefficient calculated on the basis of the amino acid sequence. Purity and proper antibody Fc-region formation were analyzed by SDS-PAGE in the presence and absence of a reducing agent (5 mM 1.4-dithiotreitol) and staining with Coomassie brilliant blue.

Example 3

Transient Expression, Purification and Analytical Characterization of Antibody Fab Fragments Containing the C-Terminal LPX1TG Motif The antibody Fab fragments were generated by transient transfection of HEK293 cells (human embryonic kidney cell line 293-derived) cultivated in F17 Medium (Invitrogen Corp.). For transfection "293-Fectin" Transfection Reagent (Invitrogen) was used. The antibody Fab fragments were expressed from two different plasmids, coding for a full length light chain (either Pertuzumab, or Trastuzumab) and a corresponding truncated heavy chain containing one of the C-terminal LPX1TG (SEQ ID NO: 01) sequences. The two plasmids were used at an equimolar plasmid ratio upon transfection. Transfections were performed as specified in the manufacturer's instructions. Fab fragment-containing cell culture supernatants were harvested seven days after transfection. Supernatants were stored frozen until purification.

The Fab fragment containing culture supernatants were filtered and purified by two chromatographic steps. The Fab fragments were captured by affinity chromatography using HisTrap HP Ni-NTA columns (GE Healthcare) equilibrated with PBS and 20 mM Imidazole (1 mM $KH_2PO_4$, 10 mM $Na_2HPO_4$, 137 mM NaCl, 2.7 mM KCl, 20 mM Imidazole), pH 7.4. Unbound proteins were removed by washing with equilibration buffer. The histidine-tagged protein was eluted with a 20 mM to 400 mM linear imidazole gradient in PBS (1 mM $KH_2PO_4$, 10 mM $Na_2HPO_4$, 137 mM NaCl, 2.7 mM KCl, 400 mM imidazole) in 10 column volumes. Size exclusion chromatography on Superdex 200™ (GE Healthcare) was used as second purification step. The size exclusion chromatography was performed in 40 mM Tris-HCl buffer, 0.15 M NaCl, pH 7.5. The Fab fragments were concentrated with an Ultrafree-CL centrifugal filter unit equipped with a Biomax-SK membrane (Millipore, Billerica, Mass.) and stored at −80° C.

The protein concentrations of the Fab fragments were determined by measuring the optical density (OD) at 280 nm, using the molar extinction coefficient calculated on the basis of the amino acid sequence. Purity and proper Fab formation were analyzed by SDS-PAGE in the presence and absence of a reducing agent (5 mM 1. 4-dithiotreitol) and staining with Coomassie brilliant blue.

Example 4

Sortase a Mediated Ligation of Antibody Fc-Region and Binding Entity (Fab Fragment)

For the sortase-mediated transpeptidation reaction, N-terminally truncated *Staphylococcus aureus* Sortase A was used ($\Delta_{1-59}$). The reaction was performed in a buffer containing 50 mM Tris-HCl, 150 mM NaCl, pH 7.5 (Sortase-buffer). In the reaction, a Fab fragment bearing a sortase motif (LPETG (SEQ ID NO: 78)) at its C-terminus of the VH—CH1-heavy chain including no or 2 different connecting short amino acid sequences between the C-terminal end of the VH—CH1 heavy chain (. . . KSC) and the N-terminus of the sortase motif (LPETGGSGSHHHHHH, SEQ ID NO: 14, GSLPETGGSGSHHHHHH, SEQ ID NO: 15, and GGGSLPETGGSGSHHHHHH, SEQ ID NO: 16) and a one-armed antibody bearing an oligoglycine motif and three different hinge sequences (GGCPPC, SEQ ID NO: 17, GGHTCPPC, SEQ ID NO: 18, and GGGDKTHTCPPC, SEQ ID NO: 19, respectively) at its N-terminus of the heavy chain Fc-region polypeptide were linked, resulting in the antibody Fc-region conjugate. To perform the reaction, all reagents were brought in solution in sortase buffer. In a first step, the antibody Fc-region and the antibody Fab fragment were mixed, and the reaction was started by the following addition of Sortase A and 5 mM $CaCl_2$. The components were mixed by pipetting and incubated at 37° C. for 72 h. Subsequently, the reaction was stopped by freezing of the reaction mixture and storage at −20° C. until analysis.

Molar ratio Fab:One-armed antibody:sortase=20:4:1

RESULTS

Three different sequences at the C-terminus of the Fab and at the N-terminus of the antibody respectively were conjugated by Sortase A to obtain nine different combinations of antibody Fc-region conjugates. The efficiency of the coupling reaction was evaluated at different time points. To this end aliquots of the transpeptidation reactions were analyzed by SDS-PAGE. The efficiency of ligation was estimated densitometrically from the SDS PAGE gel. Results after 72 h of reaction are depicted in Table 2 for the respective sequences.

TABLE 2

Conjugation of Fab fragments with one-armed antibodies

| Fab VH-CH1 heavy chain | One armed antibody Fc-region (OA-Fc-region) | | |
|---|---|---|---|
| | GGGDKTHTCPPC (SEQ ID NO: 19) | GGHTCPPC (SEQ ID NO: 18) | GGCPPC (SEQ ID NO: 17) |
| KSCGGGSLPETGGSGSHHHHHH (SEQ ID NO: 75) | approx. 0.54% | approx. 0.62% | approx. 0.73% |
| KSCGSLPETGGSGSHHHHHH (SEQ ID NO: 76) | approx. 0.56% | approx. 0.56% | approx. 0.73% |
| KSCLPETGGSGSHHHHHH (SEQ ID NO: 77) | approx. 0.52% | approx. 0.54% | approx. 0.54% |

What is claimed is:

1. A method for producing an antibody Fc-region conjugate, which comprises as a first component an antibody Fc-region and as a second component a Fab that specifically binds to a target, wherein the method comprises incubating:
   (i) a Fab fragment comprising the amino acid sequence KSCGSLPETGGSGSHHHHHH (SEQ ID NO: 76) within its 20 C-terminal amino acid residues, and an antibody Fc-region, comprising two heavy chain fragments each comprising an N-terminus, which comprises at one of its N-termini the amino acid sequence GGCPPC (SEQ ID NO: 17), with the enzyme Sortase A; or
   (ii) a Fab fragment comprising the amino acid sequence KSCGGGSLPETGGSGSHHHHHH (SEQ ID NO: 75), and an antibody Fc-region, comprising two heavy chain fragments each comprising an N-terminus, which comprises at one of its N-termini the amino acid sequence GGCPPC (SEQ ID NO: 17), with the enzyme Sortase A, thereby producing the antibody Fc-region conjugate.

2. The method of claim 1, further comprising, prior to incubating the antibody Fc-region and the Fab fragment:
   (a) culturing a first host cell comprising a nucleic acid encoding the antibody Fc-region component of the conjugate under conditions suitable for expression of the antibody Fc-region; and
   (b) culturing a second host cell comprising a nucleic acid encoding the Fab fragment under conditions suitable for expression of the Fab fragment.

3. The method of claim 1, wherein the Fc-region comprises, at both N-termini, the amino acid sequence GGCPPC (SEQ ID NO: 17).

* * * * *

SEQUENCE LISTING

<160> NUMBER OF SEQ ID NOS: 85

<210> SEQ ID NO 1
<211> LENGTH: 5
<212> TYPE: PRT
<213> ORGANISM: Artificial Sequence
<220> FEATURE:
<223> OTHER INFORMATION: Sortase amino acid sequence tag
<220> FEATURE:
<221> NAME/KEY: VARIANT
<222> LOCATION: 3
<223> OTHER INFORMATION: Xaa = Any Amino Acid

<400> SEQUENCE: 1

Leu Pro Xaa Thr Gly
1               5

<210> SEQ ID NO 2
<211> LENGTH: 9
<212> TYPE: PRT
<213> ORGANISM: Artificial Sequence
<220> FEATURE:
<223> OTHER INFORMATION: Sortase amino acid sequence tag 2
<220> FEATURE:
<221> NAME/KEY: VARIANT
<222> LOCATION: 1, 2, 3
<223> OTHER INFORMATION: Up to 2 can be absent
<220> FEATURE:

```
<221> NAME/KEY: VARIANT
<222> LOCATION: 7
<223> OTHER INFORMATION: Xaa = Any Amino Acid

<400> SEQUENCE: 2

Gly Gly Gly Ser Leu Pro Xaa Thr Gly
1               5

<210> SEQ ID NO 3
<211> LENGTH: 13
<212> TYPE: PRT
<213> ORGANISM: Artificial Sequence
<220> FEATURE:
<223> OTHER INFORMATION: Sortase amino acid sequence tag 3
<220> FEATURE:
<221> NAME/KEY: VARIANT
<222> LOCATION: 1, 2, 3
<223> OTHER INFORMATION: Up to 2 can be absent
<220> FEATURE:
<221> NAME/KEY: VARIANT
<222> LOCATION: 7
<223> OTHER INFORMATION: Xaa = Any Amino Acid

<400> SEQUENCE: 3

Gly Gly Gly Ser Leu Pro Xaa Thr Gly Gly Ser Gly Ser
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Sortase amino acid sequence tag 5
<220> FEATURE:
<221> NAME/KEY: VARIANT
<222> LOCATION: 1
<223> OTHER INFORMATION: Xaa = Any Amino Acid except Gly
<220> FEATURE:
<221> NAME/KEY: VARIANT
<222> LOCATION: 6
<223> OTHER INFORMATION: Xaa = Any Naturally Occurring Amino Acid

<400> SEQUENCE: 4

Xaa Gly Ser Leu Pro Xaa Thr Gly Gly Ser Gly Ser
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Sortase amino acid sequence tag 5
<220> FEATURE:
<221> NAME/KEY: VARIANT
<222> LOCATION: 1, 2, 3
<223> OTHER INFORMATION: Up to 2 can be absent
<220> FEATURE:
<221> NAME/KEY: VARIANT
<222> LOCATION: 7
<223> OTHER INFORMATION: Xaa = Any Amino Acid
<220> FEATURE:
<221> NAME/KEY: VARIANT
<222> LOCATION: 13
<223> OTHER INFORMATION: Residue followed by an amino acid sequence tag

<400> SEQUENCE: 5

Gly Gly Gly Ser Leu Pro Xaa Thr Gly Gly Ser Gly Ser
1               5                   10

<210> SEQ ID NO 6
<211> LENGTH: 12
```

```
<212> TYPE: PRT
<213> ORGANISM: Artificial Sequence
<220> FEATURE:
<223> OTHER INFORMATION: Sortase amino acid sequence tag 6
<220> FEATURE:
<221> NAME/KEY: VARIANT
<222> LOCATION: 1
<223> OTHER INFORMATION: Xaa = Any Amino Acid except Gly
<220> FEATURE:
<221> NAME/KEY: VARIANT
<222> LOCATION: 6
<223> OTHER INFORMATION: Xaa = Any Amino Acid
<220> FEATURE:
<221> NAME/KEY: VARIANT
<222> LOCATION: 12
<223> OTHER INFORMATION: Residue followed by an amino acid sequence tag

<400> SEQUENCE: 6

Xaa Gly Ser Leu Pro Xaa Thr Gly Gly Ser Gly Ser
1               5                   10

<210> SEQ ID NO 7
<211> LENGTH: 6
<212> TYPE: PRT
<213> ORGANISM: Artificial Sequence
<220> FEATURE:
<223> OTHER INFORMATION: Hinge nucleophile
<220> FEATURE:
<221> NAME/KEY: VARIANT
<222> LOCATION: 5
<223> OTHER INFORMATION: Xaa = Ser or Pro

<400> SEQUENCE: 7

Gly Gly Cys Pro Xaa Cys
1               5

<210> SEQ ID NO 8
<211> LENGTH: 8
<212> TYPE: PRT
<213> ORGANISM: Artificial Sequence
<220> FEATURE:
<223> OTHER INFORMATION: Hinge nucleophile 2
<220> FEATURE:
<221> NAME/KEY: VARIANT
<222> LOCATION: 7
<223> OTHER INFORMATION: Xaa = Ser or Pro

<400> SEQUENCE: 8

Gly Gly His Thr Cys Pro Xaa Cys
1               5

<210> SEQ ID NO 9
<211> LENGTH: 10
<212> TYPE: PRT
<213> ORGANISM: Artificial Sequence
<220> FEATURE:
<223> OTHER INFORMATION: Sortase product characteristic amino acid
      sequence
<220> FEATURE:
<221> NAME/KEY: VARIANT
<222> LOCATION: 1, 2, 3
<223> OTHER INFORMATION: Up to 2 can be absent
<220> FEATURE:
<221> NAME/KEY: VARIANT
<222> LOCATION: 7
<223> OTHER INFORMATION: Xaa = Any Amino Acid

<400> SEQUENCE: 9

Gly Gly Gly Ser Leu Pro Xaa Thr Gly Gly
1               5                   10
```

```
<210> SEQ ID NO 10
<211> LENGTH: 14
<212> TYPE: PRT
<213> ORGANISM: Artificial Sequence
<220> FEATURE:
<223> OTHER INFORMATION: Sortase product characteristic amino acid
      sequence 2
<220> FEATURE:
<221> NAME/KEY: VARIANT
<222> LOCATION: 1, 2, 3
<223> OTHER INFORMATION: Up to 2 can be absent
<220> FEATURE:
<221> NAME/KEY: VARIANT
<222> LOCATION: 7
<223> OTHER INFORMATION: Xaa = Any Amino Acid
<220> FEATURE:
<221> NAME/KEY: VARIANT
<222> LOCATION: 13
<223> OTHER INFORMATION: Xaa = Ser or Pro

<400> SEQUENCE: 10

Gly Gly Gly Ser Leu Pro Xaa Thr Gly Gly Cys Pro Xaa Cys
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Sortase product characteristic amino acid
      sequence 3
<220> FEATURE:
<221> NAME/KEY: VARIANT
<222> LOCATION: 1
<223> OTHER INFORMATION: Xaa = Any Amino Acid except Gly
<220> FEATURE:
<221> NAME/KEY: VARIANT
<222> LOCATION: 6
<223> OTHER INFORMATION: Xaa = Any Amino Acid
<220> FEATURE:
<221> NAME/KEY: VARIANT
<222> LOCATION: 12
<223> OTHER INFORMATION: Xaa = Ser or Pro

<400> SEQUENCE: 11

Xaa Gly Ser Leu Pro Xaa Thr Gly Gly Cys Pro Xaa Cys
1               5                   10

<210> SEQ ID NO 12
<211> LENGTH: 16
<212> TYPE: PRT
<213> ORGANISM: Artificial Sequence
<220> FEATURE:
<223> OTHER INFORMATION: Sortase product characteristic amino acid
      sequence 4
<220> FEATURE:
<221> NAME/KEY: VARIANT
<222> LOCATION: 1, 2, 3
<223> OTHER INFORMATION: Up to 2 can be absent
<220> FEATURE:
<221> NAME/KEY: VARIANT
<222> LOCATION: 7
<223> OTHER INFORMATION: Xaa = Any Amino Acid
<220> FEATURE:
<221> NAME/KEY: VARIANT
<222> LOCATION: 15
<223> OTHER INFORMATION: Xaa = Ser or Pro

<400> SEQUENCE: 12

Gly Gly Gly Ser Leu Pro Xaa Thr Gly Gly His Thr Cys Pro Xaa Cys
1               5                   10                  15

<210> SEQ ID NO 13
```

```
<211> LENGTH: 15
<212> TYPE: PRT
<213> ORGANISM: Artificial Sequence
<220> FEATURE:
<223> OTHER INFORMATION: Sortase product characteristic amino acid
      sequence 5
<220> FEATURE:
<221> NAME/KEY: VARIANT
<222> LOCATION: 1
<223> OTHER INFORMATION: Xaa = Any Amino Acid except Gly
<220> FEATURE:
<221> NAME/KEY: VARIANT
<222> LOCATION: 6
<223> OTHER INFORMATION: Xaa = Any Amino Acid
<220> FEATURE:
<221> NAME/KEY: VARIANT
<222> LOCATION: 14
<223> OTHER INFORMATION: Xaa = Ser or Pro

<400> SEQUENCE: 13

Xaa Gly Ser Leu Pro Xaa Thr Gly Gly His Thr Cys Pro Xaa Cys
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Sortase tag example

<400> SEQUENCE: 14

Leu Pro Glu Thr Gly Gly Ser Gly Ser His His His His His His
1               5                   10                  15

<210> SEQ ID NO 15
<211> LENGTH: 17
<212> TYPE: PRT
<213> ORGANISM: Artificial Sequence
<220> FEATURE:
<223> OTHER INFORMATION: Sortase tag example 2

<400> SEQUENCE: 15

Gly Ser Leu Pro Glu Thr Gly Gly Ser Gly Ser His His His His
1               5                   10                  15

His

<210> SEQ ID NO 16
<211> LENGTH: 19
<212> TYPE: PRT
<213> ORGANISM: Artificial Sequence
<220> FEATURE:
<223> OTHER INFORMATION: Sortase tag example 3

<400> SEQUENCE: 16

Gly Gly Gly Ser Leu Pro Glu Thr Gly Gly Ser Gly Ser His His His
1               5                   10                  15

His His His

<210> SEQ ID NO 17
<211> LENGTH: 6
<212> TYPE: PRT
<213> ORGANISM: Artificial Sequence
<220> FEATURE:
<223> OTHER INFORMATION: Hinge nucleophile example

<400> SEQUENCE: 17

Gly Gly Cys Pro Pro Cys
1               5
```

```
<210> SEQ ID NO 18
<211> LENGTH: 8
<212> TYPE: PRT
<213> ORGANISM: Artificial Sequence
<220> FEATURE:
<223> OTHER INFORMATION: Hinge nucleophile example 2

<400> SEQUENCE: 18

Gly Gly His Thr Cys Pro Pro Cys
1               5

<210> SEQ ID NO 19
<211> LENGTH: 12
<212> TYPE: PRT
<213> ORGANISM: Artificial Sequence
<220> FEATURE:
<223> OTHER INFORMATION: Hinge nucleophile example 3

<400> SEQUENCE: 19

Gly Gly Gly Asp Lys Thr His Thr Cys Pro Pro Cys
1               5                   10

<210> SEQ ID NO 20
<211> LENGTH: 5
<212> TYPE: PRT
<213> ORGANISM: Artificial Sequence
<220> FEATURE:
<223> OTHER INFORMATION: Arg-tag

<400> SEQUENCE: 20

Arg Arg Arg Arg Arg
1               5

<210> SEQ ID NO 21
<211> LENGTH: 6
<212> TYPE: PRT
<213> ORGANISM: Artificial Sequence
<220> FEATURE:
<223> OTHER INFORMATION: Arg-tag

<400> SEQUENCE: 21

Arg Arg Arg Arg Arg Arg
1               5

<210> SEQ ID NO 22
<211> LENGTH: 6
<212> TYPE: PRT
<213> ORGANISM: Artificial Sequence
<220> FEATURE:
<223> OTHER INFORMATION: His-tag

<400> SEQUENCE: 22

His His His His His His
1               5

<210> SEQ ID NO 23
<211> LENGTH: 19
<212> TYPE: PRT
<213> ORGANISM: Artificial Sequence
<220> FEATURE:
<223> OTHER INFORMATION: Amino acid tag

<400> SEQUENCE: 23

Lys Asp His Leu Ile His Asn Val His Lys Glu Phe His Ala His Ala
1               5                   10                  15
```

His Asn Lys

<210> SEQ ID NO 24
<211> LENGTH: 8
<212> TYPE: PRT
<213> ORGANISM: Artificial Sequence
<220> FEATURE:
<223> OTHER INFORMATION: Amino acid tag

<400> SEQUENCE: 24

Asp Tyr Lys Asp Asp Asp Asp Lys
1               5

<210> SEQ ID NO 25
<211> LENGTH: 22
<212> TYPE: PRT
<213> ORGANISM: Artificial Sequence
<220> FEATURE:
<223> OTHER INFORMATION: Amino acid tag

<400> SEQUENCE: 25

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 26
<211> LENGTH: 9
<212> TYPE: PRT
<213> ORGANISM: Artificial Sequence
<220> FEATURE:
<223> OTHER INFORMATION: Amino acid tag

<400> SEQUENCE: 26

Ala Trp Arg His Pro Gln Phe Gly Gly
1               5

<210> SEQ ID NO 27
<211> LENGTH: 8
<212> TYPE: PRT
<213> ORGANISM: Artificial Sequence
<220> FEATURE:
<223> OTHER INFORMATION: Amino acid tag

<400> SEQUENCE: 27

Trp Ser His Pro Gln Phe Glu Lys
1               5

<210> SEQ ID NO 28
<211> LENGTH: 10
<212> TYPE: PRT
<213> ORGANISM: Artificial Sequence
<220> FEATURE:
<223> OTHER INFORMATION: Amino acid tag

<400> SEQUENCE: 28

Met Asp Val Glu Ala Trp Leu Gly Ala Arg
1               5                   10

<210> SEQ ID NO 29
<211> LENGTH: 16
<212> TYPE: PRT
<213> ORGANISM: Artificial Sequence
<220> FEATURE:
<223> OTHER INFORMATION: Amino acid tag

<400> SEQUENCE: 29

```
Met Asp Val Glu Ala Trp Leu Gly Ala Arg Val Pro Leu Val Glu Thr
1               5                   10                  15
```

```
<210> SEQ ID NO 30
<211> LENGTH: 38
<212> TYPE: PRT
<213> ORGANISM: Artificial Sequence
<220> FEATURE:
<223> OTHER INFORMATION: Amino acid tag

<400> SEQUENCE: 30
```

```
Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35
```

```
<210> SEQ ID NO 31
<211> LENGTH: 10
<212> TYPE: PRT
<213> ORGANISM: Artificial Sequence
<220> FEATURE:
<223> OTHER INFORMATION: Amino acid tag

<400> SEQUENCE: 31
```

```
Glu Gln Lys Leu Ile Ser Glu Glu Asp Leu
1               5                   10
```

```
<210> SEQ ID NO 32
<211> LENGTH: 15
<212> TYPE: PRT
<213> ORGANISM: Artificial Sequence
<220> FEATURE:
<223> OTHER INFORMATION: Amino acid tag

<400> SEQUENCE: 32
```

```
Lys Glu Thr Ala Ala Ala Lys Phe Glu Arg Gln His Met Asp Ser
1               5                   10                  15
```

```
<210> SEQ ID NO 33
<211> LENGTH: 26
<212> TYPE: PRT
<213> ORGANISM: Artificial Sequence
<220> FEATURE:
<223> OTHER INFORMATION: Amino acid tag

<400> SEQUENCE: 33
```

```
Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25
```

```
<210> SEQ ID NO 34
<211> LENGTH: 47
<212> TYPE: PRT
<213> ORGANISM: Artificial Sequence
<220> FEATURE:
<223> OTHER INFORMATION: Amino acid tag

<400> SEQUENCE: 34
```

```
Pro Ala Thr Thr Thr Gly Ser Ser Pro Gly Pro Thr Gln Ser His Tyr
1               5                   10                  15

Gly Gln Cys Gly Gly Ile Gly Tyr Ser Gly Pro Thr Val Cys Ala Ser
```

-continued

```
                    20                  25                  30
Gly Thr Thr Cys Gln Val Leu Asn Pro Tyr Tyr Ser Gln Cys Leu
        35                  40                  45

<210> SEQ ID NO 35
<211> LENGTH: 32
<212> TYPE: PRT
<213> ORGANISM: Butyrivibrio fibrisolvens

<400> SEQUENCE: 35

Met Asp Trp Asn Ala Asn Ile Ala Pro Gly Asn Ser Val Glu Phe Gly
1               5                   10                  15

Ile Gln Gly Ala Gly Ser Val Gly Asn Val Ile Asp Ile Thr Val Glu
            20                  25                  30

<210> SEQ ID NO 36
<211> LENGTH: 51
<212> TYPE: PRT
<213> ORGANISM: Artificial Sequence
<220> FEATURE:
<223> OTHER INFORMATION: Chitin-binding-domain

<400> SEQUENCE: 36

Thr Asn Pro Gly Val Ser Ala Trp Gln Val Asn Thr Ala Tyr Thr Ala
1               5                   10                  15

Gly Gln Leu Val Thr Tyr Asn Gly Lys Thr Tyr Lys Cys Leu Gln Pro
            20                  25                  30

His Thr Ser Leu Ala Gly Trp Glu Pro Ser Asn Val Pro Ala Leu Trp
        35                  40                  45

Gln Leu Gln
        50

<210> SEQ ID NO 37
<211> LENGTH: 209
<212> TYPE: PRT
<213> ORGANISM: Chondrus crispus

<400> SEQUENCE: 37

Met Pro Glu Ile Lys Leu Thr Tyr Phe Asp Met Arg Gly Arg Ala Glu
1               5                   10                  15

Ala Ser Arg Leu Ala Leu Val Val Gly Glu Ile Pro Phe Glu Asp Glu
            20                  25                  30

Arg Val Val Phe Asp His Trp Lys Glu Ala Lys Pro Lys Thr Pro Tyr
        35                  40                  45

Ala Ala Leu Pro Met Leu Thr Val Asp Gly Met Gln Val Ala Gln Ser
    50                  55                  60

Asp Ala Ile Leu Arg Tyr Cys Gly Lys Leu Ala Gly Leu Tyr Pro Ser
65                  70                  75                  80

Asp Pro Leu Glu Ala Ala Lys Val Asp Glu Val Gly Gly Val Ile Asp
                85                  90                  95

Asp Val Thr His Ala Met Tyr Arg Tyr Arg Gly Asp Asp Lys Asp Lys
            100                 105                 110

Leu Arg Glu Glu Arg Asp Lys Phe Ser Lys Val Asp Val Pro Arg Tyr
        115                 120                 125

Val Gly Ala Leu Glu Lys Arg Leu Glu Ala Phe Gly Asp Gly Pro Trp
    130                 135                 140

Ala Val Gly Gly Asn Met Thr Ile Ala Asp Leu His Ile Cys His Leu
145                 150                 155                 160
```

```
Val Thr Asn Ile Arg Cys Gly Met Leu Asp Phe Val Asp Lys Asp Leu
            165                 170                 175

Leu Glu Gly Tyr Val Arg Ile Val Lys Ser Tyr Ser Ala Val Met Glu
        180                 185                 190

His Pro Lys Val Thr Glu Trp Tyr Glu Lys Lys Pro Val Lys Met Phe
        195                 200                 205

Ser

<210> SEQ ID NO 38
<211> LENGTH: 396
<212> TYPE: PRT
<213> ORGANISM: Escherichia coli

<400> SEQUENCE: 38

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320
```

Lys Asp Lys Pro Leu Gly Ala Val Ala Leu Lys Ser Tyr Glu Glu Glu
            325                 330                 335

Leu Ala Lys Asp Pro Arg Ile Ala Ala Thr Met Glu Asn Ala Gln Lys
        340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
        370                 375                 380

Glu Ala Leu Lys Asp Ala Gln Thr Arg Ile Thr Lys
385                 390                 395

<210> SEQ ID NO 39
<211> LENGTH: 107
<212> TYPE: PRT
<213> ORGANISM: Homo sapiens

<400> SEQUENCE: 39

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Trp Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Glu Ser Thr Tyr Arg Trp Ser Val Leu Thr Val Leu His Gln Asp Trp
65                  70                  75                  80

Leu Asn Gly Lys Glu Tyr Lys Cys Lys Val Ser Asn Lys Ala Leu Pro
                85                  90                  95

Ala Pro Ile Glu Lys Thr Ile Ser Lys Ala Lys
            100                 105

<210> SEQ ID NO 40
<211> LENGTH: 106
<212> TYPE: PRT
<213> ORGANISM: Homo sapiens

<400> SEQUENCE: 40

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 41
<211> LENGTH: 222
<212> TYPE: PRT
<213> ORGANISM: Homo sapiens

<400> SEQUENCE: 41

```
Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220
```

<210> SEQ ID NO 42
<211> LENGTH: 222
<212> TYPE: PRT
<213> ORGANISM: Artificial Sequence
<220> FEATURE:
<223> OTHER INFORMATION: Variant human Fc-region of the IgG1 isotype
      with the mutations L234A, L235A

<400> SEQUENCE: 42

```
Cys Pro Pro Cys Pro Ala Pro Glu Ala Ala Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125
```

```
Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 43
<211> LENGTH: 222
<212> TYPE: PRT
<213> ORGANISM: Artificial Sequence
<220> FEATURE:
<223> OTHER INFORMATION: Variant human Fc-region of the IgG1 isotype
      with a T366S, 368A, and Y407V mutation

<400> SEQUENCE: 43

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Cys Thr Leu Pro Pro
        115                 120                 125

Ser Arg Asp Glu Leu Thr Lys Asn Gln Val Ser Leu Ser Cys Ala Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Val Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 44
<211> LENGTH: 222
<212> TYPE: PRT
<213> ORGANISM: Artificial Sequence
<220> FEATURE:
<223> OTHER INFORMATION: Variant human Fc-region of the IgG1 isotype
      with a knob mutation
```

<400> SEQUENCE: 44

```
Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Cys Arg Asp Glu Leu Thr Lys Asn Gln Val Ser Leu Trp Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220
```

<210> SEQ ID NO 45
<211> LENGTH: 222
<212> TYPE: PRT
<213> ORGANISM: Artificial Sequence
<220> FEATURE:
<223> OTHER INFORMATION: Variant human Fc-region of the IgG1 isotype
      with a L234A, L235A and hole mutation

<400> SEQUENCE: 45

```
Cys Pro Pro Cys Pro Ala Pro Glu Ala Ala Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Cys Thr Leu Pro Pro
        115                 120                 125
```

```
Ser Arg Asp Glu Leu Thr Lys Asn Gln Val Ser Leu Ser Cys Ala Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
            165                 170                 175

Gly Ser Phe Phe Leu Val Ser Lys Leu Thr Val Asp Lys Ser Arg Trp
        180                 185                 190

Gln Gln Gly Asn Val Phe Ser Cys Ser Val Met His Glu Ala Leu His
    195                 200                 205

Asn His Tyr Thr Gln Lys Ser Leu Ser Leu Ser Pro Gly Lys
    210                 215                 220

<210> SEQ ID NO 46
<211> LENGTH: 222
<212> TYPE: PRT
<213> ORGANISM: Artificial Sequence
<220> FEATURE:
<223> OTHER INFORMATION: Variant human Fc-region of the IgG1 isotype
      with a L234A, L235A and knob mutation

<400> SEQUENCE: 46

Cys Pro Pro Cys Pro Ala Pro Glu Ala Ala Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Cys Arg Asp Glu Leu Thr Lys Asn Gln Val Ser Leu Trp Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
            165                 170                 175

Gly Ser Phe Phe Leu Tyr Ser Lys Leu Thr Val Asp Lys Ser Arg Trp
        180                 185                 190

Gln Gln Gly Asn Val Phe Ser Cys Ser Val Met His Glu Ala Leu His
    195                 200                 205

Asn His Tyr Thr Gln Lys Ser Leu Ser Leu Ser Pro Gly Lys
    210                 215                 220

<210> SEQ ID NO 47
<211> LENGTH: 222
<212> TYPE: PRT
<213> ORGANISM: Artificial Sequence
<220> FEATURE:
<223> OTHER INFORMATION: Variant human Fc-region of the IgG1 isotype
``` with a P329G mutation

<400> SEQUENCE: 47

```
Cys Pro Pro Cys Pro Ala Pro Glu Leu Leu Gly Gly Pro Ser Val Phe
1               5                   10                  15
Leu Phe Pro Pro Lys Pro Lys Asp Thr Leu Met Ile Ser Arg Thr Pro
            20                  25                  30
Glu Val Thr Cys Val Val Val Asp Val Ser His Glu Asp Pro Glu Val
        35                  40                  45
Lys Phe Asn Trp Tyr Val Asp Gly Val Glu Val His Asn Ala Lys Thr
    50                  55                  60
Lys Pro Arg Glu Glu Gln Tyr Asn Ser Thr Tyr Arg Val Val Ser Val
65                  70                  75                  80
Leu Thr Val Leu His Gln Asp Trp Leu Asn Gly Lys Glu Tyr Lys Cys
                85                  90                  95
Lys Val Ser Asn Lys Ala Leu Gly Ala Pro Ile Glu Lys Thr Ile Ser
            100                 105                 110
Lys Ala Lys Gly Gln Pro Arg Glu Pro Gln Val Tyr Thr Leu Pro Pro
        115                 120                 125
Ser Arg Asp Glu Leu Thr Lys Asn Gln Val Ser Leu Thr Cys Leu Val
    130                 135                 140
Lys Gly Phe Tyr Pro Ser Asp Ile Ala Val Glu Trp Glu Ser Asn Gly
145                 150                 155                 160
Gln Pro Glu Asn Asn Tyr Lys Thr Thr Pro Pro Val Leu Asp Ser Asp
                165                 170                 175
Gly Ser Phe Phe Leu Tyr Ser Lys Leu Thr Val Asp Lys Ser Arg Trp
            180                 185                 190
Gln Gln Gly Asn Val Phe Ser Cys Ser Val Met His Glu Ala Leu His
        195                 200                 205
Asn His Tyr Thr Gln Lys Ser Leu Ser Leu Ser Pro Gly Lys
    210                 215                 220
```

<210> SEQ ID NO 48
<211> LENGTH: 222
<212> TYPE: PRT
<213> ORGANISM: Artificial Sequence
<220> FEATURE:
<223> OTHER INFORMATION: Variant human Fc-region of the IgG1 isotype
      with a L234A, L235A and P329G mutation

<400> SEQUENCE: 48

```
Cys Pro Pro Cys Pro Ala Pro Glu Ala Ala Gly Gly Pro Ser Val Phe
1               5                   10                  15
Leu Phe Pro Pro Lys Pro Lys Asp Thr Leu Met Ile Ser Arg Thr Pro
            20                  25                  30
Glu Val Thr Cys Val Val Val Asp Val Ser His Glu Asp Pro Glu Val
        35                  40                  45
Lys Phe Asn Trp Tyr Val Asp Gly Val Glu Val His Asn Ala Lys Thr
    50                  55                  60
Lys Pro Arg Glu Glu Gln Tyr Asn Ser Thr Tyr Arg Val Val Ser Val
65                  70                  75                  80
Leu Thr Val Leu His Gln Asp Trp Leu Asn Gly Lys Glu Tyr Lys Cys
                85                  90                  95
Lys Val Ser Asn Lys Ala Leu Gly Ala Pro Ile Glu Lys Thr Ile Ser
            100                 105                 110
Lys Ala Lys Gly Gln Pro Arg Glu Pro Gln Val Tyr Thr Leu Pro Pro
```

```
            115                 120                 125
Ser Arg Asp Glu Leu Thr Lys Asn Gln Val Ser Leu Thr Cys Leu Val
130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
            195                 200                 205

Asn His Tyr Thr Gln Lys Ser Leu Ser Leu Ser Pro Gly Lys
            210                 215                 220
```

<210> SEQ ID NO 49
<211> LENGTH: 222
<212> TYPE: PRT
<213> ORGANISM: Artificial Sequence
<220> FEATURE:
<223> OTHER INFORMATION: Variant human Fc-region of the IgG1 isotype
      with a P239G and hole mutation

<400> SEQUENCE: 49

```
Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
            35                  40                  45

Lys Phe Asn Trp Tyr Val Asp Gly Val Glu Val His Asn Ala Lys Thr
        50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Gly Ala Pro Ile Glu Lys Thr Ile Ser
            100                 105                 110

Lys Ala Lys Gly Gln Pro Arg Glu Pro Gln Val Cys Thr Leu Pro Pro
        115                 120                 125

Ser Arg Asp Glu Leu Thr Lys Asn Gln Val Ser Leu Ser Cys Ala Val
130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Val Ser Lys Leu Thr Val Asp Lys Ser Arg Trp
            180                 185                 190

Gln Gln Gly Asn Val Phe Ser Cys Ser Val Met His Glu Ala Leu His
            195                 200                 205

Asn His Tyr Thr Gln Lys Ser Leu Ser Leu Ser Pro Gly Lys
            210                 215                 220
```

<210> SEQ ID NO 50
<211> LENGTH: 222
<212> TYPE: PRT
<213> ORGANISM: Artificial Sequence
<220> FEATURE:

<223> OTHER INFORMATION: Variant human Fc-region of the IgG1 isotype
with a P329G and knob mutation

<400> SEQUENCE: 50

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Gly Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Cys Arg Asp Glu Leu Thr Lys Asn Gln Val Ser Leu Trp Cys Leu Val
130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 51
<211> LENGTH: 222
<212> TYPE: PRT
<213> ORGANISM: Artificial Sequence
<220> FEATURE:
<223> OTHER INFORMATION: Variant human Fc-region of the IgG1 isotype
with a L234A, L235A, P329G and hole mutation

<400> SEQUENCE: 51

Cys Pro Pro Cys Pro Ala Pro Glu Ala Ala Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Gly Ala Pro Ile Glu Lys Thr Ile Ser
            100                 105                 110

```
Lys Ala Lys Gly Gln Pro Arg Glu Pro Gln Val Cys Thr Leu Pro Pro
            115                 120                 125

Ser Arg Asp Glu Leu Thr Lys Asn Gln Val Ser Leu Ser Cys Ala Val
130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Val Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 52
<211> LENGTH: 222
<212> TYPE: PRT
<213> ORGANISM: Artificial Sequence
<220> FEATURE:
<223> OTHER INFORMATION: Variant human Fc-region of the IgG1 isotype
      with a L234A, L235A, P329G and knob mutation

<400> SEQUENCE: 52

Cys Pro Pro Cys Pro Ala Pro Glu Ala Ala Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Gly Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Cys Arg Asp Glu Leu Thr Lys Asn Gln Val Ser Leu Trp Cys Leu Val
130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 53
<211> LENGTH: 222
<212> TYPE: PRT
<213> ORGANISM: Homo sapiens
```

<400> SEQUENCE: 53

```
Cys Pro Ser Cys Pro Ala Pro Glu Phe Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser Gln Glu Asp Pro Glu Val
        35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Gly Leu Pro Ser Ser Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Gln Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
            180                 185                 190

Gln Glu Gly Asn Val Phe Ser Cys Ser Val Met His Glu Ala Leu His
        195                 200                 205

Asn His Tyr Thr Gln Lys Ser Leu Ser Leu Ser Leu Gly Lys
    210                 215                 220
```

<210> SEQ ID NO 54
<211> LENGTH: 222
<212> TYPE: PRT
<213> ORGANISM: Artificial Sequence
<220> FEATURE:
<223> OTHER INFORMATION: Variant human Fc-region of the IgG4 isotype with a S228P and L235E mutation

<400> SEQUENCE: 54

```
Cys Pro Pro Cys Pro Ala Pro Glu Phe Glu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser Gln Glu Asp Pro Glu Val
        35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Gly Leu Pro Ser Ser Ile Glu Lys Thr Ile Ser
            100                 105                 110

Lys Ala Lys Gly Gln Pro Arg Glu Pro Gln Val Tyr Thr Leu Pro Pro
        115                 120                 125
```

```
Ser Gln Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
            180                 185                 190

Gln Glu Gly Asn Val Phe Ser Cys Ser Val Met His Glu Ala Leu His
        195                 200                 205

Asn His Tyr Thr Gln Lys Ser Leu Ser Leu Ser Leu Gly Lys
    210                 215                 220

<210> SEQ ID NO 55
<211> LENGTH: 222
<212> TYPE: PRT
<213> ORGANISM: Artificial Sequence
<220> FEATURE:
<223> OTHER INFORMATION: Variant human Fc-region of the IgG4 isotype
      with a S228P, L235E and P329G mutation

<400> SEQUENCE: 55

Cys Pro Pro Cys Pro Ala Pro Glu Phe Glu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser Gln Glu Asp Pro Glu Val
        35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Gly Leu Gly Ser Ser Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Gln Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
            180                 185                 190

Gln Glu Gly Asn Val Phe Ser Cys Ser Val Met His Glu Ala Leu His
        195                 200                 205

Asn His Tyr Thr Gln Lys Ser Leu Ser Leu Ser Leu Gly Lys
    210                 215                 220

<210> SEQ ID NO 56
<211> LENGTH: 10
<212> TYPE: PRT
<213> ORGANISM: Homo sapiens
<220> FEATURE:
<221> NAME/KEY: VARIANT
```

<222> LOCATION: 8
<223> OTHER INFORMATION: Xaa = Ser or Pro

<400> SEQUENCE: 56

Asp Lys Thr His Thr Cys Pro Xaa Cys Pro
1               5                   10

<210> SEQ ID NO 57
<211> LENGTH: 7
<212> TYPE: PRT
<213> ORGANISM: Homo sapiens
<220> FEATURE:
<221> NAME/KEY: VARIANT
<222> LOCATION: 5
<223> OTHER INFORMATION: Xaa = Ser or Pro

<400> SEQUENCE: 57

His Thr Cys Pro Xaa Cys Pro
1               5

<210> SEQ ID NO 58
<211> LENGTH: 5
<212> TYPE: PRT
<213> ORGANISM: Homo sapiens
<220> FEATURE:
<221> NAME/KEY: VARIANT
<222> LOCATION: 3
<223> OTHER INFORMATION: Xaa = Ser or Pro

<400> SEQUENCE: 58

Cys Pro Xaa Cys Pro
1               5

<210> SEQ ID NO 59
<211> LENGTH: 449
<212> TYPE: PRT
<213> ORGANISM: Artificial Sequence
<220> FEATURE:
<223> OTHER INFORMATION: Pertuzumab heavy chain variable domain combined
      with a human heavy chain constant region of the subclass IgG1
      containing a T366W mutation

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Cys Arg Asp Glu Leu Thr Lys Asn Gln Val Ser Leu Trp
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 60
<211> LENGTH: 214
<212> TYPE: PRT
<213> ORGANISM: Artificial Sequence
<220> FEATURE:
<223> OTHER INFORMATION: Pertuzumab light chain variable domain combined
      with a human kappa light chain constant region

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
        50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ile Tyr Pro Tyr
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 61
<211> LENGTH: 450
<212> TYPE: PRT
<213> ORGANISM: Artificial Sequence
<220> FEATURE:
<223> OTHER INFORMATION: Trastuzumab heavy chain variable domain
      combined with a human heavy chain constant region of the subclass
      IgG1 containing a T366S, L368A, and Y407V mutation

<400> SEQUENCE: 61

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 62
<211> LENGTH: 214
<212> TYPE: PRT
<213> ORGANISM: Artificial Sequence
<220> FEATURE:
<223> OTHER INFORMATION: Trastuzumab light chain variable domain
      combined with a human kappa light chain constant region

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95
```

```
Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 63
<211> LENGTH: 241
<212> TYPE: PRT
<213> ORGANISM: Artificial Sequence
<220> FEATURE:
<223> OTHER INFORMATION: Antibody Fab fragment comprising a Pertuzumab
      heavy chain variable domain and a human heavy chain constant
      region 1 (CH1) of the subclass IgG1 containing a C-terminal
      GGGSLPETGGSGSHHHHHH amino acid sequence

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
            35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Gly Gly
            210                 215                 220
```

Gly Ser Leu Pro Glu Thr Gly Gly Ser Gly Ser His His His His
225                 230                 235                 240

His

<210> SEQ ID NO 64
<211> LENGTH: 239
<212> TYPE: PRT
<213> ORGANISM: Artificial Sequence
<220> FEATURE:
<223> OTHER INFORMATION: Antibody Fab fragment comprising a Pertuzumab
      heavy chain variable domain and a human heavy chain constant
      region 1 (CH1) of the subclass IgG1 containing a C-terminal
      GSLPETGGSGSHHHHHH sequence

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Ser
    210                 215                 220

Leu Pro Glu Thr Gly Gly Ser Gly Ser His His His His His
225                 230                 235

<210> SEQ ID NO 65
<211> LENGTH: 237
<212> TYPE: PRT
<213> ORGANISM: Artificial Sequence
<220> FEATURE:
<223> OTHER INFORMATION: Antibody Fab fragment comprising a Pertuzumab
      heavy chain variable domain and a human heavy chain constant
      region 1 (CH1) of the subclass IgG1 containing a C-terminal
      LPETGGSGSHHHHHH sequence

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
 50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Leu Pro
 210                 215                 220

Glu Thr Gly Gly Ser Gly Ser His His His His His His
225                 230                 235

<210> SEQ ID NO 66
<211> LENGTH: 242
<212> TYPE: PRT
<213> ORGANISM: Artificial Sequence
<220> FEATURE:
<223> OTHER INFORMATION: Antibody Fab fragment comprising a Trastuzumab
      heavy chain variable domain and a human heavy chain constant
      region 1 (CH1) of the subclass IgG1 containing a C-terminal
      GGGSLPETGGSGSHHHHHH sequence

<400> SEQUENCE: 66

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Gly
210                 215                 220

Gly Gly Ser Leu Pro Glu Thr Gly Gly Ser Gly Ser His His His His
225                 230                 235                 240

His His

<210> SEQ ID NO 67
<211> LENGTH: 240
<212> TYPE: PRT
<213> ORGANISM: Artificial Sequence
<220> FEATURE:
<223> OTHER INFORMATION: Antibody Fab fragment comprising a Trastuzumab
      heavy chain variable domain and a human heavy chain constant
      region 1 (CH1) of the subclass IgG1 containing a C-terminal
      GSLPETGGSGSHHHHHH sequence

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Gly
210                 215                 220

Ser Leu Pro Glu Thr Gly Gly Ser Gly Ser His His His His His
225                 230                 235                 240

<210> SEQ ID NO 68
<211> LENGTH: 238
<212> TYPE: PRT
<213> ORGANISM: Artificial Sequence
<220> FEATURE:
<223> OTHER INFORMATION: Antibody Fab fragment comprising a Trastuzumab
      heavy chain variable domain and a human heavy chain constant
      region 1 (CH1) of the subclass IgG1 containing a C-terminal
      LPETGGSGSHHHHHH sequence

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Leu
    210                 215                 220

Pro Glu Thr Gly Gly Ser Gly Ser His His His His His His
225                 230                 235

<210> SEQ ID NO 69
<211> LENGTH: 230
<212> TYPE: PRT
<213> ORGANISM: Artificial Sequence
<220> FEATURE:
<223> OTHER INFORMATION: Heavy chain Fc-region polypeptide (human
      IgG1(CH2-CH3)) with T366S, 368A, and Y407V mutation containing a
      N-terminal gggdkthtcppc sequence

<400> SEQUENCE: 69

Gly Gly Gly Asp Lys Thr His Thr Cys Pro Pro Cys Pro Ala Pro Glu
1               5                   10                  15

Leu Leu Gly Gly Pro Ser Val Phe Leu Phe Pro Pro Lys Pro Lys Asp
            20                  25                  30

-continued

Thr Leu Met Ile Ser Arg Thr Pro Glu Val Thr Cys Val Val Asp
            35                  40                  45

Val Ser His Glu Asp Pro Glu Val Lys Phe Asn Trp Tyr Val Asp Gly
 50                  55                  60

Val Glu Val His Asn Ala Lys Thr Lys Pro Arg Glu Glu Gln Tyr Asn
 65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Cys Thr Leu Pro Pro Ser Arg Asp Glu Leu Thr Lys Asn
    130                 135                 140

Gln Val Ser Leu Ser Cys Ala Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Val Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
    210                 215                 220

Ser Leu Ser Pro Gly Lys
225                 230

<210> SEQ ID NO 70
<211> LENGTH: 226
<212> TYPE: PRT
<213> ORGANISM: Artificial Sequence
<220> FEATURE:
<223> OTHER INFORMATION: Heavy chain Fc-region polypeptide (human
      IgG1(CH2-CH3)) with T366S, 368A, and Y407V mutation containing a
      N-terminal gghtcppc sequence

<400> SEQUENCE: 70

Gly Gly His Thr Cys Pro Pro Cys Pro Ala Pro Glu Leu Leu Gly Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Cys
        115                 120                 125

Thr Leu Pro Pro Ser Arg Asp Glu Leu Thr Lys Asn Gln Val Ser Leu
    130                 135                 140

Ser Cys Ala Val Lys Gly Phe Tyr Pro Ser Asp Ile Ala Val Glu Trp

```
                145                 150                 155                 160
Glu Ser Asn Gly Gln Pro Glu Asn Asn Tyr Lys Thr Thr Pro Pro Val
                    165                 170                 175
Leu Asp Ser Asp Gly Ser Phe Phe Leu Val Ser Lys Leu Thr Val Asp
                180                 185                 190
Lys Ser Arg Trp Gln Gln Gly Asn Val Phe Ser Cys Ser Val Met His
                195                 200                 205
Glu Ala Leu His Asn His Tyr Thr Gln Lys Ser Leu Ser Leu Ser Pro
210                 215                 220
Gly Lys
225

<210> SEQ ID NO 71
<211> LENGTH: 224
<212> TYPE: PRT
<213> ORGANISM: Artificial Sequence
<220> FEATURE:
<223> OTHER INFORMATION: Heavy chain Fc-region polypeptide (human
      IgG1(CH2-CH3)) with T366S, 368A, and Y407V mutation containing a
      N-terminal ggcppc sequence

<400> SEQUENCE: 71

Gly Gly Cys Pro Pro Cys Pro Ala Pro Glu Leu Leu Gly Gly Pro Ser
1               5                   10                  15
Val Phe Leu Phe Pro Pro Lys Pro Lys Asp Thr Leu Met Ile Ser Arg
                20                  25                  30
Thr Pro Glu Val Thr Cys Val Val Val Asp Val Ser His Glu Asp Pro
            35                  40                  45
Glu Val Lys Phe Asn Trp Tyr Val Asp Gly Val Glu Val His Asn Ala
        50                  55                  60
Lys Thr Lys Pro Arg Glu Glu Gln Tyr Asn Ser Thr Tyr Arg Val Val
65                  70                  75                  80
Ser Val Leu Thr Val Leu His Gln Asp Trp Leu Asn Gly Lys Glu Tyr
                85                  90                  95
Lys Cys Lys Val Ser Asn Lys Ala Leu Pro Ala Pro Ile Glu Lys Thr
            100                 105                 110
Ile Ser Lys Ala Lys Gly Gln Pro Arg Glu Pro Gln Val Cys Thr Leu
        115                 120                 125
Pro Pro Ser Arg Asp Glu Leu Thr Lys Asn Gln Val Ser Leu Ser Cys
    130                 135                 140
Ala Val Lys Gly Phe Tyr Pro Ser Asp Ile Ala Val Glu Trp Glu Ser
145                 150                 155                 160
Asn Gly Gln Pro Glu Asn Asn Tyr Lys Thr Thr Pro Pro Val Leu Asp
                165                 170                 175
Ser Asp Gly Ser Phe Phe Leu Val Ser Lys Leu Thr Val Asp Lys Ser
            180                 185                 190
Arg Trp Gln Gln Gly Asn Val Phe Ser Cys Ser Val Met His Glu Ala
        195                 200                 205
Leu His Asn His Tyr Thr Gln Lys Ser Leu Ser Leu Ser Pro Gly Lys
    210                 215                 220

<210> SEQ ID NO 72
<211> LENGTH: 230
<212> TYPE: PRT
<213> ORGANISM: Artificial Sequence
<220> FEATURE:
<223> OTHER INFORMATION: Heavy chain Fc-region polypeptide (human
      IgG1(CH2-CH3)) with T366W mutation containing a N-terminal
``` gggdkthtcppc sequence

<400> SEQUENCE: 72

Gly Gly Gly Asp Lys Thr His Thr Cys Pro Pro Cys Pro Ala Pro Glu
1               5                   10                  15

Leu Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Cys Arg Asp Glu Leu Thr Lys Asn
    130                 135                 140

Gln Val Ser Leu Trp Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
    210                 215                 220

Ser Leu Ser Pro Gly Lys
225                 230

<210> SEQ ID NO 73
<211> LENGTH: 226
<212> TYPE: PRT
<213> ORGANISM: Artificial Sequence
<220> FEATURE:
<223> OTHER INFORMATION: Heavy chain Fc-region polypeptide (human
      IgG1(CH2-CH3)) with T366W mutations containing a N-terminal
      gghtcppc sequence

<400> SEQUENCE: 73

Gly Gly His Thr Cys Pro Pro Cys Pro Ala Pro Glu Leu Leu Gly Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

```
Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
        115                 120                 125

Thr Leu Pro Pro Cys Arg Asp Glu Leu Thr Lys Asn Gln Val Ser Leu
    130                 135                 140

Trp Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220

Gly Lys
225

<210> SEQ ID NO 74
<211> LENGTH: 224
<212> TYPE: PRT
<213> ORGANISM: Artificial Sequence
<220> FEATURE:
<223> OTHER INFORMATION: Heavy chain Fc-region polypeptide (human
      IgG1(CH2-CH3)) with T366W mutation containing a N-terminal ggcppc
      sequence

<400> SEQUENCE: 74

Gly Gly Cys Pro Pro Cys Pro Ala Pro Glu Leu Leu Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Cys Arg Asp Glu Leu Thr Lys Asn Gln Val Ser Leu Trp Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
```

<210> SEQ ID NO 75
<211> LENGTH: 22
<212> TYPE: PRT
<213> ORGANISM: Artificial Sequence
<220> FEATURE:
<223> OTHER INFORMATION: Sortase tag example

<400> SEQUENCE: 75

Lys Ser Cys Gly Gly Gly Ser Leu Pro Glu Thr Gly Gly Ser Gly Ser
1               5                   10                  15

His His His His His His
            20

<210> SEQ ID NO 76
<211> LENGTH: 20
<212> TYPE: PRT
<213> ORGANISM: Artificial Sequence
<220> FEATURE:
<223> OTHER INFORMATION: Sortase tag example

<400> SEQUENCE: 76

Lys Ser Cys Gly Ser Leu Pro Glu Thr Gly Gly Ser Gly Ser His His
1               5                   10                  15

His His His His
            20

<210> SEQ ID NO 77
<211> LENGTH: 18
<212> TYPE: PRT
<213> ORGANISM: Artificial Sequence
<220> FEATURE:
<223> OTHER INFORMATION: Sortase tag example

<400> SEQUENCE: 77

Lys Ser Cys Leu Pro Glu Thr Gly Gly Ser Gly Ser His His His His
1               5                   10                  15

His His

<210> SEQ ID NO 78
<211> LENGTH: 5
<212> TYPE: PRT
<213> ORGANISM: Artificial Sequence
<220> FEATURE:
<223> OTHER INFORMATION: Sortase motif

<400> SEQUENCE: 78

Leu Pro Glu Thr Gly
1               5

<210> SEQ ID NO 79
<211> LENGTH: 12
<212> TYPE: PRT
<213> ORGANISM: Artificial Sequence
<220> FEATURE:
<223> OTHER INFORMATION: Synthetic Construct

<400> SEQUENCE: 79

Lys Ser Cys Gly Gly Gly Ser Leu Pro Glu Thr Gly
1               5                   10

<210> SEQ ID NO 80
<211> LENGTH: 10
<212> TYPE: PRT

<213> ORGANISM: Artificial Sequence
<220> FEATURE:
<223> OTHER INFORMATION: Synthetic Construct

<400> SEQUENCE: 80

Lys Ser Cys Gly Ser Leu Pro Glu Thr Gly
1               5                   10

<210> SEQ ID NO 81
<211> LENGTH: 13
<212> TYPE: PRT
<213> ORGANISM: Artificial Sequence
<220> FEATURE:
<223> OTHER INFORMATION: Synthetic Construct

<400> SEQUENCE: 81

Gly Gly Gly Ser Leu Pro Glu Thr Gly Gly Ser Gly Ser
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Synthetic Construct

<400> SEQUENCE: 82

Gly Ser Leu Pro Glu Thr Gly Gly Ser Gly Ser
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Synthetic Construct

<400> SEQUENCE: 83

Cys Gly Ser Leu Pro Glu Thr Gly Gly Ser Gly Ser
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 13
<223> OTHER INFORMATION: Attached to an amino acid sequence tag

<400> SEQUENCE: 84

Gly Gly Gly Ser Leu Pro Glu Thr Gly Gly Ser Gly Ser
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 11
<223> OTHER INFORMATION: Attached to an amino acid sequence tag

```
<400> SEQUENCE: 85

Gly Ser Leu Pro Glu Thr Gly Gly Ser Gly Ser
1               5                   10
```